US012758518B2

(12) United States Patent
Napier et al.

(10) Patent No.: US 12,758,518 B2
(45) Date of Patent: *Oct. 13, 2026

(54) PRODUCTION OF OMEGA-3 LONG CHAIN POLYUNSATURATED FATTY ACIDS

(71) Applicant: Rothamsted Research Ltd., Hertfordshire (GB)

(72) Inventors: Johnathan Napier, Hertfordshire (GB); Olga Sayanova, Hertfordshire (GB); Noemi Ruiz Lopez, Hertfordshire (GB); Richard Haslam, Buckinghamshire (GB)

(73) Assignee: Rothamsted Research Ltd., Hertfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/139,232

(22) Filed: Dec. 31, 2020

(65) Prior Publication Data

US 2021/0290577 A1 Sep. 23, 2021

Related U.S. Application Data

(63) Continuation of application No. 14/391,818, filed as application No. PCT/GB2013/050955 on Apr. 12, 2013, now Pat. No. 10,881,631.

(30) Foreign Application Priority Data

Apr. 12, 2012 (GB) ..................................... 1206483
Dec. 10, 2012 (GB) ..................................... 1222184

(51) Int. Cl.
*A61K 31/20* (2006.01)
*A61K 31/202* (2006.01)
*C12N 15/82* (2006.01)

(52) U.S. Cl.
CPC ........ *A61K 31/202* (2013.01); *C12N 15/8247* (2013.01)

(58) Field of Classification Search
CPC .......................... C12N 15/8247; A61K 31/202
See application file for complete search history.

(56) References Cited

U.S. PATENT DOCUMENTS

| | | | | |
|---|---|---|---|---|
| 4,962,028 | A | 10/1990 | Bedbrook et al. | |
| 5,057,419 | A | 10/1991 | Martin et al. | |
| 5,187,267 | A | 2/1993 | Comai et al. | |
| 5,352,605 | A | 10/1994 | Fraley et al. | |
| 5,443,974 | A | 8/1995 | Hitz et al. | |
| 5,504,200 | A | 4/1996 | Hall et al. | |
| 5,608,152 | A | 3/1997 | Kridl et al. | |
| 5,614,393 | A | 3/1997 | Thomas et al. | |
| 5,968,809 | A | 10/1999 | Knutzon et al. | |
| 5,972,664 | A | 10/1999 | Knutzon et al. | |
| 6,075,183 | A | 6/2000 | Knutzon et al. | |
| 10,881,631 | B2 * | 1/2021 | Napier | A61K 8/922 |
| 2002/0139974 | A1 | 10/2002 | Matsushita et al. | |
| 2003/0196217 | A1 | 10/2003 | Mukerji et al. | |
| 2008/0076164 | A1 | 3/2008 | Cirpus | |
| 2008/0155705 | A1 * | 6/2008 | Zank | C12N 9/1029 800/13 |
| 2009/0151023 | A1 | 6/2009 | Kuvshinov et al. | |
| 2009/0151028 | A1 | 6/2009 | Kuvshinov et al. | |
| 2009/0172837 | A1 * | 7/2009 | Geiger | A23L 33/12 554/8 |
| 2009/0222951 | A1 * | 9/2009 | Cirpus | A61P 3/04 536/23.6 |
| 2009/0234006 | A1 | 9/2009 | Cirpus et al. | |
| 2010/0088776 | A1 | 4/2010 | Bauer et al. | |
| 2011/0138490 | A1 | 6/2011 | Bauer | |
| 2011/0162105 | A1 * | 6/2011 | Bauer | C12N 9/0004 435/189 |
| 2012/0016144 | A1 * | 1/2012 | Petrie | C12P 7/6472 554/9 |
| 2012/0124705 | A1 | 5/2012 | Bauer | |

FOREIGN PATENT DOCUMENTS

| | | | |
|---|---|---|---|
| CA | 2533613 | A1 | 9/1967 |
| CA | 768082 | A1 | 2/2005 |
| EP | 0375091 | A1 | 6/1990 |
| JP | 2007-527716 | A | 10/2007 |
| WO | 84/02913 | A1 | 8/1984 |
| WO | 91/13972 | A1 | 9/1991 |
| WO | 91/13980 | A1 | 9/1991 |
| WO | 93/06712 | A1 | 4/1993 |
| WO | 94/11516 | A1 | 5/1994 |
| WO | 95/16783 | A1 | 6/1995 |
| WO | 95/19443 | A2 | 7/1995 |
| WO | 96/12814 | A1 | 5/1996 |
| WO | 93/11245 | A1 | 6/1996 |

(Continued)

OTHER PUBLICATIONS

Petrie et al: Rapid expression of transgenes driven by seed-specific constructs in leaf tissue: DHA production. Plant Methods, 6:8, 2010 (Year: 2010).*
Sayanova et al (The role of Δ6-desaturase acyl-carrier specificity in the efficient synthesis of long-chain polyunsaturated fatty acids in transgenic plants. Plant Biotechnology Journal 10, pp. 195-206, first published Sep. 8, 2011) (Year: 2011).*
Napier et al (Transgenic plants as a sustainable, terrestrial source of fish oils. Eur. J. Lipid Sci. Technol. 117, 1317-1324, 2015) (Year: 2015).*
Cheng et al (Towards the production of high levels of eicosapentaenoic acid in transgenic plants: the effects of different host species, genes and promoters. Transgenic Res, 19:221-229, 2010) (Year: 2010).*
Miladinovic et al (Editorial: Advances in Oil Crops Research-Classical and New Approaches to Achieve Sustainable Productivity. Frontiers in Plant Science, 1-4, 2019) (Year: 2019).*

(Continued)

*Primary Examiner* — Wayne Zhong
(74) *Attorney, Agent, or Firm* — Tarolli, Sundheim, Covell & Tummino LLP

(57) ABSTRACT

A recombinant camelina plant or cell comprising one or more polynucleotides encoding a A6-desaturase, a A6-elongase and a A5-desaturase operably linked with one or more regulatory sequences.

18 Claims, 11 Drawing Sheets

Specification includes a Sequence Listing.

(56) References Cited

FOREIGN PATENT DOCUMENTS

| | | | |
|---|---|---|---|
| WO | 96/21022 | A2 | 7/1996 |
| WO | 97/06250 | A1 | 2/1997 |
| WO | 98/45461 | A1 | 10/1998 |
| WO | 98/46763 | A1 | 10/1998 |
| WO | 98/46764 | A1 | 10/1998 |
| WO | 98/46765 | A1 | 10/1998 |
| WO | 99/27111 | A1 | 6/1999 |
| WO | 99/46394 | A1 | 9/1999 |
| WO | 00/12720 | A2 | 3/2000 |
| WO | 00/21557 | A1 | 4/2000 |
| WO | 02/090493 | A2 | 11/2002 |
| WO | 03/099216 | A2 | 12/2003 |
| WO | 2005/012316 | A2 | 2/2005 |
| WO | 2006/100241 | A2 | 9/2006 |
| WO | 2008/022963 | A2 | 2/2008 |
| WO | 2009/133145 | A1 | 11/2009 |
| WO | 2011/006948 | A1 | 1/2011 |
| WO | 2011/064181 | A1 | 6/2011 |

OTHER PUBLICATIONS

Wanasundara et al.(Chapter 14. Omega-3 Fatty Acid Concentrates: a Review of Production Technologies. Quality, Technology and Nutraceutical Applications. 157-174, 2002). (Year: 2002).*

Ruiz-Lopez et al (Metabolic engineering of the omega-3 long chain polyunsaturated fatty acid biosynthetic pathway into transgenic plants. Journal of Experimental Botany, vol. 63, No. 7, pp. 2397-2410, published Jan. 2012) (Year: 2012).*

Thies et al (Dietary Supplementation with g-Linolenic Acid or Fish Oil Decreases T Lymphocyte Proliferation in Healthy Older Humans. Fatty Acids and Human Lymphocytes. 1918-1927, 2001) (Year: 2001).*

Laidlaw et al (Effects of supplementation with fish oil-derived n-3 fatty acids and gamma-linolenic acid on circulating plasma lipids and fatty acid profiles in women. Am J Clin Nutr.77:37-42, 2003). (Year: 2003).*

Klinska-Bachor et al (Metabolic engineering of omega-3 long chain polyunsaturated fatty acids in plants using different Δ6-and Δ5-desaturases co-expressed with LPCAT from the marine diatom Phaeodactylum tricornutum. Nature Scientific Report, 1-13, 2024) (Year: 2024).*

Patrie et al (Metabolic Engineering Plant Seeds with Fish Oil-Like Levels of DHA. PLOS ONE. 1-7, Nov. 2012) (Year: 2012).*

Han et al (High level accumulation of EPA and DHA in field-grown transgenic Camelina—a multi-territory evaluation of TAG accumulation and heterogeneity, Plant Biotechnology Journal, 18, pp. 2280-2291, 2020) (Year: 2020).*

Petruzzello (list of plants in the family Brassicaceae, published 2024) (Year: 2024).*

Domergue et al (In vivo characterization of the first acyl-CoA-6-desaturase from a member of the plant kingdom, the microalga Ostreococcus tauri. Biochem. J. 389, 483-490, 2005) (Year: 2005).*

Schaefer et al., "Plasma Phosphatidylcholine Docosahexaenoic Acid Content and Risk of Dementia and Alzheimer Disease: The Framingham Heart Study," Archives of Neurology, 63: 1545-1550 (2006).

Smith et al., "Comparison of Biosequences," Advances in Applied Mathematics, 2: 482-489 (1981).

Söderberg et al., "Fatty Acid Composition of Brain Phospholipids in Aging and in Alzheimer's Disease," Lipids, 26: 421-425 (1991).

Suzuki et al., "Effect of the long-term feeding of dietary lipids on the learning ability, fatty acid composition of brain stem phospholipids and synaptic membrane fluidity in adult mice: a comparison of sardine oil diet with palm oil diet," Mechanisms of Ageing and Development, 101: 119-128 (1998).

Tocher et al., "Recent Advances in the Biochemistry and Molecular Biology of Fatty Acyl Desaturases," Progress in Lipid Research, 37: 73-117 (1998).

Tonon et al., "Fatty acid desaturases from the microalga Thalassiosira pseudonana," The FEBS Journal, 272: 3401-3412.

Truksa et al., "Molecular analysis of flax 2S storage protein conlinin and seed specific activity of its promoter," Plant Physiology and Biochemistry, 41: 141-147 (2003).

Jauy et al., "Nutrition in brain development and aging: Role of essential fatty acids," Nutrition Reviews, 64: S24-S33 (2006).

Van Gelder et al., "Fish consumption, n-3 fatty acids, and subsequent 5-y cognitive decline in elderly men: the Zutphen Elderly Study," American Journal of Clinical Nutrition, 85: 1142-1147 (2007).

Venegas-Calerón et al., "An alternative to fish oils: Metabolic engineering of oil-seed crops to produce omega-3 long chain polyunsaturated fatty acids," Progress in Lipid Research, 49: 108-119 (2010).

Ward et al., "Chemical regulation of transgene expression in plants, " Plant Molecular Biology, 22: 361-366 (1993).

Welti et al., "Profiling Membrane Lipids in Plant Stress Responses," The Journal of Biological Chemistry, 277: 31994-32002 (2002).

Whalley et al., "Cognitive aging, childhood intelligence, and the use of food supplements: possible involvement of n-3 fatty acids," American Journal of Clinical Nutrition, 80: 1650-1657 (2004).

Whalley et al., "n-3 Fatty acid erythrocyte membrane content, APOE ϵ4, and cognitive variation: an observational follow-up study in late adulthood," American Journal of Clinical Nutrition, 87: 449-454 (2008).

Wu et al., "Stepwise engineering to produce high yields of very long-chain polyunsaturated fatty acids in plants," Nature Biotechnology, 23: 1013-1017 (2005).

Yurko-Mauro et al., "Beneficial effects of docosahexaenoic acid on cognition in age-related cognitive decline," Alzheimer's & Dementia, 6: 456-464 (2010).

Zank et al., "Cloning and functional characterisation of an enzyme involved in the elongation of Δ6-polyunsaturated fatty acids from the moss Physcomitrella patens," The Plant Journal, 31: 255-268 (2002).

Budin et al., "Some Compositional Properties of Camelina (*Camelina sativa L. Crantz*) Seeds and Oils, " Journal of American Oil Chemists Society, 72: 309-315 (1995).

Domergue et al., "Cloning and functional characterization of Phaeodactylum tricornutum front-end desaturases involved in eicosapentaenoic acid biosynthesis," European Journal of Biochemistry, 269: 4105-4113 (2002).

Ausubel ed., "Short Protocols in Molecular Biology: A Compendium of Methods from Current Protocols in Molecular Biology," 3rd Edition, Chapters 9, 13, 16 (1995).

Gait ed., "Oligonucleotide synthesis: a practical approach," (1984).

Lilley ed., "Methods in Enzymology: vol. 211: DNA Structures: Part A: Synthesis and Physical Analysis of DNA," (1992).

Polak ed., "In Situ Hybridization: Principles and Practice" (1990).

Roe et al., "DNA Isolation and Sequencing: Essential Techniques" (1996).

Sambrook ed., "Molecular Cloning: A Laboratory Manual," Second Edition, Books 1-3 (1989).

Simopoulos ed., "Health Effects of Polyunsaturated Fatty Acids in Seafoods" (1986).

Weete ed., "Lipid Biochemistry of Fungi and Other Organisms" (1980).

Kalmijn et al., (2004) "Dietary Intake of Fatty Acids and Fish in relation to Cognitive Performance at Middle Age", Neurology 62, pp. 275-280.

Van de Rest et al., (Aug. 2008) "Effect of Fish Oil on Cognitive Performance in Older Subjects", Neurology 71, pp. 430-438.

Wassef, M. (1977) "Fungal lipids." Adv. Lipid Research, pp. 159-232.

Xiao et al. (May 2010) "Overexpression of *Arabidopsis* Acyl-CoA Binding Protein ACBP3 Promotes Starvation-Induced and Age-Dependent leaf Senescence" The Plant Cell, vol. 22, pp. 1463-1482.

Krank et al. (2007) "Qualitative Analysis and Quantitative Assessment of Changes in neutral Glycerol Lipid Molecular Species Within Cells", Methods in Enzymology, vol. 432, pp. 1-20.

Abbadi et al., "Biosynthesis of Very-Long-Chain Polyunsaturated Fatty Acids in Transgenic Oilseeds: Constraints on Their Accumulation," The Plant Cell, 16: 2734-2748 (2004).

(56) References Cited

OTHER PUBLICATIONS

Bäumlein et al., "A novel seed protein gene from Vicia faba is developmentally regulated in transgenic tobacco and *Arabidopsis* plants," Molecular & General Genetics, 225: 459-467 (1991).
Bäumlein et al., "Cis-analysis of a seed protein gene promoter: the conservative RY repeat CATGCATG within the legumin box is essential for tissue-specific expression of a legumin gene," The Plant Journal, 2: 233-239 (1992).
Beaudoin et al., "Heterologous reconstitution in yeast of the polyunsaturated fatty acid biosynthetic pathway," Proceedings of the National Academy of Sciences, 97: 6421-6426 (2000).
Becker et al., "New plant binary vectors with selectable markers located proximal to the left T-DNA border," Plant Molecular Biology, 20: 1195-1197 (1992).
Benfey et al., "The CaMV 35S enhancer contains at least two domains which can confer different developmental and issue-specific expression patterns," The EMBO Journal, 8: 2195-2202 (1989).
Bernardo et al., "Camelina oil as a fuel for diesel transport engines," Industrial Crops and Products, 17: 191-197 (2003).
Bevan, "Binary Agrobacterium vectors for plant transformation," Nucleic Acids Research, 12: 8711-8721 (1984).
Cheng et al., "Towards the production of high levels of eicosapentaenoic acid in transgenic plants: the effects of different host species, genes and promoters," Transgenic Research, 19: 221-229 (2010).
Chiu et al., "The effects of omega-3 fatty acids monotherapy in Alzheimer's disease and mild cognitive impairment: A preliminary randomized double-blind placebo-controlled study," Progress in Neuro-Psychopharmacology & Biological Psychiatry, 32: 1538-1544 (2008).
Chung et al., "Fish Oil Supplementation of Control and (n-3) Fatty Acid-Deficient Male Rates Enhances Reference and Working Memory Performance and Increases Brain Regional Docosahexaenoic Acid Levels," The Journal of Nutrition, 138: 1165-1171 (2008).
Dangour et al., "Fish Consumption and Cognitive Function Among Older People in the UK: Baseline Data from the Opal Study," The Journal of Nutrition, Health & Aging, 13: 198-202 (2008).
Dangour et al., "Effect of 2-y n-3 long-chain polyunsaturated fatty acid supplementation on cognitive function in older people: a randomized, double-blind, controlled trail," The American Journal of Clinical Nutrition, 91: 1725-1732 (2010).
Devaiah et al., "Quantitative profiling of polar glycerolipid species from organs of wild-type *Arabidopsis* and Phospholipase D$\alpha$1 knockout mutant," Phytochemistry, 67: 1907-1924 (2006).
Domergue et al., "In vivo characterization of the first acyl-CoA $\Delta$6-desaturase from a member of the plant kingdom, the microalga Ostreococcus tauri," Biochemical Journal, 389: 483-490 (2005).
Franck et al., "Nucleotide Sequence of Cauliflower Mosaic Virus DNA," Cell, 21: 285-294 (1980).
Freund-Levi et al., "ω-3 Fatty Acid Treatment in 174 Patients With Mild to Moderate Alzheimer Disease: OmegAD Study," Archives of Neurology, 63: 1402-1408 (2006).
Fröhlich et al., "Evaluation of Camelina sativa oil as a feedstock for biodiesel production," Industrial Crops and Products, 21: 25-31 (2005).
Gatz, "Chemical Control of Gene Expression," Annual Review of Plant Physiology and Plant Molecular Biology, 48: 89-108 (1997).
Gatz et al., "Stringent repression and homogeneous de-repression by tetracycline of a modified CaMV 35S promoter in intact transgenic tobacco plants," The Plant Journal, 2: 397-404 (1992).
Gehringer et al., "Genetic mapping of agronomic traits in false flax (*Camelina sativa* subsp. *sativa*)," Genome, 49: 1555-1563 (2006).
Gielen et al., "The complete nucleotide sequence of the TL-DNA of the *Agrobacterium* tumefaciens plasmid pTiAch5," The EMBO Journal, 3: 835-846 (1984).
Gugel et al., "Agronomic and seed quality evaluation of Camelina sativa in western Canada," Canadian Journal of Plant Science, 86: 1047-1058 (2006).
Haynes et al., "Quantitation of fatty acyl-coenzyme as in mammalian cells by liquid chromatography-electrospray ionization tandem massy spectrometry," Journal of Lipid Research, 49: 1113-1125 (2008).
Heude et al., "Cognitive decline and fatty acid composition of erythrocyte membranes—The EVA Study," American Journal of Clinical Nutrition, 77: 803-808 (2003).
Hoffmann et al., "Metabolic Engineering of ω3-Very Long Chain Polyunsaturated Fatty Acid Production by an Exclusively Acyl-CoA-dependent Pathway," Journal of Biological Chemistry, 283: 22352-22362 (2008).
Hong et al., "High-Level Production of $\gamma$-Linolenic Acid in Brassica juncea Using a $\Delta$6 Desaturase from Pythium irregulare," Plant Physiology, 129: 354-362 (2002).
Kalmijn et al., "Polyunsaturated Fatty Acids, Antioxidants, and Cognitive Function in Very Old Men," American Journal of Epidemiology, 145: 33-41 (1997).
Kalmijn et al., "Dietary Fat Intake and the Risk of Incident Dementia in the Rotterdam Study," Annals of Neurology, 42: 776-782 (1997).
Kermode, "Mechanisms of Intracellular Protein Transport and Targeting in Plant Cells," Critical Reviews in Plant Sciences, 15: 285-423 (1996).
Larson et al., "A novel technique for the sensitive quantification of acyl CoA esters from plant tissues," The Plant Journal, 25: 115-125 (2001).
Lu et al., "Generation of transgenic plants of a potential oilseed crop Camelina sativa by Agrobacterium-mediated transformation," Plant Cell Reports, 27: 273-278 (2008).
Matthes et al., "The transcriptome of cis-jasmone-induced resistance in *Arabidopsis thaliana* and its role in indirect defence," Planta, 232: 1163-1180 (2010).
Melnikov et al., "Random mutagenesis by recombinational capture of PCR products in Bacillus subtilis and Acinetobacter calcoaceticus," Nucleic Acids Research, 27: 1056-1062 (1999).
Meyer et al., "Novel fatty acid elongases and their use for the reconstitution of docosahexaenoic acid biosynthesis," Journal of Lipid Research, 45: 1899-1909 (2004).
Moriguchi et al., "Recovery of brain docosahexaenoate leads to recovery of spatial task performance," Journal of Neurochemistry, 87: 297-309 (2003).
Morris et al., "Consumption of Fish and n-3 Fatty Acids and Risk of Incident Alzheimer Disease," Archives of Neurology, 60: 940-946 (2003).
Morris et al., "Fish Consumption and Cognitive Decline with Age in a Large Community Study," Archives of Neurology, 62: 1-5 (2005).
Nurk et al., "Cognitive performance among the elderly and dietary fish intake: the Hordaland Health Study," The American Journal of Clinical Nutrition, 86: 1470-1478 (2007).
Pearson, "Rapid and Sensitive Sequence Comparison with FASTP and FASTA," Methods in Enzymology, 183: 63-98 (1990).
Qiu et al., "Identification of a $\Delta$4 Fatty Acid Desaturase from *Thraustochytrium* sp. Involved in the Biosynthesis of Docosahexanoic Acid by Heterologous Expression in *Saccharomyces cerevisiae* and *Brassica juncea*," The Journal of Biological Chemistry, 276: 31561-31566 (2001).
Robert et al., "Metabolic engineering of *Arabidopsis* to produce nutritionally important DHA in seed oil," Functional Plant Biology, 32: 473-479 (2005).
Ruiz-López et al., "Metabolic engineering of the omega-3 long chain polyunsaturated fatty acid biosynthetic pathway Into transgenic plants," Journal of Experimental Botany, 63: 2397-2410 (2012).
Ruiz-López et al., "Enhancing the accumulation of omega-3 long chain polyunsaturated fatty acids in transgenic *Arabidopsis thaliana* via iterative metabolic engineering and genetic crossing," Transgenic Research, 21: 1233-1243 (2012).
Sayanova et al., "Expression of a borage desaturase cDNA containing an N-terminal cytochrome b5 domain results in the accumulation of high levels of $\Delta$6-desaturated fatty acids in transgenic tobacco," Proceedings of the National Academy of Sciences, 94: 4211-4216 (1997).

(56) References Cited

OTHER PUBLICATIONS

Sayanova et al., "Identification of Primula fatty acid Δ6-desturases with n-3 substrate preferences," FEBS Letters, 542:100-104 (2003).
Sayanova et al., "Identification and functional characterisation of genes encoding the omega-3 polyunsaturated fatty acid biosynthetic pathway from the coccolithophore Emiliania huxleyi," Phytochemistry, 72: 594-600 (2011).
Sayanova et al., "The role of Δ6-desaturase acyl-carrier specificity in the efficient synthesis of long-chain polyunsaturated fatty acids in transgenic plants, " Plant Biotechnology Journal, 10: 195-206 (2012).
Sayanova et al., "Transgenic oilseed crops as an alternative to fish oils," Prostaglandins, Leukotrienes and Essential Fatty Acids, 85: 253-260 (2011).
Neuringer, et al., (1988) "The Essentiality of N-3 Fatty Acids for the Development and Function of the Retina and Brain", Annual Rev. Nutr. 8, pp. 517-541.
Yuan, Lixia, and Runzhi Li. "Metabolic engineering a model oilseed Camelina sativa for the sustainable production of high-value designed oils." Frontiers in Plant Science 11 (2020): 11.
Bakhytkyzy, Inal, Weronika Hewelt-Belka, and Agata Kot-Wasik. "A comprehensive lipidomic analysis of oilseeds using LC-Q-TOF-MS and dispersive micro-solid phase (D-μ-SPE) extraction techniques." Journal of Food Composition and Analysis 116 (2023): 105037.

* cited by examiner

Fig2

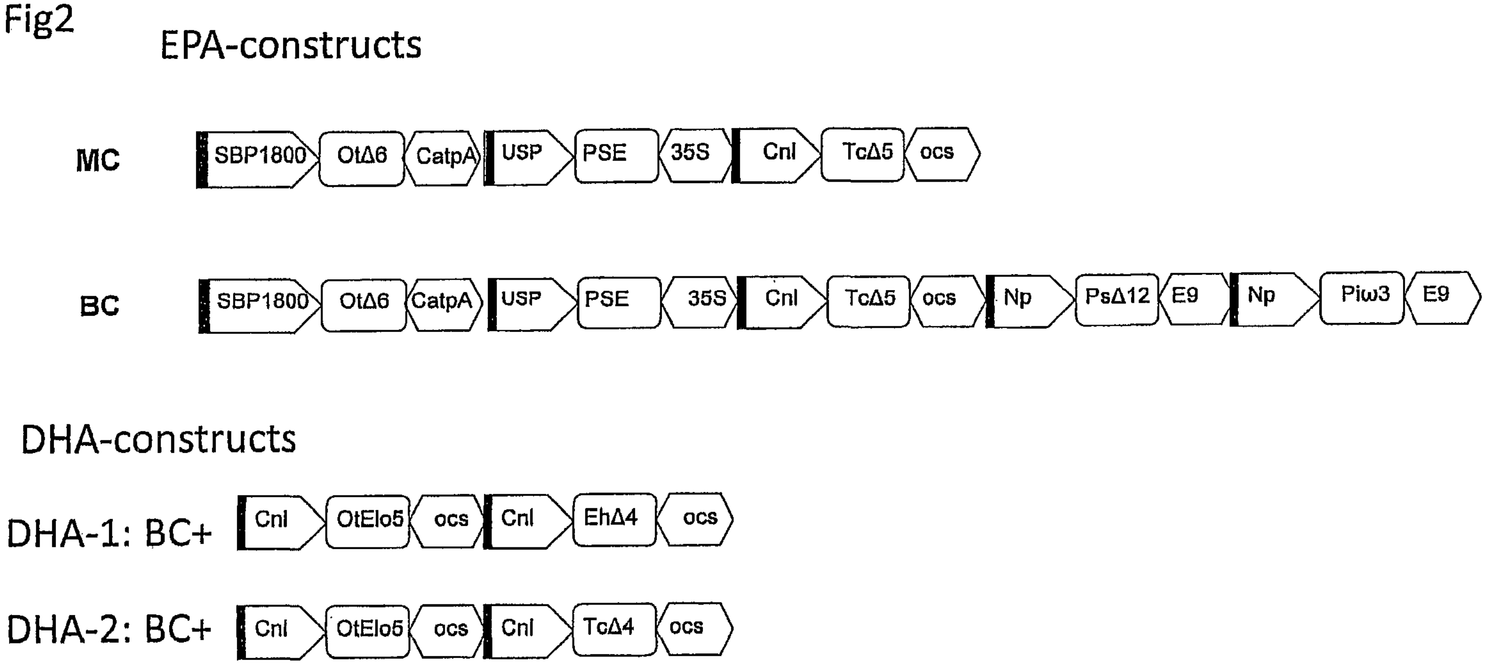

Simplified maps of the vector constructs used for Camelina transformation.

Cnl, conlinin 1promoter for the gene encoding the flax 2S storage protein conlinin; USP, promoter region of the unknown seed protein of *V.faba*; SBP1800; NP, napin; OtΔ6, a Δ6-desaturase from *O. taurii*; TcΔ5- a Δ5-desaturase from *Thraustochytrium* sp.; Pi ω3- an ω-3 desaturase from *P. infestans;* PsΔ12- a Δ12-desaturase from *P. sojae;* EhΔ4 – a Δ4-desaturases from *Emiliania huxleyi*; PSE1, a Δ6-elongase from *P. patens,* OtElo5- Δ5-elongase from *Ostreococcus tauri*; OCS, 35S, E9 and CatpA – represent terminators.

Fig 6 – Distribution of acyl chains within phospholipids of WT and EPA- accumulating Camelina: phosphatidylcholine (PC)

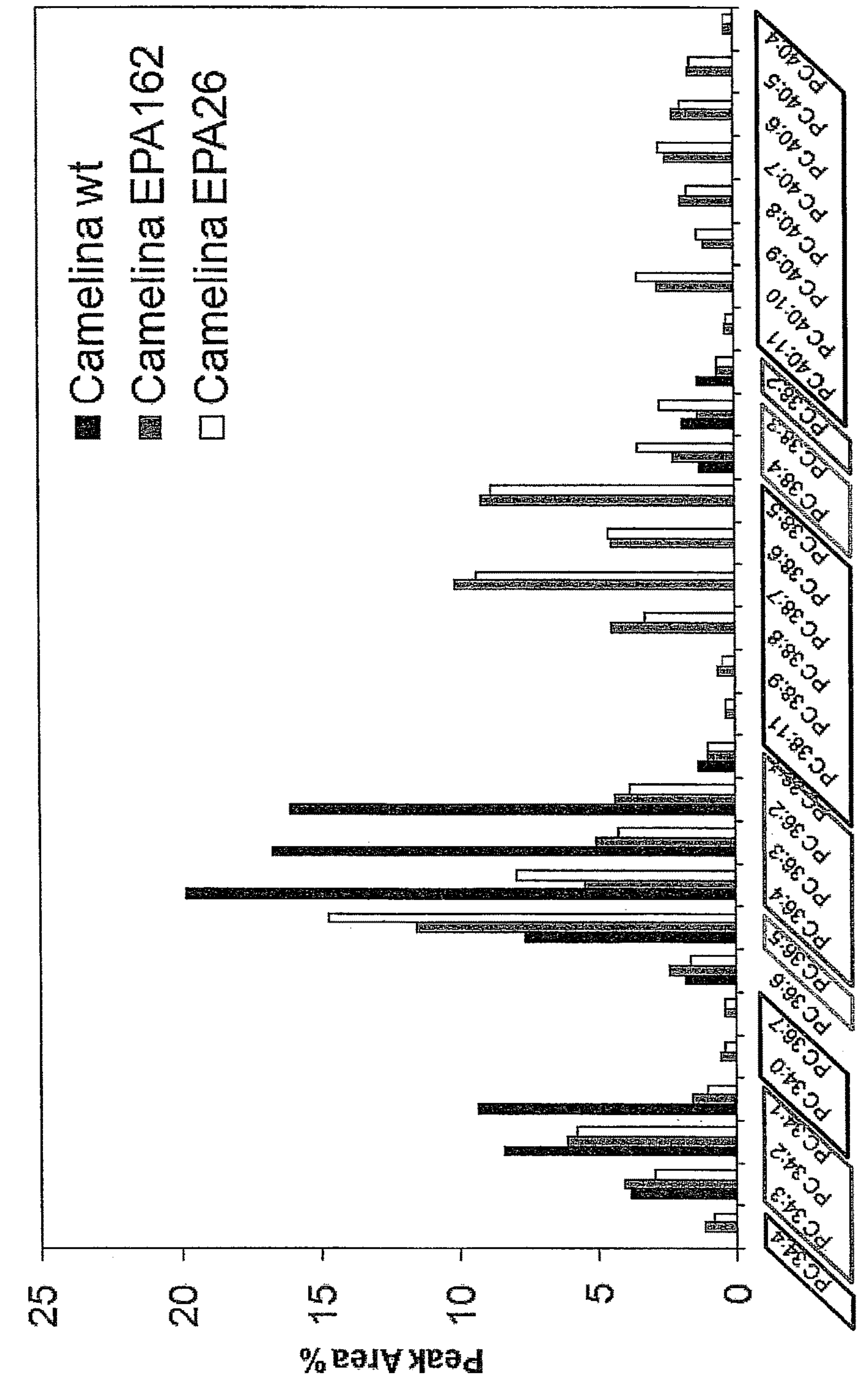

Novel species of PC present in transgenic lines indicated with red boxes [classification based on total chain length for sn-1 and sn-2 positions, and number of double bonds]
PC species significantly reduced in transgenics are boxed in blue; orange box = increased above WT levels Fig 7 – Distribution of acyl chains within phospholipids of WT and EPA- accumulating Camelina: phosphatidylethanolamine (PE)

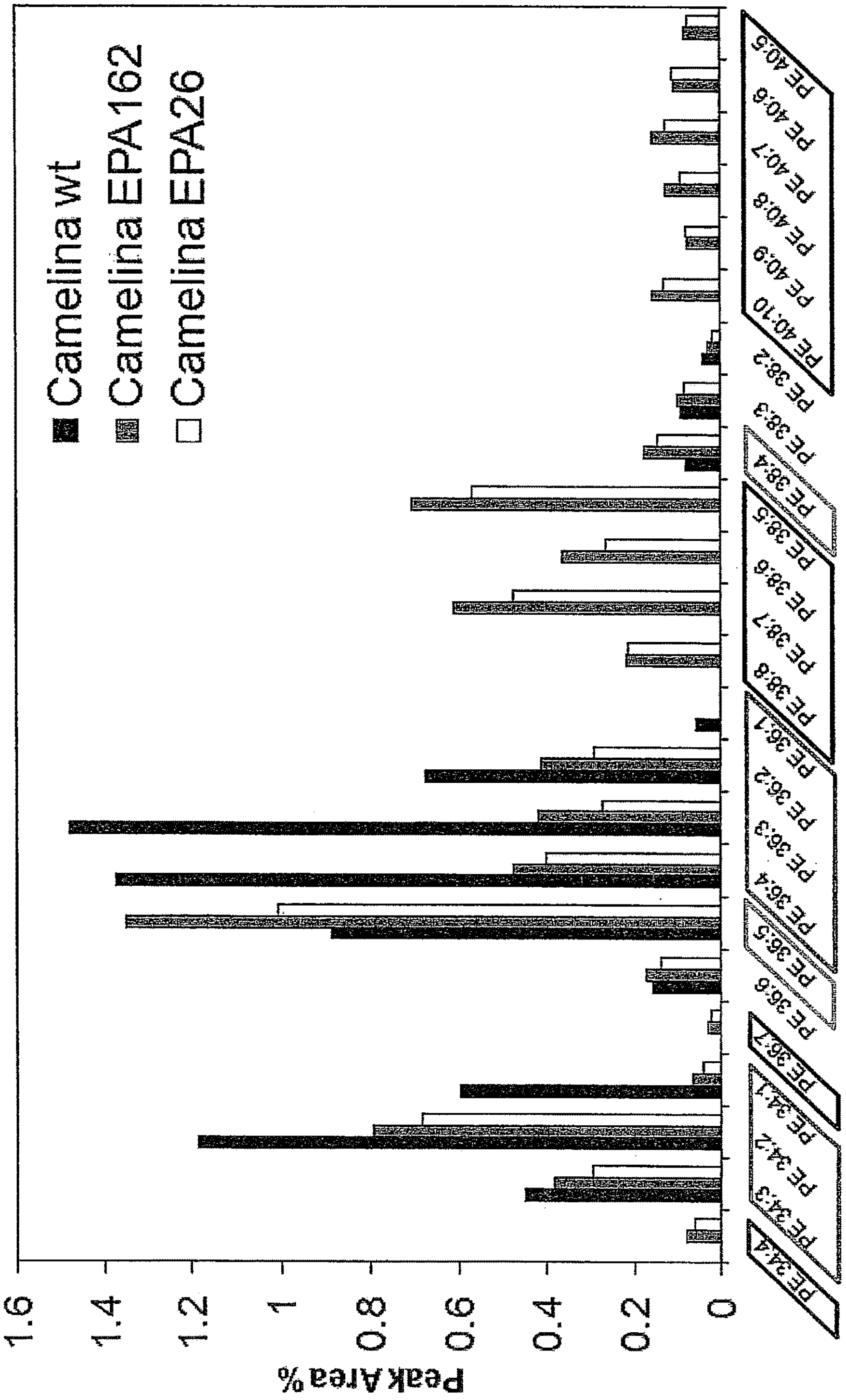

Novel species of PE present in transgenic lines indicated with red boxes [classification based on total chain length for sn-1 and sn-2 positions, and number of double bonds] PE species significantly reduced in transgenics are boxed in blue; orange =increased above WT Fig 8 – Distribution of acyl chains within phospholipids of WT and EPA- accumulating Camelina: phosphatidic acid (PA) and phosphoinositol (PI)

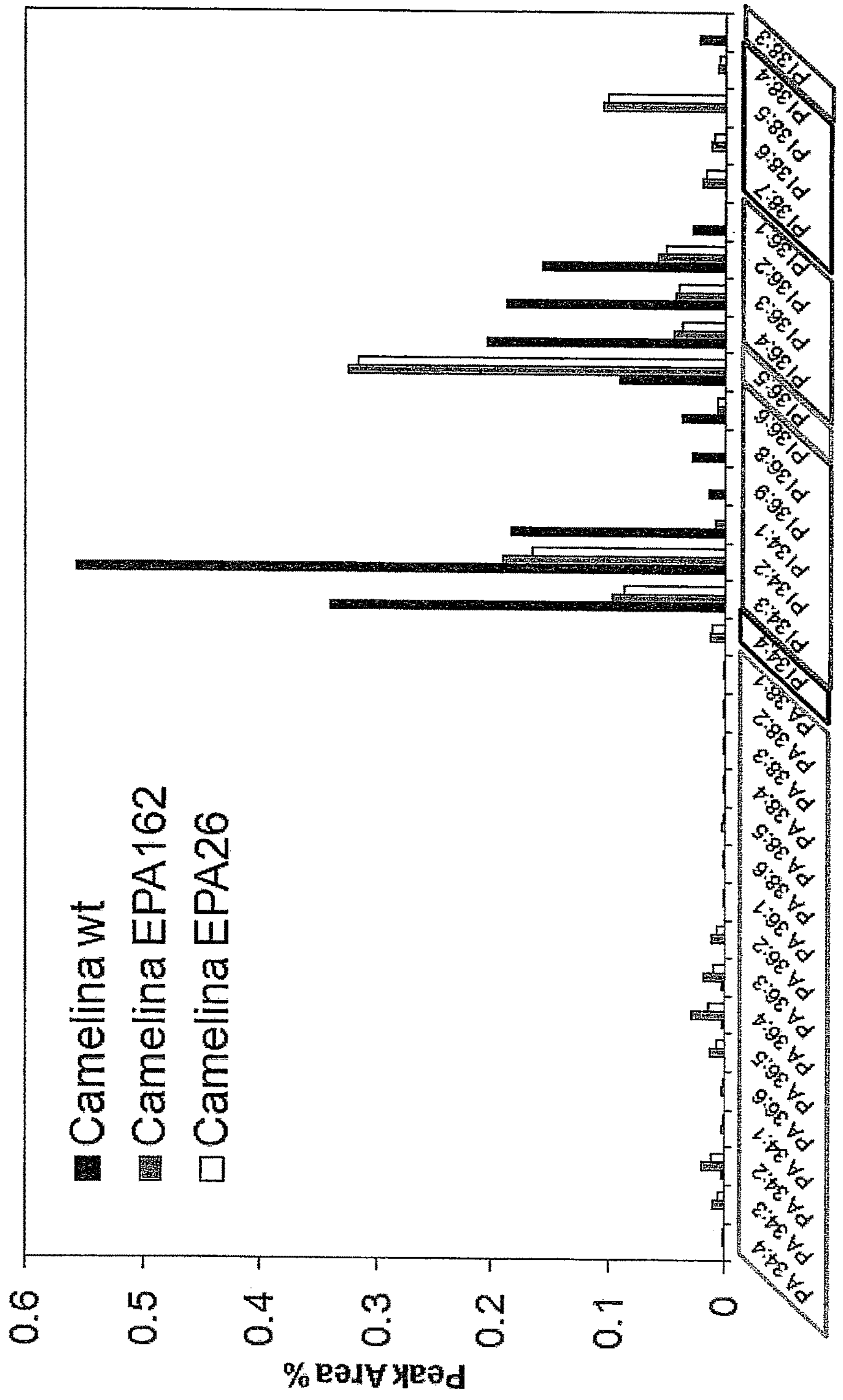

Novel species of PA or PI present in transgenic lines indicated with red boxes [classification based on total chain length for sn-1 and sn-2 positions, and number of double bonds] PA/PI species significantly reduced in transgenics are boxed in blue; orange =increased above WT Fig 9 – Distribution of acyl chains within phospholipids of WT and EPA- accumulating Camelina: phosphatidyserine (PS) and phosphatidylglycerol (PG)

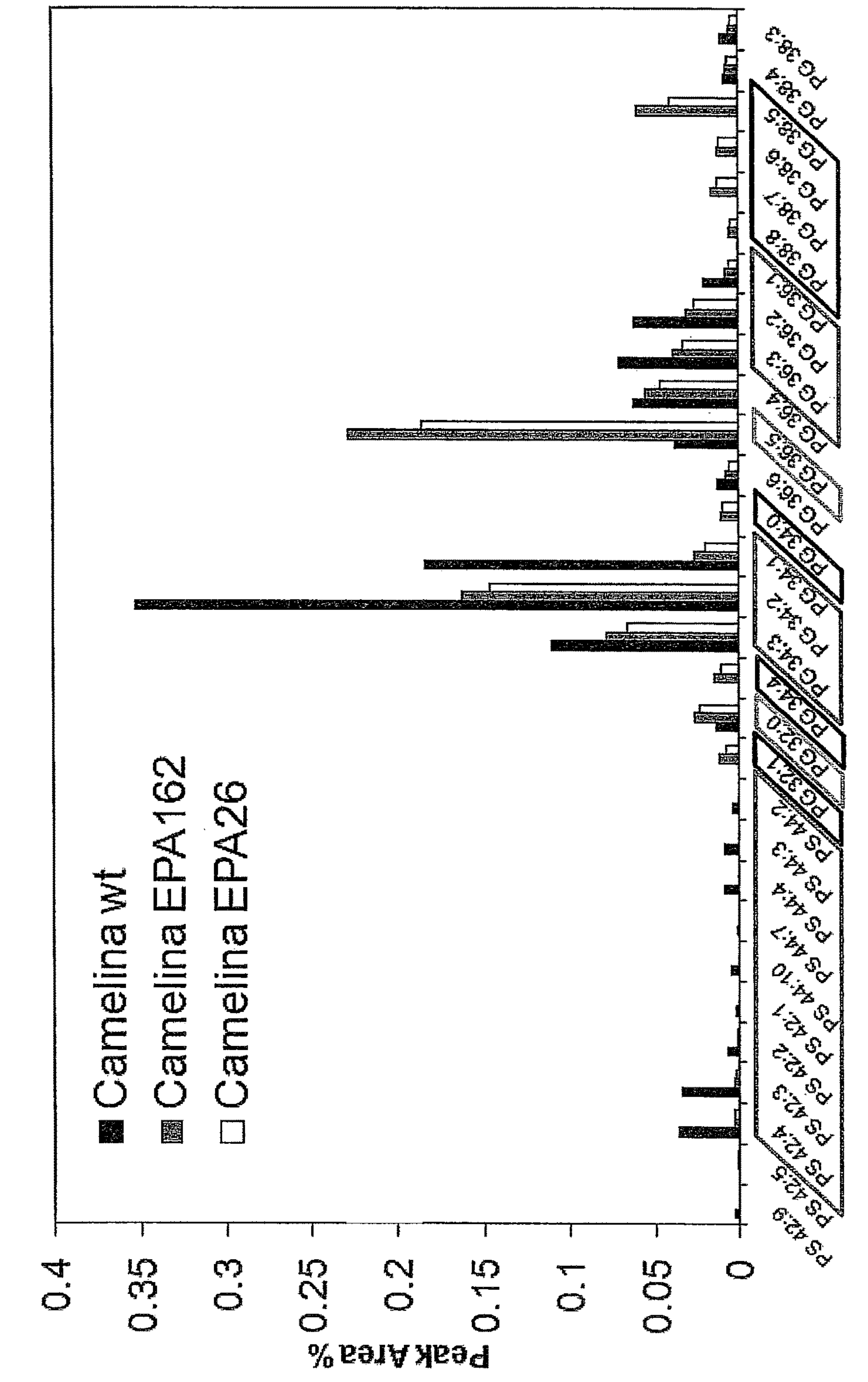

Novel species of PS or PG present in transgenic lines indicated with red boxes [classification based on total chain length for sn-1 and sn-2 positions, and number of double bonds] PS/PG species significantly reduced in transgenics are boxed in blue Fig 10. Analysis of Acyl CoA (LC - MS MS QTRAP) from Mid Development Arabidopsis & *Camelina* Seed
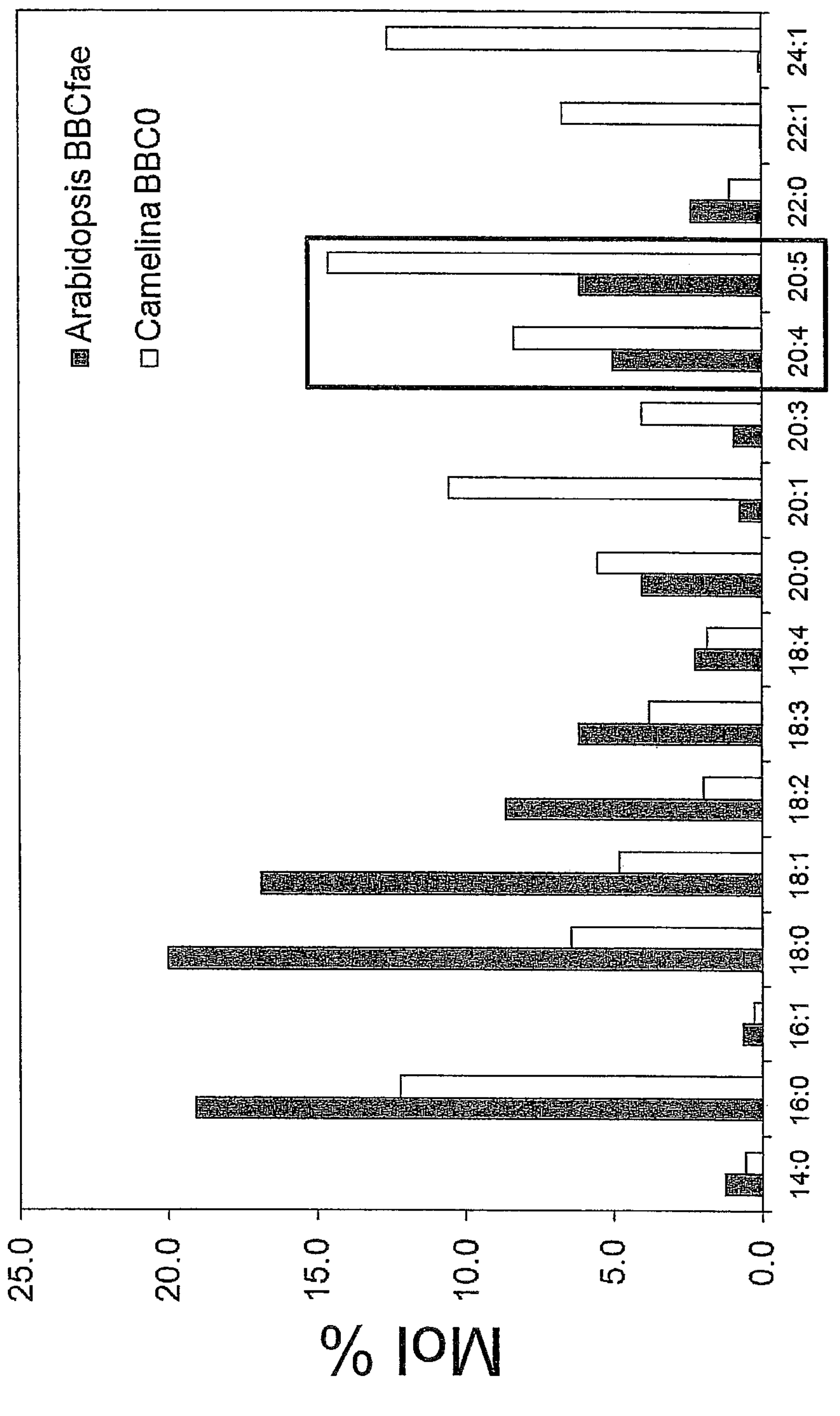

Fig 11: XIC of Acyl CoA MRM (26 pairs) *Camelina* Seed expressing MC (BBC0) construct
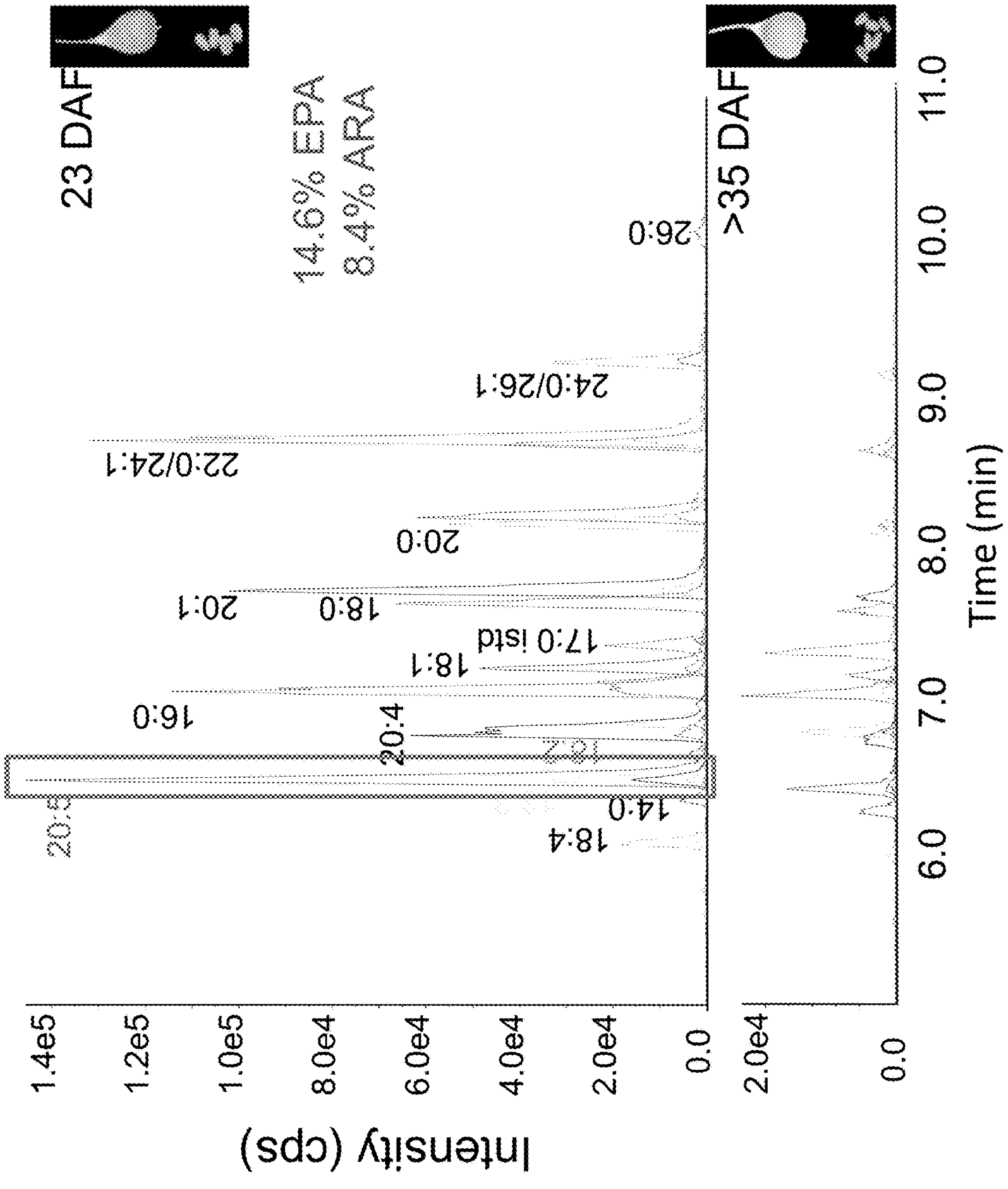

SEQUENCE LISTING

<160> NUMBER OF SEQ ID NOS: 28

<210> SEQ ID NO 1
<211> LENGTH: 1371
<212> TYPE: DNA
<213> ORGANISM: Ostreococcus tauri

<400> SEQUENCE: 1

```
atgtgtgttg agaccgagaa caacgatgga atccctactg tggagatcgc tttcgatgga     60

gagagagaaa gagctgaggc taacgtgaag ttgtctgctg agaagatgga acctgctgct    120

ttggctaaga ccttcgctag aagatacgtg gttatcgagg gagttgagta cgatgtgacc    180

gatttcaaac atcctggagg aaccgtgatt ttctacgctc tctctaacac tggagctgat    240

gctactgagg ctttcaagga gttccaccac agatctagaa aggctaggaa ggctttggct    300

gctttgcctt ctagacctgc taagaccgct aaagtggatg atgctgagat gctccaggat    360

ttcgctaagt ggagaaagga gttggagagg gacggattct tcaagccttc tcctgctcat    420

gttgcttaca gattcgctga gttggctgct atgtacgctt tgggaaccta cttgatgtac    480

gctagatacg ttgtgtcctc tgtgttggtt tacgcttgct tcttcggagc tagatgtgga    540

tgggttcaac atgagggagg acattcttct ttgaccggaa acatctggtg ggataagaga    600

atccaagctt tcactgctgg attcggattg gctggatctg gagatatgtg gaactccatg    660

cacaacaagc accatgctac tcctcaaaaa gtgaggcacg atatggattt ggataccact    720

cctgctgttg ctttcttcaa caccgctgtg gaggataata gacctagggg attctctaag    780

tactggctca gattgcaagc ttggaccttc attcctgtga cttctggatt ggtgttgctc    840

ttctggatgt tcttcctcca tccttctaag gctttgaagg gaggaaagta cgaggagctt    900

gtgtggatgt tggctgctca tgtgattaga acctggacca ttaaggctgt tactggattc    960

accgctatgc aatcctacgg actcttcttg gctacttctt gggtttccgg atgctacttg   1020
```

```
ttcgctcact tctctacttc tcacacccat ttggatgttg ttcctgctga tgagcatttg   1080

tcttgggtta ggtacgctgt ggatcacacc attgatatcg atccttctca gggatgggtt   1140

aactggttga tgggatactt gaactgccaa gtgattcatc acctcttccc ttctatgcct   1200

caattcagac aacctgaggt gtccagaaga ttcgttgctt tcgctaagaa gtggaacctc   1260

aactacaagg tgatgactta tgctggagct tggaaggcta ctttgggaaa cctcgataat   1320

gtgggaaagc actactacgt gcacggacaa cattctggaa agaccgcttg a            1371
```

```
<210> SEQ ID NO 2
<211> LENGTH: 456
<212> TYPE: PRT
<213> ORGANISM: Ostreococcus tauri

<400> SEQUENCE: 2

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
```

305 310 315 320

Thr Ala Met Gln Ser Tyr Gly Leu Phe Leu Ala Thr Ser Trp Val Ser
325 330 335

Gly Cys Tyr Leu Phe Ala His Phe Ser Thr Ser His Thr His Leu Asp
340 345 350

Val Val Pro Ala Asp Glu His Leu Ser Trp Val Arg Tyr Ala Val Asp
355 360 365

His Thr Ile Asp Ile Asp Pro Ser Gln Gly Trp Val Asn Trp Leu Met
370 375 380

Gly Tyr Leu Asn Cys Gln Val Ile His His Leu Phe Pro Ser Met Pro
385 390 395 400

Gln Phe Arg Gln Pro Glu Val Ser Arg Arg Phe Val Ala Phe Ala Lys
405 410 415

Lys Trp Asn Leu Asn Tyr Lys Val Met Thr Tyr Ala Gly Ala Trp Lys
420 425 430

Ala Thr Leu Gly Asn Leu Asp Asn Val Gly Lys His Tyr Tyr Val His
435 440 445

Gly Gln His Ser Gly Lys Thr Ala
450 455

<210> SEQ ID NO 3
<211> LENGTH: 873
<212> TYPE: DNA
<213> ORGANISM: Physcomitrella patens

<400> SEQUENCE: 3
atggaagttg ttgagaggtt ctacggagag ttggatggaa aggtttccca aggagtgaac 60
gctttgttgg gatctttcgg agttgagttg actgataccc caactactaa gggattgcca 120
ctcgttgatt ctccaactcc aattgtgttg ggagtgtctg tttacttgac catcgtgatc 180
ggaggattgc tttggatcaa ggctagagat ctcaagccaa gagcttctga gccattcttg 240
ttgcaagctt tggtgttggt gcacaacttg ttctgcttcg ctttgtctct ttacatgtgc 300
gtgggtatcg cttaccaagc tatcacctgg agatattcct tgtggggaaa cgcttataac 360
ccaaagcaca aggagatggc tatcctcgtt tacctcttct acatgtccaa gtacgtggag 420
ttcatggata ccgtgatcat gatcctcaag agatccacca gacagatttc tttcctccac 480
gtgtaccacc attcttctat ctcccttatc tggtgggcta ttgctcatca tgctccagga 540
ggagaggctt attggagtgc tgctctcaac tctggagtgc atgtgttgat gtacgcttac 600
tacttcttgg ctgcttgctt gagatcttcc ccaaagctca agaacaagta cctcttctgg 660
ggaagatacc tcacccaatt ccagatgttc cagttcatgc tcaacttggt gcaagcttac 720
tacgatatga aaaccaacgc tccatatcca caatggctca tcaagatcct cttctactac 780
atgatctccc tcttgttcct cttcggaaac ttctacgtgc aaaagtacat caagccatcc 840
gatggaaagc aaaagggagc taagaccgag tga 873

<210> SEQ ID NO 4
<211> LENGTH: 290
<212> TYPE: PRT
<213> ORGANISM: Thraustochytrium sp.

<400> SEQUENCE: 4

Met Glu Val Val Glu Arg Phe Tyr Gly Glu Leu Asp Gly Lys Val Ser
1 5 10 15

Gln Gly Val Asn Ala Leu Leu Gly Ser Phe Gly Val Glu Leu Thr Asp

```
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290


<210> SEQ ID NO 5
<211> LENGTH: 1320
<212> TYPE: DNA
<213> ORGANISM: Thraustochytrium sp.

<400> SEQUENCE: 5

atgggaaaag gatctgaggg aagatctgct gctagagaga tgactgctga ggctaacgga      60

gataagagaa agaccatcct cattgaggga gtgttgtacg atgctaccaa cttcaaacac     120

ccaggaggtt ccattattaa cttcctcacc gagggagaag ctggagttga tgctacccaa     180

gcttacagag agttccatca gagatccgga aaggctgata agtacctcaa gtccctccca     240

aagttggatg cttctaaggt ggagtctagg ttctctgcta aggagcaggc tagaagggac     300

gctatgacca gggattacgc tgctttcaga gaggagttgg ttgctgaggg atacttcgat     360

ccatctatcc cacacatgat ctacagagtg gtggagattg tggctttgtt cgctttgtct     420

ttctggttga tgtctaaggc ttctccaacc tctttggttt tgggagtggt gatgaacgga     480

atcgctcaag gaagatgcgg atgggttatg catgagatgg gacacggatc tttcactgga     540
```

```
gttatctggc tcgatgatag gatgtgcgag ttcttctacg gagttggatg tggaatgtct    600

ggacactact ggaagaacca gcattctaag caccatgctg ctccaaacag attggagcac    660

gatgtggatt tgaacacctt gccactcgtt gctttcaacg agagagttgt gaggaaggtt    720

aagccaggat ctttgttggc tttgtggctc agagttcagg cttatttgtt cgctccagtg    780

tcttgcttgt tgatcggatt gggatggacc ttgtacttgc acccaagata tatgctcagg    840

accaagagac atatggagtt tgtgtggatc ttcgctagat atatcggatg gttctccttg    900

atgggagctt tgggatattc tcctggaact tctgtgggaa tgtacctctg ctctttcgga    960

cttggatgca tctacatctt cctccaattc gctgtgtctc atacccattt gccagttacc   1020

aacccagagg atcaattgca ttggcttgag tacgctgctg atcataccgt gaacatctct   1080

accaagtctt ggttggttac ctggtggatg tctaacctca acttccaaat cgagcatcat   1140

ttgttcccaa ccgctccaca attcaggttc aaggagatct ctccaagagt tgaggctctc   1200

ttcaagagac ataacctccc ttactacgat ttgccataca cctctgctgt ttctactacc   1260

ttcgctaacc tctactctgt tggacattct gttggagctg ataccaagaa gcaggattga   1320


<210> SEQ ID NO 6
<211> LENGTH: 439
<212> TYPE: PRT
<213> ORGANISM: Thraustochytrium sp.

<400> SEQUENCE: 6

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240
```

```
Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435
```

```
<210> SEQ ID NO 7
<211> LENGTH: 903
<212> TYPE: DNA
<213> ORGANISM: Ostreococcus tauri

<400> SEQUENCE: 7

atgtctgctt ctggagcttt gttgcctgct attgctttcg ctgcttacgc ttacgctacc     60

tacgcttatg ctttcgagtg gtctcatgct aacggaatcg ataacgtgga tgctagagag    120

tggattggag ctttgtcttt gagactccct gcaattgcta ccaccatgta cctcttgttc    180

tgccttgtgg gacctagatt gatggctaag agggaggctt ttgatcctaa gggattcatg    240

ctcgcttaca acgcttacca aaccgctttc aacgttgtgg tgctcggaat gttcgctaga    300

gagatctctg gattgggaca acctgtttgg ggatctacta tgccttggag cgataggaag    360

tccttcaaga ttttgttggg agtgtggctc cattacaaca ataagtacct cgagttgttg    420

gatactgtgt tcatggtggc taggaaaaag accaagcagc tctctttctt gcatgtgtac    480

catcatgctt tgttgatttg ggcttggtgg cttgtttgtc atctcatggc taccaacgat    540

tgcatcgatg cttatttcgg agctgcttgc aactctttca tccacatcgt gatgtactcc    600

tactacctca tgtctgcttt gggaattaga tgcccttgga agagatatat cacccaggct    660

cagatgttgc aattcgtgat cgtgttcgct catgctgttt tcgtgctcag acaaaagcac    720

tgccctgtta ctttgccttg ggcacaaatg ttcgtgatga caaatatgtt ggtgctcttc    780

ggaaacttct acctcaaggc ttactctaac aagtctaggg gagatggagc ttcttctgtt    840

aagcctgctg agactactag agcaccttct gtgagaagaa ccaggtccag gaagatcgat    900

tga                                                                  903
```

<210> SEQ ID NO 8
<211> LENGTH: 300
<212> TYPE: PRT
<213> ORGANISM: Ostreococcus tauri

<400> SEQUENCE: 8

Met Ser Ala Ser Gly Ala Leu Leu Pro Ala Ile Ala Phe Ala Ala Tyr
1 5 10 15

Ala Tyr Ala Thr Tyr Ala Tyr Ala Phe Glu Trp Ser His Ala Asn Gly
20 25 30

Ile Asp Asn Val Asp Ala Arg Glu Trp Ile Gly Ala Leu Ser Leu Arg
35 40 45

Leu Pro Ala Ile Ala Thr Thr Met Tyr Leu Leu Phe Cys Leu Val Gly
50 55 60

Pro Arg Leu Met Ala Lys Arg Glu Ala Phe Asp Pro Lys Gly Phe Met
65 70 75 80

Leu Ala Tyr Asn Ala Tyr Gln Thr Ala Phe Asn Val Val Val Leu Gly
85 90 95

Met Phe Ala Arg Glu Ile Ser Gly Leu Gly Gln Pro Val Trp Gly Ser
100 105 110

Thr Met Pro Trp Ser Asp Arg Lys Ser Phe Lys Ile Leu Leu Gly Val
115 120 125

Trp Leu His Tyr Asn Asn Lys Tyr Leu Glu Leu Leu Asp Thr Val Phe
130 135 140

Met Val Ala Arg Lys Lys Thr Lys Gln Leu Ser Phe Leu His Val Tyr
145 150 155 160

His His Ala Leu Leu Ile Trp Ala Trp Trp Leu Val Cys His Leu Met
165 170 175

Ala Thr Asn Asp Cys Ile Asp Ala Tyr Phe Gly Ala Ala Cys Asn Ser
180 185 190

Phe Ile His Ile Val Met Tyr Ser Tyr Tyr Leu Met Ser Ala Leu Gly
195 200 205

Ile Arg Cys Pro Trp Lys Arg Tyr Ile Thr Gln Ala Gln Met Leu Gln
210 215 220

Phe Val Ile Val Phe Ala His Ala Val Phe Val Leu Arg Gln Lys His
225 230 235 240

Cys Pro Val Thr Leu Pro Trp Ala Gln Met Phe Val Met Thr Asn Met
245 250 255

Leu Val Leu Phe Gly Asn Phe Tyr Leu Lys Ala Tyr Ser Asn Lys Ser
260 265 270

Arg Gly Asp Gly Ala Ser Ser Val Lys Pro Ala Glu Thr Thr Arg Ala
275 280 285

Pro Ser Val Arg Arg Thr Arg Ser Arg Lys Ile Asp
290 295 300

<210> SEQ ID NO 9
<211> LENGTH: 1368
<212> TYPE: DNA
<213> ORGANISM: Emiliana huxleyz

<400> SEQUENCE: 9
atgtcattgg ctgctaaaga tgcagcctcg gcccactcat ccgtcttgga ccctaagtat 60
cacggagcta caaataagtc aagaactgat gcagcagacc ttacagttag ttctatcgac 120
acttctaagg agatgatcat aaggggtcgt gtgtatgatg tctctgattt tattaaaagg 180

```
cacccgggag gaagcattat taaactctcc ttaggttctg atgcaacaga cgcttataac    240

aacttccata ttaggtctaa aaaagcggat aaaatgttga gagctttgcc aagtaggcca    300

gtagcggatg gattcgctag agacgctttg tctgcagact tcgaggccct gagagcccaa    360

ctcgaggccg aaggttactt cgaaccgaat ctgtggcatg tagcttatcg agttgcggaa    420

gtcgttgcta tgtactgggc gggtattaga cttatctggg cgggttattg gtttttagga    480

gccattgtag caggaatagc tcaggggaga tgcggttggc ttcagcatga gggtggtcat    540

tattcgctca caggtaatat taaacttgat cgacacatgc aaatgattat ctatggatta    600

ggttgcggaa tgtccggttg ttattggaga aaccaacata acaagcacca tgcgacaccg    660

caaaagttgg gtgcagatcc agaccttcaa acaatgcctc tggttgcgtt ccatggactc    720

atcggtgcta aggctagggg agcaggaaag tcgtggctag catggcaagc tccacttttc    780

tttggaggcg ttatcacaac cctggtatct tttggttggc agttcgtcca acatccaaag    840

cacgcattga gagtaggaaa ccaactcgaa ttaggctata tggctttacg atatgcttta    900

tggtatgcag cattcggtca tcttgggctt ggtggtgctt tcagattgta cgctttttat    960

gtggcagtcg gaggtacata tatcttcacg aactttgcgg tgtctcacac acataaggat   1020

gttgttccac acgataagca tatttcttgg accttgtatt ctgcaaacca taccactaat   1080

caatctaaca cacctctagt caattggtgg atggcctatc tgaattttca aattgaacat   1140

caccttttcc ctagcatgcc acaatataac catcctaaaa tctgcggaag agtgaaacaa   1200

ttgtttgaaa aacatggcgt agagtacgat gtcagaactt acgcgaagtc aatgcgtgat   1260

acatacgtga atctcttggc tgtgggaaat gcatctcatt cccttcatca gagaaacgag   1320

ggattaacga ctagggagtc tgcggctgtt agagttacag gtcattga                1368
```

```
<210> SEQ ID NO 10
<211> LENGTH: 455
<212> TYPE: PRT
<213> ORGANISM: Emiliana huxleyz

<400> SEQUENCE: 10

Met Ser Leu Ala Ala Lys Asp Ala Ala Ser Ala His Ser Ser Val Leu
1               5                   10                  15

Asp Pro Lys Tyr His Gly Ala Thr Asn Lys Ser Arg Thr Asp Ala Ala
            20                  25                  30

Asp Leu Thr Val Ser Ser Ile Asp Thr Ser Lys Glu Met Ile Ile Arg
        35                  40                  45

Gly Arg Val Tyr Asp Val Ser Asp Phe Ile Lys Arg His Pro Gly Gly
    50                  55                  60

Ser Ile Ile Lys Leu Ser Leu Gly Ser Asp Ala Thr Asp Ala Tyr Asn
65                  70                  75                  80

Asn Phe His Ile Arg Ser Lys Lys Ala Asp Lys Met Leu Arg Ala Leu
                85                  90                  95

Pro Ser Arg Pro Val Ala Asp Gly Phe Ala Arg Asp Ala Leu Ser Ala
            100                 105                 110

Asp Phe Glu Ala Leu Arg Ala Gln Leu Glu Ala Glu Gly Tyr Phe Glu
        115                 120                 125

Pro Asn Leu Trp His Val Ala Tyr Arg Val Ala Glu Val Val Ala Met
    130                 135                 140

Tyr Trp Ala Gly Ile Arg Leu Ile Trp Ala Gly Tyr Trp Phe Leu Gly
145                 150                 155                 160

Ala Ile Val Ala Gly Ile Ala Gln Gly Arg Cys Gly Trp Leu Gln His
```

```
                165                 170                 175

Glu Gly Gly His Tyr Ser Leu Thr Gly Asn Ile Lys Leu Asp Arg His
            180                 185                 190

Met Gln Met Ile Ile Tyr Gly Leu Gly Cys Gly Met Ser Gly Cys Tyr
        195                 200                 205

Trp Arg Asn Gln His Asn Lys His His Ala Thr Pro Gln Lys Leu Gly
    210                 215                 220

Ala Asp Pro Asp Leu Gln Thr Met Pro Leu Val Ala Phe His Gly Leu
225                 230                 235                 240

Ile Gly Ala Lys Ala Arg Gly Ala Gly Lys Ser Trp Leu Ala Trp Gln
                245                 250                 255

Ala Pro Leu Phe Phe Gly Gly Val Ile Thr Thr Leu Val Ser Phe Gly
            260                 265                 270

Trp Gln Phe Val Gln His Pro Lys His Ala Leu Arg Val Gly Asn Gln
        275                 280                 285

Leu Glu Leu Gly Tyr Met Ala Leu Arg Tyr Ala Leu Trp Tyr Ala Ala
    290                 295                 300

Phe Gly His Leu Gly Leu Gly Gly Ala Phe Arg Leu Tyr Ala Phe Tyr
305                 310                 315                 320

Val Ala Val Gly Gly Thr Tyr Ile Phe Thr Asn Phe Ala Val Ser His
                325                 330                 335

Thr His Lys Asp Val Val Pro His Asp Lys His Ile Ser Trp Thr Leu
            340                 345                 350

Tyr Ser Ala Asn His Thr Thr Asn Gln Ser Asn Thr Pro Leu Val Asn
        355                 360                 365

Trp Trp Met Ala Tyr Leu Asn Phe Gln Ile Glu His His Leu Phe Pro
    370                 375                 380

Ser Met Pro Gln Tyr Asn His Pro Lys Ile Cys Gly Arg Val Lys Gln
385                 390                 395                 400

Leu Phe Glu Lys His Gly Val Glu Tyr Asp Val Arg Thr Tyr Ala Lys
                405                 410                 415

Ser Met Arg Asp Thr Tyr Val Asn Leu Leu Ala Val Gly Asn Ala Ser
            420                 425                 430

His Ser Leu His Gln Arg Asn Glu Gly Leu Thr Thr Arg Glu Ser Ala
        435                 440                 445

Ala Val Arg Val Thr Gly His
    450                 455
```

<210> SEQ ID NO 11
<211> LENGTH: 1197
<212> TYPE: DNA
<213> ORGANISM: Phytophthora sojae

<400> SEQUENCE: 11

```
atggctattt tgaaccctga ggctgattct gctgctaacc tcgctactga ttctgaggct      60

aagcaaagac aattggctga ggctggatac actcatgttg agggtgctcc tgctcctttg     120

cctttggagt tgcctcattt ctctctcaga gatctcagag ctgctattcc taagcactgc     180

ttcgagagat ctttcgtgac ctccacctac tacatgatca agaacgtgtt gacttgcgct     240

gctttgttct acgctgctac cttcattgat agagctggag ctgctgctta tgttttgtgg     300

cctgtgtact ggttcttcca gggatcttac ttgactggag tgtgggttat cgctcatgag     360

tgtggacatc aggcttattg ctcttctgag gtggtgaaca acttgattgg actcgtgttg     420

cattctgctt tgttggtgcc ttaccactct tggagaatct ctcacagaaa gcaccattcc     480
```

aacactggat cttgcgagaa cgatgaggtt ttcgttcctg tgaccagatc tgtgttggct 540
tcttcttgga acgagacctt ggaggattct cctctctacc aactctaccg tatcgtgtac 600
atgttggttg ttggatggat gcctggatac ctcttcttca acgctactgg acctactaag 660
tactggggaa agtctaggtc tcacttcaac ccttactccg ctatctatgc tgatagggag 720
agatggatga tcgtgctctc cgatattttc ttggtggcta tgttggctgt tttggctgct 780
ttggtgcaca ctttctcctt caacaccatg gtgaagttct acgtggtgcc ttacttcatt 840
gtgaacgctt acttggtgtt gattacctac ctccaacaca ccgatactta catccctcat 900
ttcagagagg gagagtggaa ttggttgaga ggagctttgt gcactgtgga tagatcattt 960
ggtccattcc tcgattctgt ggtgcataga atcgtggata cccatgtttg ccaccacatc 1020
ttctccaaga tgcctttcta tcattgcgag gaggctacca acgctattaa gcctctcctc 1080
ggaaagttct acttgaagga taccactcct gttcctgttg ctctctggag atcttacacc 1140
cattgcaagt tcgttgagga tgatggaaag gtggtgttct acaagaacaa gctctag 1197

<210> SEQ ID NO 12
<211> LENGTH: 398
<212> TYPE: PRT
<213> ORGANISM: Phytophthora sojae

<400> SEQUENCE: 12

Met Ala Ile Leu Asn Pro Glu Ala Asp Ser Ala Ala Asn Leu Ala Thr
1 5 10 15

Asp Ser Glu Ala Lys Gln Arg Gln Leu Ala Glu Ala Gly Tyr Thr His
20 25 30

Val Glu Gly Ala Pro Ala Pro Leu Pro Leu Glu Leu Pro His Phe Ser
35 40 45

Leu Arg Asp Leu Arg Ala Ala Ile Pro Lys His Cys Phe Glu Arg Ser
50 55 60

Phe Val Thr Ser Thr Tyr Tyr Met Ile Lys Asn Val Leu Thr Cys Ala
65 70 75 80

Ala Leu Phe Tyr Ala Ala Thr Phe Ile Asp Arg Ala Gly Ala Ala Ala
85 90 95

Tyr Val Leu Trp Pro Val Tyr Trp Phe Phe Gln Gly Ser Tyr Leu Thr
100 105 110

Gly Val Trp Val Ile Ala His Glu Cys Gly His Gln Ala Tyr Cys Ser
115 120 125

Ser Glu Val Val Asn Asn Leu Ile Gly Leu Val Leu His Ser Ala Leu
130 135 140

Leu Val Pro Tyr His Ser Trp Arg Ile Ser His Arg Lys His His Ser
145 150 155 160

Asn Thr Gly Ser Cys Glu Asn Asp Glu Val Phe Val Pro Val Thr Arg
165 170 175

Ser Val Leu Ala Ser Ser Trp Asn Glu Thr Leu Glu Asp Ser Pro Leu
180 185 190

Tyr Gln Leu Tyr Arg Ile Val Tyr Met Leu Val Val Gly Trp Met Pro
195 200 205

Gly Tyr Leu Phe Phe Asn Ala Thr Gly Pro Thr Lys Tyr Trp Gly Lys
210 215 220

Ser Arg Ser His Phe Asn Pro Tyr Ser Ala Ile Tyr Ala Asp Arg Glu
225 230 235 240

Arg Trp Met Ile Val Leu Ser Asp Ile Phe Leu Val Ala Met Leu Ala

```
                245                 250                 255

Val Leu Ala Ala Leu Val His Thr Phe Ser Phe Asn Thr Met Val Lys
            260                 265                 270

Phe Tyr Val Val Pro Tyr Phe Ile Val Asn Ala Tyr Leu Val Leu Ile
        275                 280                 285

Thr Tyr Leu Gln His Thr Asp Thr Tyr Ile Pro His Phe Arg Glu Gly
    290                 295                 300

Glu Trp Asn Trp Leu Arg Gly Ala Leu Cys Thr Val Asp Arg Ser Phe
305                 310                 315                 320

Gly Pro Phe Leu Asp Ser Val Val His Arg Ile Val Asp Thr His Val
                325                 330                 335

Cys His His Ile Phe Ser Lys Met Pro Phe Tyr His Cys Glu Glu Ala
            340                 345                 350

Thr Asn Ala Ile Lys Pro Leu Leu Gly Lys Phe Tyr Leu Lys Asp Thr
        355                 360                 365

Thr Pro Val Pro Val Ala Leu Trp Arg Ser Tyr Thr His Cys Lys Phe
    370                 375                 380

Val Glu Asp Asp Gly Lys Val Val Phe Tyr Lys Asn Lys Leu
385                 390                 395


<210> SEQ ID NO 13
<211> LENGTH: 1084
<212> TYPE: DNA
<213> ORGANISM: Phytophthora infestans

<400> SEQUENCE: 13

atggctacaa aggaggctta cgttttccca actctcaccg agatcaagag atctctccca      60

aaggattgct tcgaggcttc tgtgcctttg tctctctact acactgtgag atgcttggtt     120

attgctgtgg ctttgacctt cggattgaac tacgctagag ctttgccaga ggttgagtct     180

ttctgggctt tggatgctgc tttgtgcact ggatatatcc tcctccaggg aattgtgttc     240

tggggattct tcactgttgg acacgatgct ggacacggag ctttctctag ataccacctc     300

ttgacttcgt tgtgggacct tcatgcactc tctcatcttg accccattcg agtcttggaa     360

gttgacccac agacaccacc acaagaacac cggaaacatc gatagagatg aggtgttcta     420

cccacagaga aaggctgatg atcacccatt gtccaggaac ttgatcttgg ctttgggagc     480

tgcttggctt gcttatttgg tggagggatt cccaccaaga aaggtgaacc acttcaaccc     540

attcgagcca ctttttgtga gacaagtgtc cgctgtggtt atctctttgc tcgctcactt     600

cttcgttgct ggactctcta tctacttgtc tctccagttg ggacttaaga ccatggctat     660

ctactactac ggaccagttt tcgtgttcgg atctatgttg gtgattacca ccttcttgca     720

ccacaacgat gaggagactc catggtatgc tgattctgag tggacttacg tgaagggaaa     780

cttgtcctct gtggatagat cttacggtgc tctcatcgat aacctctccc acaacatcgg     840

aactcaccag atccaccacc tcttcccaat tatcccacac tacaagctca agaaggctac     900

tgctgctttc caccaagctt tcccagagct tgtgagaaag tccgatgagc caatcatcaa     960

ggctttcttc agagtgggaa ggttgtatgc taactacgga gtggttgatc aagaggctaa    1020

gctcttcact ttgaaggagg ctaaggctgc tactgaagct gctgctaaga ccaagtctac    1080

ctga                                                                 1084


<210> SEQ ID NO 14
<211> LENGTH: 361
<212> TYPE: PRT
```

<213> ORGANISM: Phytophthora infestans

<400> SEQUENCE: 14

```
Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
        355                 360
```

<210> SEQ ID NO 15
<211> LENGTH: 1380
<212> TYPE: DNA
<213> ORGANISM: Emiliana huxleyi

<400> SEQUENCE: 15

```
atggggggtg caggcgcttc ggaagcagag aggccaaagt ggacaactat ccacggaaga     60
cacgttgatg tgtcaaagtt tagacaccct ggaggtaata tcattgaatt gttctatggc    120
atggatagta catccgcttt cgagcaattt cacggacatc ataagggggc atggaagatg    180
ctcaaggctc ttcctaccaa ggaggttgac ccagctgacg tcccacagca acctcaagaa    240
catgtcgcgg agatgaccag acttatgaca tcctggagag aaaggggttt attcaagcct    300
cgtccggttg catctggcat atatggactt gcagtagttg ctgctatagt tgcatgcatt    360
gcatgtgctc cgcacgcacc ggttctgtcg gggattggtt tagggtcttg ttgggcccaa    420
tgcggtttct tgcagcatat gggggacat agggagtggg gggtcaggta ttctttcttg    480
ctccaacact tctttgaggg tttactaaag ggaggatcag ctagctggtg gaggaacaga    540
cataataagc atcatgcgaa aaccaatgtt cttggagagg atggtgacct tcgaactact    600
ccattctttg cgtgggaccc gactctcgct aaaaaggtgc cggattggtc tctgaagaca    660
caagctttca ctttcctccc agcactagga gcctatgttt tcgttttcgc tttcacaatt    720
agaaaatacg ctgtggtgaa aaaactctgg cacgaacttg ctctaatgat tgctcattac    780
gcaatgttct actatgccct gcagttggct ggagccagtt tgggttctgg acttgcattt    840
tactgcacag gttacgcatg gcagggaatc tacctcggat tcttcttcgg tttgagccac    900
tttgcagtcg agagagtacc aagcacagcg acatggctcg aaagctcaat gataggttca    960
tggcagggaa tctacctcgg attcttcttc ggtttgagcc actttgcagt cgagagagta   1020
ccaagcacag cgacatggct cgaaagctca atgataggta cggtagactg gggaggttca   1080
tctgcttttt gtggttatgt ttctggtttc ttgaatatcc aaattgaaca tcacatggcc   1140
cctcaaatgc ctatggaaaa tctgagacag atcagggcag attgtaaggc tagtgctgag   1200
aaactcggct tgccatatag agagttgtca ttcgcaggtg ctgtcaaact catgatggta   1260
ggtctctgga ggactggaag agacgaatta cagctccgaa gtgatcgaag aaagtactca   1320
agaacccagg cttacatggc ggctgcttca gctgttgttg aaaatctgaa ggcagattaa   1380
```

<210> SEQ ID NO 16
<211> LENGTH: 459
<212> TYPE: PRT
<213> ORGANISM: Emiliana huxleyi

<400> SEQUENCE: 16

```
Met Gly Gly Ala Gly Ala Ser Glu Ala Glu Arg Pro Lys Trp Thr Thr
1               5                   10                  15

Ile His Gly Arg His Val Asp Val Ser Lys Phe Arg His Pro Gly Gly
            20                  25                  30

Asn Ile Ile Glu Leu Phe Tyr Gly Met Asp Ser Thr Ser Ala Phe Glu
        35                  40                  45

Gln Phe His Gly His His Lys Gly Ala Trp Lys Met Leu Lys Ala Leu
    50                  55                  60

Pro Thr Lys Glu Val Asp Pro Ala Asp Val Pro Gln Gln Pro Gln Glu
65                  70                  75                  80

His Val Ala Glu Met Thr Arg Leu Met Thr Ser Trp Arg Glu Arg Gly
                85                  90                  95

Leu Phe Lys Pro Arg Pro Val Ala Ser Gly Ile Tyr Gly Leu Ala Val
            100                 105                 110

Val Ala Ala Ile Val Ala Cys Ile Ala Cys Ala Pro His Ala Pro Val
        115                 120                 125
```

```
Leu Ser Gly Ile Gly Leu Gly Ser Cys Trp Ala Gln Cys Gly Phe Leu
    130                 135                 140

Gln His Met Gly Gly His Arg Glu Trp Gly Val Arg Tyr Ser Phe Leu
145                 150                 155                 160

Leu Gln His Phe Phe Glu Gly Leu Leu Lys Gly Gly Ser Ala Ser Trp
                165                 170                 175

Trp Arg Asn Arg His Asn Lys His His Ala Lys Thr Asn Val Leu Gly
            180                 185                 190

Glu Asp Gly Asp Leu Arg Thr Thr Pro Phe Phe Ala Trp Asp Pro Thr
        195                 200                 205

Leu Ala Lys Lys Val Pro Asp Trp Ser Leu Lys Thr Gln Ala Phe Thr
    210                 215                 220

Phe Leu Pro Ala Leu Gly Ala Tyr Val Phe Val Phe Ala Phe Thr Ile
225                 230                 235                 240

Arg Lys Tyr Ala Val Val Lys Lys Leu Trp His Glu Leu Ala Leu Met
                245                 250                 255

Ile Ala His Tyr Ala Met Phe Tyr Tyr Ala Leu Gln Leu Ala Gly Ala
            260                 265                 270

Ser Leu Gly Ser Gly Leu Ala Phe Tyr Cys Thr Gly Tyr Ala Trp Gln
        275                 280                 285

Gly Ile Tyr Leu Gly Phe Phe Phe Gly Leu Ser His Phe Ala Val Glu
    290                 295                 300

Arg Val Pro Ser Thr Ala Thr Trp Leu Glu Ser Ser Met Ile Gly Ser
305                 310                 315                 320

Trp Gln Gly Ile Tyr Leu Gly Phe Phe Phe Gly Leu Ser His Phe Ala
                325                 330                 335

Val Glu Arg Val Pro Ser Thr Ala Thr Trp Leu Glu Ser Ser Met Ile
            340                 345                 350

Gly Thr Val Asp Trp Gly Gly Ser Ser Ala Phe Cys Gly Tyr Val Ser
        355                 360                 365

Gly Phe Leu Asn Ile Gln Ile Glu His His Met Ala Pro Gln Met Pro
    370                 375                 380

Met Glu Asn Leu Arg Gln Ile Arg Ala Asp Cys Lys Ala Ser Ala Glu
385                 390                 395                 400

Lys Leu Gly Leu Pro Tyr Arg Glu Leu Ser Phe Ala Gly Ala Val Lys
                405                 410                 415

Leu Met Met Val Gly Leu Trp Arg Thr Gly Arg Asp Glu Leu Gln Leu
            420                 425                 430

Arg Ser Asp Arg Arg Lys Tyr Ser Arg Thr Gln Ala Tyr Met Ala Ala
        435                 440                 445

Ala Ser Ala Val Val Glu Asn Leu Lys Ala Asp
    450                 455
```

<210> SEQ ID NO 17
<211> LENGTH: 1560
<212> TYPE: DNA
<213> ORGANISM: Thraustochytrium sp., ATCC21685

<400> SEQUENCE: 17

```
atgactgttg gatacgatga ggagatccca ttcgagcaag ttagggctca taacaagcca      60

gatgatgctt ggtgtgctat tcatggacac gtgtacgatg ttaccaagtt cgcttctgtt     120

catccaggag gagatattat cttgctcgct gctggaaagg aagctactgt gctctacgag     180

acctaccatg ttagaggagt gtctgatgct gtgctcagaa agtacagaat cggaaagttg     240
```

```
ccagatggac aaggaggagc taacgagaag gagaagagaa ccttgtctgg attgtcctct    300

gcttcttact acacctggaa ctccgatttc tacagagtga tgagggagag agttgtggct    360

agattgaagg agagaggaaa ggctagaaga ggaggatacg agttgtggat caaggctttc    420

ttgctccttg ttggattctg gtcctctctt tactggatgt gcaccctcga tccatctttc    480

ggagctatct tggctgctat gtctttggga gtgttcgctg cttttgttgg aacctgcatc    540

caacatgatg gaaaccatgg agctttcgct caatctagat gggttaacaa ggtggcagga    600

tggactttgg atatgatcgg agcttctgga atgacttggg agttccaaca tgtgttggga    660

catcacccat acactaactt gatcgaggag gagaacggat tgcaaaaggt gtccggaaag    720

aagatggata ccaagttggc tgatcaagag tctgatccag atgtgttctc cacctaccca    780

atgatgagat tgcatccatg gcatcagaag agatggtatc acaggttcca gcatatctac    840

ggaccattca tcttcggatt catgaccatc aacaaggtgg tgactcaaga tgttggagtg    900

gtgttgagaa agaggctctt ccaaatcgat gctgagtgca gatatgcttc cccaatgtac    960

gttgctaggt tctggatcat gaaggctttg accgtgttgt acatggttgc tctcccatgt   1020

tatatgcaag gaccatggca tggattgaag ctcttcgcta tcgctcattt cacttgcgga   1080

gaggttttgg ctaccatgtt catcgtgaac cacattatcg agggagtgtc ttacgcttct   1140

aaggatgctg ttaagggaac tatggctcca ccaaagacta tgcatggagt gaccccaatg   1200

aacaacacta gaaaggaggt tgaggctgag gcttctaagt ctggagctgt ggttaagtct   1260

gtgccattgg atgattgggc tgctgttcaa tgccaaacct ctgtgaactg gtctgttgga   1320

tcttggttct ggaaccattt ctctggagga ctcaaccatc aaatcgagca tcatctcttc   1380

ccaggattgt ctcacgagac ctactaccac atccaagatg tggttcaatc tacctgtgct   1440

gagtacggag ttccatacca acatgagcca tctttgtgga ctgcttactg gaagatgctc   1500

gaacatttga gacaattggg aaacgaggag actcacgagt cttggcaaag agctgcttga   1560
```

<210> SEQ ID NO 18
<211> LENGTH: 519
<212> TYPE: PRT
<213> ORGANISM: Thraustochytrium sp., ATCC21685

<400> SEQUENCE: 18

```
Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
        115                 120                 125

Arg Arg Gly Gly Tyr Glu Leu Trp Ile Lys Ala Phe Leu Leu Leu Val
    130                 135                 140
```

```
Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
    210                 215                 220

Thr Asn Leu Ile Glu Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
    290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
        355                 360                 365

Val Asn His Ile Ile Glu Gly Val Ser Tyr Ala Ser Lys Asp Ala Val
    370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ala Ser Lys Ser Gly Ala
                405                 410                 415

Val Val Lys Ser Val Pro Leu Asp Asp Trp Ala Ala Val Gln Cys Gln
            420                 425                 430

Thr Ser Val Asn Trp Ser Val Gly Ser Trp Phe Trp Asn His Phe Ser
        435                 440                 445

Gly Gly Leu Asn His Gln Ile Glu His His Leu Phe Pro Gly Leu Ser
    450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
        515
```

<210> SEQ ID NO 19
<211> LENGTH: 1320
<212> TYPE: DNA
<213> ORGANISM: Ostreococcus RCC809

<400> SEQUENCE: 19

```
atgggaaagg gagcaaggaa cccaggagca agggcatgga agtcaacatt ggagcctcac     60
gcagtggcaa agtcattcga taggagatgg gttaaggtgg atggagttga atacgatgtg    120
actgatttca agcatcctgg aggtagtgtt atatactaca tgctttctaa cacaggtgct    180
gatgcaaccg aagcttttaa ggagttccat tacaggagta agaaagctag gaaagcactt    240
gctgcattgc ctcaaagaga accagaggat gcttcaccag ttgaagatgc aaacatgctc    300
aaggatttcg ctaagtggag aaaggatctc gaaagggagg gatttttcaa accttctcca    360
gctcatgtgg catatagatt tgctgagctt gctgcaatgt tcgctctcgg tacagcatta    420
atgtacgcta gatggcacgc aacttctgtt ttcgtgacag cttgtttctt tggagcaaga    480
tgcggttggg ttcaacatga gggaggtcac tcttcattga ctggatcaat ctggtgggat    540
aagagaatac aggcttttac agcaggattc ggtctcgcta gttctggtga tatgtggaat    600
ttaatgcata acaagcatca cgcaacccct caaaaagtta ggcacgatat ggatttggat    660
actacaccag ctgttgcatt tttcaatact gctgtggaag agaacagacc taggaagttt    720
tctaaacttt ggttgagagt tcaggcttgg accttcgttc ctgtgacttc aggactcgtg    780
cttttggctt ggatgtatct cttacatcca agacacattg caagaaggaa gaattacgaa    840
gaggctgcat ggatcgttgc tgcacatgtg ataaggacat cagttattaa agctgtgaca    900
ggatatagtt ggataacctg ttacggtctc tttttaagta ccatgtgggt ttctggatgc    960
tatctttttg ctcatttctc aaccagtcat actcaccttg atgttgtgcc ttcagataag   1020
catttgagtt gggttagata tgctgtggat cacactattg atatcgatcc atctaaatca   1080
gttgtgaatt ggcttatggg ttacttgaac tgtcaggtta tccatcactt gtttcctgat   1140
atgccacaat tcagacagcc agaagtttct agaaggtttg tgtcattcgc taagaaatgg   1200
aatctcaact acaaggttat gtcttattac ggagcttgga aagcaacatt cggtaacctt   1260
aacgaagttg gaaagcacta ctatattcag ggttctcaaa tcacaaaaaa gaccgtgtaa   1320
```

<210> SEQ ID NO 20
<211> LENGTH: 439
<212> TYPE: PRT
<213> ORGANISM: Ostreococcus RCC809

<400> SEQUENCE: 20

```
Met Gly Lys Gly Ala Arg Asn Pro Gly Ala Arg Ala Trp Lys Ser Thr
1               5                   10                  15

Leu Glu Pro His Ala Val Ala Lys Ser Phe Asp Arg Arg Trp Val Lys
            20                  25                  30

Val Asp Gly Val Glu Tyr Asp Val Thr Asp Phe Lys His Pro Gly Gly
        35                  40                  45

Ser Val Ile Tyr Tyr Met Leu Ser Asn Thr Gly Ala Asp Ala Thr Glu
    50                  55                  60

Ala Phe Lys Glu Phe His Tyr Arg Ser Lys Lys Ala Arg Lys Ala Leu
65                  70                  75                  80

Ala Ala Leu Pro Gln Arg Glu Pro Glu Asp Ala Ser Pro Val Glu Asp
                85                  90                  95

Ala Asn Met Leu Lys Asp Phe Ala Lys Trp Arg Lys Asp Leu Glu Arg
            100                 105                 110

Glu Gly Phe Phe Lys Pro Ser Pro Ala His Val Ala Tyr Arg Phe Ala
        115                 120                 125

Glu Leu Ala Ala Met Phe Ala Leu Gly Thr Ala Leu Met Tyr Ala Arg
```

```
    130                 135                 140

Trp His Ala Thr Ser Val Phe Val Thr Ala Cys Phe Phe Gly Ala Arg
145                 150                 155                 160

Cys Gly Trp Val Gln His Glu Gly Gly His Ser Ser Leu Thr Gly Ser
                165                 170                 175

Ile Trp Trp Asp Lys Arg Ile Gln Ala Phe Thr Ala Gly Phe Gly Leu
            180                 185                 190

Ala Ser Ser Gly Asp Met Trp Asn Leu Met His Asn Lys His His Ala
        195                 200                 205

Thr Pro Gln Lys Val Arg His Asp Met Asp Leu Asp Thr Thr Pro Ala
    210                 215                 220

Val Ala Phe Phe Asn Thr Ala Val Glu Glu Asn Arg Pro Arg Lys Phe
225                 230                 235                 240

Ser Lys Leu Trp Leu Arg Val Gln Ala Trp Thr Phe Val Pro Val Thr
                245                 250                 255

Ser Gly Leu Val Leu Leu Ala Trp Met Tyr Leu Leu His Pro Arg His
            260                 265                 270

Ile Ala Arg Arg Lys Asn Tyr Glu Glu Ala Ala Trp Ile Val Ala Ala
        275                 280                 285

His Val Ile Arg Thr Ser Val Ile Lys Ala Val Thr Gly Tyr Ser Trp
    290                 295                 300

Ile Thr Cys Tyr Gly Leu Phe Leu Ser Thr Met Trp Val Ser Gly Cys
305                 310                 315                 320

Tyr Leu Phe Ala His Phe Ser Thr Ser His Thr His Leu Asp Val Val
                325                 330                 335

Pro Ser Asp Lys His Leu Ser Trp Val Arg Tyr Ala Val Asp His Thr
            340                 345                 350

Ile Asp Ile Asp Pro Ser Lys Ser Val Val Asn Trp Leu Met Gly Tyr
        355                 360                 365

Leu Asn Cys Gln Val Ile His His Leu Phe Pro Asp Met Pro Gln Phe
    370                 375                 380

Arg Gln Pro Glu Val Ser Arg Arg Phe Val Ser Phe Ala Lys Lys Trp
385                 390                 395                 400

Asn Leu Asn Tyr Lys Val Met Ser Tyr Tyr Gly Ala Trp Lys Ala Thr
                405                 410                 415

Phe Gly Asn Leu Asn Glu Val Gly Lys His Tyr Tyr Ile Gln Gly Ser
            420                 425                 430

Gln Ile Thr Lys Lys Thr Val
        435
```

<210> SEQ ID NO 21
<211> LENGTH: 819
<212> TYPE: DNA
<213> ORGANISM: Fragilariopsis cylindrus CCMP 1102

<400> SEQUENCE: 21

```
atggatgaat acaaggcaac tttagagagt gtgggagatg ctataataca atgggcagat      60

cctgagagtc aatttactgg ttttacaaag ggatggtttc ttacagattt cacctcagct     120

ttcagtatag cacttgttta cgtgttgttc gttattatcg gtagtcaagt tatgaaggtg     180

cttcctgcta ttgatcctta cccaataaag tttttctaca atgtttctca gatcatgttg     240

tgtgcataca tgactataga agcttgcctt ttggcatata gaaacggata cacaatcatg     300

ccttgtgttg gttataatag ggatgatcca gctataggaa acctcttatg gctcttttac     360
```

```
gtttcaaaag tgtgggattt ctgggatacc atcttcattg ttcttggtaa gaaatggaga    420

caactcagtt tcttacatgt gtatcatcac actacaatct ttctcttcta ctggttaaat    480

gctaacgttt tctatgatgg agatatatac cttacaatcg cattgaatgg tttcatacat    540

actgtgatgt acacatacta ctttatctgt atgcacacca aggataagaa aactggaaag    600

tctttgccta tatggtggaa gtcttcactc acacttttgc aattatttca gttcatcacc    660

atgatgtcac agggactcta tttaataatt ttcggttgcg agagtttgtc tataagggtt    720

accgctactt acgttgtgta catactttct ttgtttttcc tcttcgctca atttttcgtg    780

gcatcttaca tgcagccaaa gaaatcaaaa actgcttga                           819


<210> SEQ ID NO 22
<211> LENGTH: 272
<212> TYPE: PRT
<213> ORGANISM: Fragilariopsis cylindrus CCMP 1102

<400> SEQUENCE: 22

Met Asp Glu Tyr Lys Ala Thr Leu Glu Ser Val Gly Asp Ala Ile Ile
1               5                   10                  15

Gln Trp Ala Asp Pro Glu Ser Gln Phe Thr Gly Phe Thr Lys Gly Trp
            20                  25                  30

Phe Leu Thr Asp Phe Thr Ser Ala Phe Ser Ile Ala Leu Val Tyr Val
        35                  40                  45

Leu Phe Val Ile Ile Gly Ser Gln Val Met Lys Val Leu Pro Ala Ile
    50                  55                  60

Asp Pro Tyr Pro Ile Lys Phe Phe Tyr Asn Val Ser Gln Ile Met Leu
65                  70                  75                  80

Cys Ala Tyr Met Thr Ile Glu Ala Cys Leu Leu Ala Tyr Arg Asn Gly
                85                  90                  95

Tyr Thr Ile Met Pro Cys Val Gly Tyr Asn Arg Asp Asp Pro Ala Ile
            100                 105                 110

Gly Asn Leu Leu Trp Leu Phe Tyr Val Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Phe Tyr Asp Gly Asp Ile Tyr Leu Thr Ile Ala Leu Asn
                165                 170                 175

Gly Phe Ile His Thr Val Met Tyr Thr Tyr Tyr Phe Ile Cys Met His
            180                 185                 190

Thr Lys Asp Lys Lys Thr Gly Lys Ser Leu Pro Ile Trp Trp Lys Ser
        195                 200                 205

Ser Leu Thr Leu Leu Gln Leu Phe Gln Phe Ile Thr Met Met Ser Gln
    210                 215                 220

Gly Leu Tyr Leu Ile Ile Phe Gly Cys Glu Ser Leu Ser Ile Arg Val
225                 230                 235                 240

Thr Ala Thr Tyr Val Val Tyr Ile Leu Ser Leu Phe Phe Leu Phe Ala
                245                 250                 255

Gln Phe Phe Val Ala Ser Tyr Met Gln Pro Lys Lys Ser Lys Thr Ala
            260                 265                 270


<210> SEQ ID NO 23
<211> LENGTH: 867
<212> TYPE: DNA
```

<213> ORGANISM: Caenorhabditis elegans

<400> SEQUENCE: 23

```
atggctcagc acccactcgt tcagaggtta cttgatgtta aattcgatac aaagaggttc      60

gtggcaatag caactcatgg tcctaaaaat ttccctgatg ctgaaggaag aaagtttttc     120

gcagatcatt tcgatgttac tattcaagct agtatactct acatggttgt ggtttttggt     180

actaaatggt tcatgagaaa caggcaacct ttccagttaa caatccccact taacatatgg     240

aacttcattt tggctgcatt ctcaatcgct ggagcagtga agatgacccc tgagtttttc     300

ggaactattg ctaacaaggg tattgtggca tcatactgta aggttttcga tttcaccaaa     360

ggagaaaacg gttactgggt ttggcttttc atggctagta agctttttga gttggtggat     420

actatcttcc ttgttttgag aaaaaggcca ctcatgttcc tccattggta ccatcacatc     480

ctcacaatga tatacgcttg gtactctcac cctcttaccc caggattcaa cagatacggt     540

atttacttga actttgtggt tcacgcattc atgtactctt attacttcct cagatcaatg     600

aagatcaggg ttccaggatt tattgctcaa gcaatcacaa gtttacaaat agtgcagttc     660

attatctctt gtgctgttct tgcacatttg ggttatctca tgcactttac caatgctaac     720

tgcgattttg aaccttctgt gttcaaattg gctgttttta tggatactac atacctcgca     780

ctcttcgtga atttctttct tcagtcatat gttctcaggg gtggtaagga taagtacaaa     840

gctgttccaa agaaaaagaa taactga                                         867
```

<210> SEQ ID NO 24
<211> LENGTH: 288
<212> TYPE: PRT
<213> ORGANISM: Caenorhabditis elegans

<400> SEQUENCE: 24

```
Met Ala Gln His Pro Leu Val Gln Arg Leu Leu Asp Val Lys Phe Asp
1               5                   10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Val Phe Gly Thr Lys Trp Phe
    50                  55                  60

Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Phe Gly Thr Ile Ala Asn Lys Gly Ile Val Ala Ser Tyr
            100                 105                 110

Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
    130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190

Ser Tyr Tyr Phe Leu Arg Ser Met Lys Ile Arg Val Pro Gly Phe Ile
```

```
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Lys Asn Asn
        275                 280                 285


<210> SEQ ID NO 25
<211> LENGTH: 1653
<212> TYPE: DNA
<213> ORGANISM: Thalassiosira pseudonana

<400> SEQUENCE: 25

atgggtaatg gtaatcttcc agcatctaca gcacaactca agtcaacaag taaacctcaa      60

cagcaacacg agcacagaac aatcagtaaa tctgaattgg cacaacataa cactcctaag     120

tctgcttggt gtgcagttca ttcaactcct gctacagatc caagtcactc taataacaaa     180

cagcatgcac accttgtttt ggatattaca gatttcgctt ctagacatcc aggaggagat     240

ttgattcttt tggcttcagg aaaagatgca agtgtgctct tcgagaccta ccaccctagg     300

ggagttccaa cttcattaat tcaaaagctt cagatcggtg ttatggaaga ggaagctttt     360

agagatagtt tctactcttg gacagattct gatttctaca ccgttcttaa gagaagggtt     420

gtggaaagat tagaggaaag gggacttgat agaaggggtt caaaagagat ttggatcaag     480

gctttatttc tcttagttgg attctggtac tgtctttaca agatgtacac tacatcagat     540

atagatcaat acggaatagc tattgcatat agtatcggaa tgggtacttt tgctgcattc     600

atcggtacat gcatacaaca tgatggaaac cacggtgctt tcgcacagaa caagcttttg     660

aacaagttgg ctggatggac actcgatatg atcggtgctt ctgcattcac ctgggaattg     720

cagcatatgc tcggtcatca cccttacact aatgttcttg atggagtgga ggaagagaga     780

aaagaaaggg gagaggatgt ggctttggaa gagaaggatc aagagtcaga tccagatgtt     840

ttctcttcat tccctctcat gagaatgcat ccacatcaca ccactagttg gtaccataaa     900

tatcagcacc tttatgctcc tccactcttt gcattaatga cccttgctaa ggtgtttcaa     960

caggatttcg aagttgcaac atctggaaga ttgtaccata ttgatgctaa cgttagatat    1020

ggttcagttt ggaatgtgat gagattctgg gctatgaaag ttatcacaat gggatacatg    1080

atgggtttgc ctatttactt tcatggagtt ctcaggggag tgggtctttt cgttatcgga    1140

caccttgcat gtggtgaact cttagctact atgttcatag ttaaccatgt gattgaggga    1200

gtgagttatg gtacaaaaga tcttgttgga ggtgcatctc acggagatga aaagaaaatt    1260

gtgaagccta caaccgtttt aggtgatacc ccaatggaga aactagaga agaggctctc    1320

aagtcaaaca gtaacaacaa caagaaaaag ggagaaaaga actcagttcc tagtgtgcca    1380

tttaatgatt gggctgcagt gcaatgccag acttctgtta actggtctcc tggttcatgg    1440

ttttggaatc atttcagtgg aggtttgtct caccaaatcg agcatcacct cttcccaagt    1500

atatgtcata ctaactactg ccacattcaa gatgttgtgg aatctacatg tgctgagtac    1560

ggtgtgccat atcagtctga atcaaacttg ttcgttgcat acggaaagat gatctcacat    1620
```

ttgaagttcc tcggtaaggc taagtgcgag tga 1653

<210> SEQ ID NO 26
<211> LENGTH: 360
<212> TYPE: PRT
<213> ORGANISM: Thalassiosira pseudonana

<400> SEQUENCE: 26

```
Met Gly Asn Gly Asn Leu Pro Ala Ser Thr Ala Gln Leu Lys Ser Thr
1               5                   10                  15

Ser Lys Pro Gln Gln Gln His Glu His Arg Thr Ile Ser Lys Ser Glu
            20                  25                  30

Leu Ala Gln His Asn Thr Pro Lys Ser Ala Trp Cys Ala Val His Ser
        35                  40                  45

Thr Pro Ala Thr Asp Pro Ser His Ser Asn Asn Lys Gln His Ala His
    50                  55                  60

Leu Val Leu Asp Ile Thr Asp Phe Ala Ser Arg His Pro Gly Gly Asp
65                  70                  75                  80

Leu Ile Leu Leu Ala Ser Gly Lys Asp Ala Ser Val Leu Phe Glu Thr
                85                  90                  95

Tyr His Pro Arg Gly Val Pro Thr Ser Leu Ile Gln Lys Leu Gln Ile
            100                 105                 110

Gly Val Met Glu Glu Glu Ala Phe Arg Asp Ser Phe Tyr Ser Trp Thr
        115                 120                 125

Asp Ser Asp Phe Tyr Thr Val Leu Lys Arg Arg Val Val Glu Arg Leu
    130                 135                 140

Glu Glu Arg Gly Leu Asp Arg Arg Gly Ser Lys Glu Ile Trp Ile Lys
145                 150                 155                 160

Ala Leu Phe Leu Leu Val Gly Phe Trp Tyr Cys Leu Tyr Lys Met Tyr
                165                 170                 175

Thr Thr Ser Asp Ile Asp Gln Tyr Gly Ile Ala Ile Ala Tyr Ser Ile
            180                 185                 190

Gly Met Gly Thr Phe Ala Ala Phe Ile Gly Thr Cys Ile Gln His Asp
        195                 200                 205

Gly Asn His Gly Ala Phe Ala Gln Asn Lys Leu Leu Asn Lys Leu Ala
    210                 215                 220

Gly Trp Thr Leu Asp Met Ile Gly Ala Ser Ala Phe Thr Trp Glu Leu
225                 230                 235                 240

Gln His Met Leu Gly His His Pro Tyr Thr Asn Val Leu Asp Gly Val
                245                 250                 255

Glu Glu Glu Arg Lys Glu Arg Gly Glu Asp Val Ala Leu Glu Glu Lys
            260                 265                 270

Asp Gln Glu Ser Asp Pro Asp Val Phe Ser Ser Phe Pro Leu Met Arg
        275                 280                 285

Met His Pro His His Thr Thr Ser Trp Tyr His Lys Tyr Gln His Leu
    290                 295                 300

Tyr Ala Pro Pro Leu Phe Ala Leu Met Thr Leu Ala Lys Val Phe Gln
305                 310                 315                 320

Gln Asp Phe Glu Val Ala Thr Ser Gly Arg Leu Tyr His Ile Asp Ala
                325                 330                 335

Asn Val Arg Tyr Gly Ser Val Trp Asn Val Met Arg Phe Trp Ala Met
            340                 345                 350

Lys Val Ile Thr Met Gly Tyr Met
        355                 360
```

<210> SEQ ID NO 27
<211> LENGTH: 1086
<212> TYPE: DNA
<213> ORGANISM: Hyaloperonospora parasitica

<400> SEQUENCE: 27
atggctacta aacaatcagt tgcttttcct actttgactg atcttaaaag atctcttcct 60
tctgagtgtt ttgaatcttc tttgcctctt tctctttact atacacttag atctttggtt 120
tttgctggtt ctcttgctgt ttctctttct tacgctcttg ctcaaccttt ggttcaaaac 180
ttttaccctc ttagagttgc tcttattgct ggatacactg tttttcaagg agttattttc 240
tggggatttt tcactattgg tcatgatgct ggtcatggtg ctttttctag atatcctgtt 300
cttaacttca ctgttggaac acttatgcat tctcttattt tgactccttt tgaatcttgg 360
aagttgactc atagacatca tcataaaaac actggaaata tcgatagaga tgagatcttc 420
taccctcaaa gagaatctga tgatcatcct gtttctagac atcttacttt cactcttgga 480
gctgcttggt tcgcttacct tgttgagggt tttccaccta gaaaattgaa tcattacaat 540
cctttcgagc cattgttcga gagaagagtt tctgctgttg ttatctctat cttggctcag 600
tttttcgttg caggattgtc tatttacttg tgtttccagg ttggagttca ggctgttgct 660
ctttactatt acggtcctat cttcgttttt ggtactatgc ttgttattac tacttttctt 720
catcataacg atgaagagac tccttggtac ggtgatgagg attggtctta cgttaagggt 780
aacttgtctt ctgttgatag atcttacggt cctcttatcg ataacttgtc tcataacatc 840
ggtactcatc aagttcatca tcttttccca atcatccctc attacaaatt aaagcctgct 900
acagctgctt tcagaagagc tttcccacat cttgttagaa agtctgatga aagaattttg 960
caggcttttt acagaattgg tagattgtat gctaaatatg gtgttgctga ttcttctgct 1020
aaattgttta cattgaagga agctcaactt acttctaaag ctgcttctga tgctaaagct 1080
gcttga 1086

<210> SEQ ID NO 28
<211> LENGTH: 361
<212> TYPE: PRT
<213> ORGANISM: Hyaloperonospora parasitica

<400> SEQUENCE: 28

Met Ala Thr Lys Gln Ser Val Ala Phe Pro Thr Leu Thr Asp Leu Lys
1 5 10 15

Arg Ser Leu Pro Ser Glu Cys Phe Glu Ser Ser Leu Pro Leu Ser Leu
20 25 30

Tyr Tyr Thr Leu Arg Ser Leu Val Phe Ala Gly Ser Leu Ala Val Ser
35 40 45

Leu Ser Tyr Ala Leu Ala Gln Pro Leu Val Gln Asn Phe Tyr Pro Leu
50 55 60

Arg Val Ala Leu Ile Ala Gly Tyr Thr Val Phe Gln Gly Val Ile Phe
65 70 75 80

Trp Gly Phe Phe Thr Ile Gly His Asp Ala Gly His Gly Ala Phe Ser
85 90 95

Arg Tyr Pro Val Leu Asn Phe Thr Val Gly Thr Leu Met His Ser Leu
100 105 110

Ile Leu Thr Pro Phe Glu Ser Trp Lys Leu Thr His Arg His His His
115 120 125

Lys Asn Thr Gly Asn Ile Asp Arg Asp Glu Ile Phe Tyr Pro Gln Arg

-continued

```
    130                 135                 140

Glu Ser Asp Asp His Pro Val Ser Arg His Leu Thr Phe Thr Leu Gly
145                 150                 155                 160

Ala Ala Trp Phe Ala Tyr Leu Val Glu Gly Phe Pro Pro Arg Lys Leu
                165                 170                 175

Asn His Tyr Asn Pro Phe Glu Pro Leu Phe Glu Arg Arg Val Ser Ala
            180                 185                 190

Val Val Ile Ser Ile Leu Ala Gln Phe Phe Val Ala Gly Leu Ser Ile
        195                 200                 205

Tyr Leu Cys Phe Gln Val Gly Val Gln Ala Val Ala Leu Tyr Tyr Tyr
    210                 215                 220

Gly Pro Ile Phe Val Phe Gly Thr Met Leu Val Ile Thr Thr Phe Leu
225                 230                 235                 240

His His Asn Asp Glu Glu Thr Pro Trp Tyr Gly Asp Glu Asp Trp Ser
                245                 250                 255

Tyr Val Lys Gly Asn Leu Ser Ser Val Asp Arg Ser Tyr Gly Pro Leu
            260                 265                 270

Ile Asp Asn Leu Ser His Asn Ile Gly Thr His Gln Val His His Leu
        275                 280                 285

Phe Pro Ile Ile Pro His Tyr Lys Leu Lys Pro Ala Thr Ala Ala Phe
    290                 295                 300

Arg Arg Ala Phe Pro His Leu Val Arg Lys Ser Asp Glu Arg Ile Leu
305                 310                 315                 320

Gln Ala Phe Tyr Arg Ile Gly Arg Leu Tyr Ala Lys Tyr Gly Val Ala
                325                 330                 335

Asp Ser Ser Ala Lys Leu Phe Thr Leu Lys Glu Ala Gln Leu Thr Ser
            340                 345                 350

Lys Ala Ala Ser Asp Ala Lys Ala Ala
        355                 360
```

PRODUCTION OF OMEGA-3 LONG CHAIN POLYUNSATURATED FATTY ACIDS

FIELD OF THE INVENTION

The present invention relates to a recombinant oilseed plant or cell for producing omega-3 long chain polyunsaturated fatty acids such as eicospentaenoic acid (EPA) and docosahexaenoic acid (DHA). The invention further relates to the oil produced by said recombinant oilseed plant or cell.

BACKGROUND TO THE INVENTION

Two main families of poly-unsaturated fatty acids are the omega-3 fatty acids, exemplified by EPA, and the omega-6 fatty acids, exemplified by arachidonic acid (FIG. 1).

The starting material for the omega-6 metabolic pathway is the fatty acid linoleic acid while the omega-3 pathway proceeds via linolenic acid. Linolenic acid is formed by the activity of an omega-3 desaturase (Tocher et al. 1998, Prog. Lipid Res. 37, 73-117; Domergue et al. 2002, Eur. J. Biochem. 269, 4105-41 13).

Omega-3 highly unsaturated fatty acids are recognized as being important dietary compounds for preventing arteriosclerosis and coronary heart disease, for alleviating inflammatory conditions and for retarding the growth of tumor cells. These beneficial effects are a result both of omega-3 highly unsaturated fatty acids causing competitive inhibition of compounds produced from omega-6 fatty acids, and from beneficial compounds produced directly from the omega-3 highly unsaturated fatty acids themselves (Simopoulos et al. (1986) Health Effects of Polyunsaturated Fatty Acids in Seafoods, Academic Press, New York).

Omega-3 long chain polyunsaturated fatty acids are crucial to brain development and normal brain functioning (Neuringer, et al., (1988) *Annu Rev Nutr* 8, 517-541) with DHA particularly important to brain functioning due to its influence on neural membrane properties, which modulate cell signalling (Uauy, R., and Dangour, A. D. (2006) *Nutr Rev* 64, S24-33; discussion S72-91). DHA concentration in the brain decreases with age in humans, something that has been postulated to be consequential to the age-related deterioration in central nervous system functions (Soderberg et al. (1991) *Lipids* 26, 421-425). Evidence from animal studies supports this, with animals fed a low omega-3 long chain polyunsaturated fatty acid diet showing cognitive deficits (Suzuki et al. (1998) *Mech Ageing Dev* 101, 119-128) that are ameliorated by DHA supplementation (Moriguchi, T., and Salem, N., Jr. (2003) *J Neurochem* 87, 297-309; Chung, et al. (2008) *J Nutr* 138, 1165-1 171).

In humans, it has been consistently reported that a higher intake offish is related to reduced cognitive decline (van Gelder et al. (2007) *Am J Clin Nutr* 85, 1142-1 147; Kalmijn et al. (1997) *Ann Neurol* 42, 776-782; Morris et al. (2005) *Arch Neurol* 62, 1849-1853; Kalmijn et al. (1997) *Am J Epidemiol* 145, 33-41) and incidence of dementia (Kalmijn et al. (1997) *Ann Neurol* 42, 776-782), and associated with better cognitive performance (Morris et al., (2005) *Arch Neurol* 62, 1849-1853; Kalmijn et al. (2004) *Neurology* 62, 275-280; Nurk et al. (2007) *Am J Clin Nutr* 86, 1470-1478; Dangour et al. (2009) *J Nutr Health Aging* 13, 198-202). Significant positive relationships between cognitive outcomes and dietary intake levels of omega-3 long chain polyunsaturated fatty acids have also been established (van Gelder et al. (2007) *Am J Clin Nutr* 85, 1142-1 147; Morris et al. (2003) *Arch Neurol* 60, 940-946; Kalmijn et al. (2004) *Neurology* 62, 275-280). These positive relationships are further strengthened if one considers the plasma or erythrocyte level/status of omega-3 long chain polyunsaturated fatty acids. Here, DHA/EPA levels have been associated with better cognitive function in normal older adult (Whalley et al. (2004) *Am J Clin Nutr* 80, 1650-1657; Whalley et al. (2008) *Am J Clin Nutr* 87, 449-454), better cognitive outcomes over time (Whalley et al. (2008) *Am J Clin Nutr* 87, 449-454), and reduced risk of cognitive decline (Heude et al. (2003) *Am J Clin Nutr* 77, 803-808) and a lower risk of developing dementia (Schaefer et al. (2006) *Arch Neurol* 63, 1545-1550).

Studies in cognitively healthy populations have failed to show efficacy in improving cognition (Dangour et al. (2010) *Am J Clin Nutr* 91, 1725-1732; van de Rest et al. (2008) *Neurology* 71, 430-438). However, omega-3 long chain polyunsaturated fatty acid supplementation has been shown to be efficacious in cognitively impaired individuals (primarily mild cognitively impaired; MCI), where interventions had a beneficial effect on cognitive outcomes (Chiu et al. (2008) *Prog Neuropsychopharmacol Biol Psychiatry* 32, 1538-1544; Freund-Levi et al. (2006) *Arch Neurol* 63, 1402-1408; Yurko-Mauro et al. (2010) *Alzheimers Dement* 6, 456-464). Furthermore, they have been shown to be beneficial in at risk AD individuals carrying the apolipoprotein E (ApoE) 84 allele, with these individuals showing an improvement in sustained attention after 26 weeks intervention with both low (226 mg EPA, 176 mg DHA) and high (1093 mg EPA, 847 mg DHA) doses offish oil.

Bacteria and yeast are not known to synthesize omega-3 highly unsaturated fatty acids and only a few fungi are known which can produce minor and trace amounts of omega-3 highly unsaturated fatty acids (Weete (1980) Lipid Biochemistry of Fungi and Other Organism. Plenum Press, New York; Wassef, M. (1977) "Fungal lipids." Adv. Lipid Res.).

Currently the primary dietary source of omega-3 highly unsaturated fatty acids is from certain fish oils which can contain up to 20-30% of these fatty acids in their triacylglycerides. Consequently large quantities of fish oil are processed and encapsulated each year for sale as a dietary supplement.

However, fish stocks may undergo natural fluctuations or may be depleted by overfishing. Furthermore, fish oils, can accumulate environmental pollutants and may contain high levels of fat-soluble vitamins that are found naturally in fish oils. When ingested, these vitamins are stored and metabolized in fat in the human body rather than excreted in urine. Additionally, fish oils have an unpleasant taste and odour when they undergo oxidation, and as such cannot be added to processed foods as a food additive, without impairing the taste of the food product. Moreover, the refining of pure omega-3 highly unsaturated fatty acids from crude extracts of fish oils is an involved and expensive process resulting in very high prices for pure forms of these fatty acids.

The primary natural source of omega-3 unsaturated fatty acids in fish oil is in fact marine unicellular microbes such as algae and diatoms, at the base of the aquatic foodweb. These highly unsaturated fatty acids are important components of photosynthetic membranes. Omega-3 highly unsaturated fatty acids accumulate in the food chain and are eventually incorporated into fish oils.

Owing to the positive characteristics of omega-3 polyunsaturated fatty acids, genes have been identified which are involved in the biosynthesis of these fatty acids in a variety of organisms.

Linoleic acid (LA, $18{:}2^{\Delta 9,12}$) is converted to a-linolenic acid (ALA, $18{:}3^{\Delta 9,12,15}$) the first of the omega-3 fatty acids, by the action of a Δ15 desaturase. Subsequently, ALA is converted to stearodonic acid (SDA, 18:4$^{\Delta 6,9,12,15}$) by the activity of a 46 desaturase; SDA is converted to eicosatetraenoic acid (ETA, 20:4$^{\Delta 8,11,14,17}$) by the activity of an elongase; and ETA is converted to eicosapentaenoic acid (EPA, 20:5$^{\Delta 5,8,11,14,17}$) by the activity of a 45 desaturase. Alternatively, ETA and EPA can be produced from di-homo γ-linolenic acid (DGLA, 20:3$^{\Delta 8,11,14}$) and arachidonic acid (ARA, 20:4$^{\Delta 5,8,11,14}$) respectively, by the activity of a Δ17 desaturase. EPA can be further converted to DHA by the activity of an elongase and a Δ4 desaturase (see FIG. 1).

While higher plants comprise polyunsaturated fatty acids such as linoleic acid and linolenic acid, long-chain polyunsaturated fatty acids such as DHA and EPA are not found at all in the seed oil of such plants, or only in miniscule, nutritionally-irrelevant amounts. The production of long-chain polyunsaturated fatty acids, in particular omega-3 fatty acids, in higher plants would be advantageous since large amounts of high-quality long-chain polyunsaturated fatty acids (and associated triacylglycerides) for the food industry, animal nutrition and pharmaceutical purposes might be obtained economically.

Transgenic linseed oil plants have been shown to result in the accumulation of high levels of Δ6 desaturated $C_{18}$ fatty acids. However, only very low levels of $C_{20}$ polyunsaturated fatty acids have been obtained. The synthesis and accumulation of omega-3 LC-PUFAs such as EPA and DHA in the seeds of transgenic plants has previously reported in the literature but with limited success and unpredictable results.

Abbadi et al. (Plant Cell. 2004 October; 16 (10): 2734-48. Epub 2004 Sep. 17) described attempts to produce EPA in the seeds of transgenic linseed, using a three-gene construct containing a Δ6-desaturase (D6D) from *Phaeodactylum tricornutum* (AY082393), Δδ-elongase (D6E) from *Physcomitrella patens* (AF428243) and 45-desaturase (D5D) from *Phaeodactylum tricornutum* (AY082392). Linseed was chosen as a host species for the seed-specific expression of these genes on account of the very high levels of endogenous substrate (ALA) for prospective conversion to EPA. However, despite the presence of almost 50% ALA in the seeds of developing linseed, less than 1% EPA (0.8% of total fatty acids) was generated. In addition, very high levels of the undesired biosynthetic intermediate the omega-6 fatty acid y-linolenic acid (GLA) were reported (16.8% of total fatty acids). This simultaneous accumulation of high levels of GLA and low synthesis of EPA was ascribed by Abbadi et al. (Plant Cell. 2004 October; 16 (10): 2734-48. Epub 2004 Sep. 17) to the phospholipid-dependent substrate-requirements of the D6D.

Similar results were also reported by Wu et al. (Nat Biotechnol, 2005, 23:1013-7) who described the seed-specific expression of a 3 gene construct (D6D from *Pythium irregulare*, CAJ30866; D6E from *Physcomitrella patens*; D5D from Thraustochytrium, AX467713) in *Brassica juncea*, yielding 0.8% EPA but 27.7% of the undesirable omega-6 GLA. More complex gene constructs were also reported by Wu et al. in which they attempted to boost the accumulation of EPA in transgenic *B. juncea*. A four gene construct comprising the same D6D, D6E, D5D activities and additionally the FAD2 A12-desaturase from *Calendula officinalis* (AF343065) resulted in a small increase in EPA to 1.2% but also a concomitant increase in GLA to 29.4%. A five gene construct, comprising D6D, D6E, D5D, FAD2 and a second Δδ-elongase D6E #2 from *Thraustochytrium* (AX214454) had equally marginal impact on the fatty acid composition of the seeds of transgenic *B. juncea*, yielding 1.4% EPA and 28.6% GLA. A six gene construct, comprising the same D6D, D6E, D5D, FAD2, D6E #2 and a w3-desaturase w3D from *Phytophthora infestans* (CS160901), yielded the best levels of EPA at 8.1%-however, the levels of GLA remained high at 27.1%. In a further iteration, Wu et al. (Nat Biotechnol, 2005, 23:1013-7) also attempted to engineer the accumulation of both EPA and DHA, through the seed-specific expression of nine genes (D6D, D6E, D5D, FAD2, D6E #2, w3D, and additionally a A5-elongase (D5E) from fish (Oncorhynchus mykiss; CS020097), a A4-desaturase (D4D) from *Thraustochytrium* (AF489589), and an acyltransferase also from the same organism). This yielded *B. juncea* seeds containing on average 8.1% EPA and 0.2% DHA. Again, GLA levels remained markedly higher (27.3%). Wu et al. reported a maximal level of EPA observed in transgenic *B. juncea* as 15% and a maximal DHA level of 1.5% (based on individual plants for their nine gene construct.

Similar experiments were carried out in the model oilseed species *Arabidopsis thaliana*: Robert et al. (Functional Plant Biol, 2005, 32: 473-479) reported the low level accumulation of EPA (3.2% of total fatty acids) in the seeds of *Arabidopsis* on the expression of two genes, a A functional D6D/D5D from zebrafish (*Danio rerio*, AF309556) and a D6E from the nematode *Caenhorabditis elegans* (Z68749). Interestingly, this construct also showed significantly reduced accumulation of GLA, a fact that Robert et al. attributed to the acyl-CoA-dependent substrate requirement of the D6D/D5D. Further transformation of this EPA-accumulating *Arabidopsis* line with genes for DHA synthesis (D4D and D5E from *Pavlova salina*, AY926605, AY926606) resulted in a mean level of 0.3% DHA, again with basal levels of the unwanted co-product GLA (0.3%).

Very similar results were reported by Hoffmann et al. (J Biol Chem, 2008, 283:22352-62) who postulated that the use of an "acyl-CoA-dependent" pathway in transgenic plants would decrease the build-up of biosynthetic intermediates such as GI_A whilst simultaneously increase the accumulation of EPA. However, the seed-specific expression in *Arabidopsis* of acyl-CoA-dependent D6D and D5D activities from *Mantoniella squamata* (AM949597, AM949596) (in conjunction with the previously described D6E from *P. patens*) yielded barely detectable levels of EPA (<0.1% of total seed fatty acids and <0.05% GLA. Analogous data have been reported by Ruiz-Lopez et al. (Transgenic Res. 2012 (doi: 10.1007/s1 1248-012-9596-0)) who expressed a number of different gene combinations in *Arabidopsis*. Notably, a six gene construct comprising a D6D from *Pythium irregulare*, (CAJ30866); D6E from *Physcomitrella patens* (AF428243); D5D from *Thraustochytrium*, (AX467713); a bifunctional D12/15 desaturase from *Acanthamoeba castellanii*, EF017656; w3D from *Phytophthora infestans* (CS 160901) and a second D6E from *Thalassiosira pseudonana*, (AY591337) yielded 2.5% EPA of total seed fatty acids with the concomitant accumulation of 13.3% GLA. In contrast, a four gene construct that contained an acyl-CoA-dependent D6D from *Ostreococcus tauri* (AY746357), D6E from *Thalassiosira pseudonana* (AY591337), D5D from *Thraustochytrium*, (AX467713) and FAD2 from *Phytophtora sojae* (CS423998) generated low levels of both EPA (2% of total fatty acids) and GLA (1.0%).

More recently, Cheng et al. (Transgenic Res, 2010, 19:221-9) reported the accumulation of EPA in transgenic *Brassica carinata*. For example, the seed-specific expression of 3 genes (D6D from *Pythium irregulare*, CAJ30866; D6E from *Thalassiosira pseudonana*, AY591337; D5D from *Thraustochytrium*, AX467713) resulted in a mean level of 2.3% EPA, with high level co-accumulation of GLA (17.6%). A four gene construct (D6D, D6E, D5D and w3D from *Claviceps purpurea*, EF536898) resulted in 4.2% EPA and 11.8% GLA, whilst a five gene construct (D6D, D6E, D5D, w3D and an additional w3-desaturase from *Pythium* irregular, (FB753541)) yielded 9.7% EPA and 11.1% GLA. Such levels are very similar to that observed with five and six gene constructs in *B. juncea* (Wu et al. 2005, Nat Biotechnol, 2005, 23:1013-7). Cheng et al. introduced a different 5 gene construct (D6D from *Pythium irregulare*, CAJ30866; D6E from *Thraustochytrium*, HC476134; D5D from *Thraustochytrium*, AX467713; FAD2 from *Calendula officinalis*, AF343065 and w3D from *Pythium irregulare*, FB753541) into two different cultivars of *B. carinata*, differing in their accumulation of the C22 monounsaturated fatty acid erucic acid. Expression of this construct in conventional high erucic acid *B. carinata* resulted again in a mean accumulation of 9.3% EPA and 18.2% GLA. Expression in the zero-erucic acid genotype yielded an increase in EPA though this genotype also resulted in the co-accumulation of high levels of GLA (26.9%).

The present invention addresses the need for systems that produce commercially useful levels of omega-3 highly unsaturated fatty acids in the seeds of terrestrial plants.

SUMMARY OF THE INVENTION

*Camelina sativa* is a genus within the flowering plant family Brassicaceae. Camelina is a short season crop, and has gained notoriety for its ability to withstand water shortages in early stages of development. In recent years, there has been increasing interest in the use of camelina oil as a biofuel and bio-lubricant, mainly in view of this crop's low nitrogen requirements.

The present invention relates to the surprising finding that camelina can be transformed with desaturase and elongase enzymes to produce omega-3 fatty acids.

Indeed, following the introduction of these enzymes into camelina, it is not only possible to generate omega-3 fatty acids, but it is possible to create novel oil compositions.

According to a first aspect of the present invention there is provided a recombinant camelina plant or cell comprising one or more polynucleotides encoding a Δ6-desaturase, a Δδ-elongase and a A5-desaturase operably linked with one or more regulatory sequences.

Thus, there is provided a camelina plant or cell transformed with genes encoding a Δ6-desaturase, a Δδ-elongase and a Δδ-desaturase.

The Δδ-desaturase, Δδ-elongase and Δδ-desaturase enzymes can be encoded by a single or separate polynucleotide(s). What is important is that the recombinant camelina plant or host according to the first aspect of the invention comprises polynucleotide sequences for all three enzymes.

In a preferred embodiment of the first aspect of the invention, the recombinant camelina plant or cell is produced by transforming a camelina plant or cell with a polynucleotide encoding a Δ6-desaturase, a Δδ-elongase and a A5-desaturase operably linked with one or more regulatory sequences.

Alternatively, the recombinant camelina plant or cell may be produced by transforming a camelina plant or cell with separate polynucleotides each encoding a Δβ-desaturase and/or a Δβ-elongase and/or aA5-desaturase.

The recombinant camelina plant or cell of this aspect of the invention may further comprise one or more polynucleotides encoding a A12-desaturase and/or a w3 desaturase operably linked with one or more regulatory sequences. Thus, there is provided a recombinant camelina plant or cell comprising one or more polynucleotides encoding a Δ6-desaturase, a Δ6-elongase, aA5-desaturase, a Δ12-desaturase and ω3 desaturase operably linked to one or more regulatory elements. In a preferred embodiment, the recombinant camelina plant or cell is produced by transforming a camelina plant or cell with a polynucleotide encoding a Δ6-desaturase, a Δ6-elongase, a Δ5-desaturase, a A12-desaturase and a ω3 desaturase operably linked with one or more regulatory sequences.

According to a second aspect of the present invention there is provided a method for producing eicosapentaenoic acid (EPA) comprising growing a plant or cell according to the first aspect of the invention under conditions wherein said desaturase and elongase enzymes are expressed and EPA is produced in said plant or cell.

According to third aspect of the present invention there is provided a method for producing a plant seed oil comprising growing a recombinant camelina plant or cell of the first aspect of the invention whereby said desaturase and elongase enzymes are expressed and oil is produced in said plant or cell.

According to fourth aspect of the present invention there is provided a plant seed oil produced by the recombinant camelina plant or cell of the first aspect of the present invention.

According to a fifth aspect of the present invention there is provided a plant seed oil wherein EPA constitutes at least 5%, at least 10%, at least 20%, at least 25% or at least 30% (mol %) of the total of the total amount of fatty acid present in said oil. Said oil may be produced by a recombinant camelina plant or cell of the first aspect of the present invention.

In one embodiment, the EPA constitutes at least 15, 20, 25 or 30% (mol %) of the total fatty acid content of said oil, and the γ-linolenic (GLA) constitutes less than 10% (mol %) of the total fatty acid content of said oil.

In one embodiment, the EPA constitutes 20% to 35%, preferably 20 to 31% (mol %) of the total fatty acid content of said oil.

The GLA may constitute less than 7% (mol %) of the total fatty acid content of said oil. In one embodiment, the GLA constitutes 1% to 6% (mol %) of the total fatty acid content of said oil.

The ratio of the molar percentages of EPA to γ-linolenic (GLA) may be, for example, about 3:1 to about 22:1, preferably about 5:1 to about 20:1, preferably about 8:1 to about 20:1.

According to a sixth aspect of the present invention there is provided a recombinant camelina plant or cell comprising one or more polynucleotides encoding a Δ6-desaturase, a Δ6-elongase, a Δ5-desaturase, a Δ5-elongase and a Δ4-desaturase operably linked with one or more regulatory sequences.

Thus, there is provided a camelina plant or cell transformed with genes encoding a AB-desaturase, a Δ6-elongase, a Δ5-desaturase, a Δ5-elongase and a Δ4-desaturase.

The A6-desaturase, Δβ-elongase, Δ5-desaturase, Δ5-elongase and A4-desaturase can be encoded by a single or separate polynucleotide(s). What is essential is that the recombinant camelina plant or cell according to the sixth aspect of the invention comprises polynucleotide sequences for all five enzymes.

Preferably, the recombinant camelina plant or cell according to this aspect of the invention is produced by transforming a camelina plant or cell with a polynucleotide encoding a A6-desaturase, a A6-elongase, a A5-desaturase, a Δ5-elongase and a A4-desaturase operably linked with one or more regulatory sequences.

Alternatively, the recombinant camelina plant or cell may be produced by transforming a camelina plant or cell with separate polynucleotides each encoding a Δ6-desaturase, and/or Δδ-elongase, and/or Δ5-desaturase, and/or Δδ-elongase and/or a A4-desaturase.

The recombinant camelina plant or cell of this aspect of the invention may further comprise one or more polynucleotides encoding a Δ12-desaturase and/or a ω3 desaturase operably linked with one or more regulatory sequences. Thus, there is provided a recombinant camelina plant or cell comprising one or more polynucleotides encoding a Δ6-desaturase, a Δ6-elongase, a A5-desaturase, a Δ12-desaturase, a Δδ-elongase, a A4-desaturase and a ω3 desaturase operably linked to one or more regulatory elements. In a preferred embodiment, the recombinant camelina plant or cell is produced by transforming a camelina plant or cell with a polynucleotide encoding a A6-desaturase, a Δ6-elongase, a Δ5-desaturase, a Δ5-elongase, a Δ4-desaturase, a A12-desaturase and a ω3 desaturase operably linked with one or more regulatory sequences.

According to a seventh aspect of the present invention there is provided a method for producing docosahexaenoic acid (DHA) and/or EPA comprising growing a plant or cell according to the sixth aspect of the invention under conditions wherein said desaturase and elongase enzymes are expressed and DHA and/or EPA is produced in said plant or cell.

According to eighth aspect of the present invention there is provided a method for producing a plant seed oil comprising growing a recombinant camelina plant or cell of the sixth aspect of the invention whereby said desaturase and elongase enzymes are expressed and oil is produced in said plant or cell.

According to a ninth aspect of the present invention there is provided a plant seed oil produced by the recombinant camelina plant or cell of the sixth aspect of the present invention.

According to a tenth aspect of the present invention there is provided a plant seed oil wherein DHA constitutes at least 1%, preferably at least 3%, more preferably at least 5%, still more preferably at least 7%, still more preferably at least 10%, still more preferably at least 13% or still more preferably at least 15% (mol %) of the total amount of fatty acid present in said oil. Said oil may be produced by a recombinant camelina plant or cell according to the sixth aspect of the present invention.

Preferably, according to this aspect of the invention the γ-linolenic (GLA) constitutes less than 5%, more preferably less than 4.5%, still more preferably less than 4%, still more preferably less than 3.5%, still more preferably less than 3%, still more preferably less than 2.5%, still more preferably less than 2% (mol %) of the total fatty acid content of said oil.

In one embodiment the DHA constitutes 5% to 20% (mol %) of the total fatty acid content of said oil.

In another embodiment the DHA constitutes 5% to 20% (mol %) of the total fatty acid content of said oil.

In another embodiment the DHA constitutes 10% to 20% (mol %) of the total fatty acid content of said oil.

In another embodiment the DHA constitutes 10 to 15% (mol %) of the total fatty acid content of said oil.

In another embodiment the DHA constitutes 10 to 13.7% (mol %) of the total fatty acid content of said oil.

Preferably the combined percentage of DHA and EPA is at least 20% of the total fatty acid content of said oil.

In one embodiment the combined percentage of DHA and EPA is 20 to 30% of the total fatty acid content of said oil.

In one embodiment the combined percentage of DHA and EPA is 21 to 27% of the total fatty acid content of said oil.

In one embodiment the DHA constitutes 4% to 10%, preferably 4% to 8%, preferably 5% to 7.5% (mol %) of the total fatty acid content of said oil.

In one embodiment the GLA constitutes 0% to 4.5% (mol %) of the total fatty acid content of said oil.

In one embodiment the GLA constitutes 0.5% to 4.5% (mol %) of the total fatty acid content of said oil.

In another embodiment the GLA constitutes 1.0% to 4.5% (mol %) of the total fatty acid content of said oil.

In another embodiment the GLA constitutes 1.5% to 4.5% (mol %) of the total fatty acid content of said oil.

In another embodiment the GLA constitutes 0% to 3.5% (mol %) of the total fatty acid content of said oil.

In another embodiment the GLA constitutes 0.5% to 3.5% (mol %) of the total fatty acid content of said oil.

In another embodiment the GLA constitutes 1.0% to 3.5% (mol %) of the total fatty acid content of said oil.

In another embodiment the GLA constitutes 1.5% to 3.5% (mol %) of the total fatty acid content of said oil.

In one embodiment the GLA constitutes 1.5% to 3.2% (mol %) of the total fatty acid content of said oil.

The ratio of the molar percentages of EPA to DHA may be, for example, about 0.8:1 to about 1.4:1, preferably about 1:1 to about 1:1.3.

In another embodiment the ratio of the molar percentages of the sum of (EPA+DHA) to GLA is about 20:1 to about 3:1, 5:1, 7:1 or 10:1.

In another embodiment the ratio of the molar percentages of the sum of (EPA+DHA) to GLA is about 17:1 to about 3:1, 5:1, 7:1 or 10:1.

In another embodiment the ratio of the molar percentages of the sum of (EPA+DHA) to GLA is about 16.4:1 to about 3:1, 5:1, 7:1 or 10:1.

In another embodiment the ratio of the molar percentages of the sum of (EPA+DHA) to GLA is about 8:1 to about 3:1.

According to an eleventh aspect of the present invention there is provided use of camelina in the manufacture of an omega-3 fatty acid, preferably EPA or DHA.

According to a twelfth aspect of the present invention there is provided a camelina seed comprising a phosphatidylcholine wherein the total number of carbon atoms of the fatty acid acyl groups of said phosphatidylcholine is 40. Preferably the seed is a seed of the plant of the first aspect of the invention.

According to a thirteenth aspect of the present invention there is provided a camelina seed comprising phosphatidylcholine, wherein the total number of carbon atoms:double bonds of the fatty acid acyl groups of said phosphatidylcholine species is selected from the group consisting of: 34:4, 34:0, 36:7, 38:1 1, 38:9, 38:8, 38:7, 38:6, 38:5, 40:1 1, 40:10, 40:9, 40:8, 40:7, 40:6, 40:5 and 40:4. Preferably the seed comprises all the phosphatidylcholine species 34:4, 34:0, 36:7, 38:1 1, 38:9, 38:8, 38:7, 38:6, 38:5, 40:1 1, 40:10, 40:9, 40:8, 40:7, 40:6, 40:5 and 40:4. Preferably the seed is a seed of the plant of the first aspect of the invention.

According to a fourteenth aspect of the present invention there is provided a camelina seed comprising one or more phosphatidylethanolamine species wherein the total number of carbon atoms:double bonds of the fatty acid acyl groups of said phosphatidylethanolamine species is selected from the group consisting of 34:4, 36:7, 38:8, 38:7, 38:6, 38:5, 40:10, 40:9, 40:8, 40:7, 40:6, 40:5. Preferably the seed comprises all of the phosphatidylethanolamine species 34:4, 36:7, 38:8, 38:7, 38:6, 38:5, 40:10, 40:9, 40:8, 40:7, 40:6, 40:5. Preferably the seed is a seed of the plant of the first aspect of the invention.

According to a fifteenth aspect of the present invention there is provided a camelina seed oil comprising the phosphatidylcholine species 34:4, 34:0, 36:7, 38:1 1, 38:9, 38:8, 38:7, 38:6, 38:5, 40:1 1, 40:10, 40:9, 40:8, 40:7, 40:6, 40:5 and 40:4. Preferably the seed is a seed of the plant of the sixth aspect of the invention.

According to a sixteenth aspect of the present invention there is provided a camelina seed wherein the seed comprises one or more phosphatidylethanolamine species wherein the total number of carbon atoms:double bonds of the fatty acid acyl groups of said phosphatidylethanolamine species is selected from the group consisting of 34:4, 36:7, 38:8, 38:7, 38:6, 38:5, 40:10, 40:9, 40:8, 40:7, 40:6, 40:5. Preferably the camelina oil comprises all of the phosphatidylethanolamine species 34:4, 36:7, 38:8, 38:7, 38:6, 38:5, 40:10, 40:9, 40:8, 40:7, 40:6, 40:5. Preferably the seed is a seed of the plant of the sixth aspect of the invention.

According to a seventeenth aspect of the present invention there is provided a camelina seed or oil wherein said seed or oil comprises triglycerides wherein the number of carbon atom double bonds of said triglycerides is 58:8, 58:9 and 58:10. The seed or oil may be derived from the transgenic camelina plant of the invention.

In addition to the specific elongase and desaturase enzymes referred to herein, the recombinant camelina plant or cell defined herein may further encode other enzymes involved in polyunsaturated fatty acid synthesis, in particular enzymes involved in omega-3 polyunsaturated fatty acid synthesis. Alternatively, the recombinant camelina plant may only be transformed with the fatty acid synthesis enzymes referred to herein.

The recombinant camelina plant defined herein may be in the form of a seed.

The desaturase and elongase enzymes used in the present invention may be derived from, for example, algae, bacteria, mould or yeast.

In one embodiment, the A6-desaturase used in the present invention is derived from *Ostreococcus*, preferably OtD6 from *Ostreococcus tauri* (Domergue et al. Biochem. J. 389 (PT 2), 483-490 (2005). In one embodiment, the A6-desaturase is encoded by a polynucleotide sequence that has at least 50, 60, 70, 80, 85, 90, 95, 97, 99% or 100% identity to SEQ ID NO:1. In another embodiment, the A6-desaturase comprises an amino acid sequence that has at least 50, 60, 70, 80, 85, 90, 95, 97, 99% or 100% identity to SEQ ID NO:2.

In another embodiment, the A6-desaturase used in the present invention is O809D6 from *Ostreococcus* RCC809. In one embodiment, the A6-desaturase is encoded by a polynucleotide sequence that has at least 50, 60, 70, 80, 85, 90, 95, 97, 99% or 100% identity to SEQ ID NO:19. In another embodiment, the A6-desaturase comprises an amino acid sequence that has at least 50, 60, 70, 80, 85, 90, 95, 97, 99% or 100% identity to SEQ ID NO:20.

In one embodiment, the Δδ-elongase used in the present invention is derived from *Physcomitrella*, and is preferably from *Physcomitrella patens*. Preferably the Δ6-elongase is PSE1 derived from *Physcomitrella patens* (Zank. et al., *Plant J.* 31 (3), 255-268 (2002); AB23891 4). In one embodiment, the Δδ-elongase is encoded by a polynucleotide sequence that has at least 50, 60, 70, 80, 85, 90, 95, 97, 99% or 100% identity to SEQ ID NO:3. In another embodiment, the Δδ-elongase comprises an amino acid sequence that has at least 50, 60, 70, 80, 85, 90, 95, 97, 99% or 100% identity to SEQ ID NO:4.

In another embodiment, the Δδ-elongase used in the present invention is FcElo6, a Δ6 fatty acid elongase from *Fragilariopsis cylindrus* CCMP 1102. In one embodiment, the Δδ-elongase is encoded by a polynucleotide sequence that has at least 50, 60, 70, 80, 85, 90, 95, 97, 99% or 100% identity to SEQ ID NO:21. In another embodiment, the Δδ-elongase comprises an amino acid sequence that has at least 50, 60, 70, 80, 85, 90, 95, 97, 99% or 100% identity to SEQ ID NO:22.

In another embodiment, the Δδ-elongase used in the present invention is CeElo6, a Δ6 fatty acid elongase from *Caenorhabditis elegans* (Beaudoin et al., 2000, Proc Natl Acad Sci USA. 2000 Jun. 6; 97 (12): 6421-6). In one embodiment, the Δδ-elongase is encoded by a polynucleotide sequence that has at least 50, 60, 70, 80, 85, 90, 95, 97, 99% or 100% identity to SEQ ID NO:23. In another embodiment, the A6-elongase comprises an amino acid sequence that has at least 50, 60, 70, 80, 85, 90, 95, 97, 99% or 100% identity to SEQ ID NO:24.

In one embodiment, the A5-desaturase used in the present invention is derived from *Thraustochytrium* sp. Preferably the Δ5-desaturase is TcΔ5 derived from *Thraustochytrium* sp. (Qiu et al. J Biol Chem. 2001 Aug. 24; 276 (34): 31 561-6; AF489588). In one embodiment, the Δ5-desaturase is encoded by a polynucleotide sequence that has at least 50, 60, 70, 80, 85, 90, 95, 97, 99% or 100% identity to SEQ ID NO:5. In another embodiment, the Δ5-desaturase comprises an amino acid sequence that has at least 50, 60, 70, 80, 85, 90, 95, 97, 99% or 100% identity to SEQ ID NO:6.

In another embodiment, the EMoD5 Δ5-desaturase from *E. huxleyi* (Sequence ID 9, 10) can be used. In one embodiment, the Δ5-desaturase is encoded by a polynucleotide sequence that has at least 50, 60, 70, 80, 85, 90, 95, 97, 99% or 100% identity to SEQ ID NO:9. In another embodiment, the Δ5-desaturase comprises an amino acid sequence that has at least 50, 60, 70, 80, 85, 90, 95, 97, 99% or 100% identity to SEQ ID NO: 10.

In one embodiment, the A5-elongase used in the present invention is derived from *Ostreococcus*, preferably *Ostreococcus tauri*. Preferably the A5-elongase is OtElo5 derived from *Ostreococcus tauri* (WO 20050 123 16-A2; CS020 123). In one embodiment, the A5-elongase is encoded by a polynucleotide sequence that has at least 50, 60, 70, 80, 85, 90, 95, 97, 99% or 100% identity to SEQ ID NO:7. In another embodiment, the Δ5-elongase comprises an amino acid sequence that has at least 50, 60, 70, 80, 85, 90, 95, 97, 99% or 100% identity to SEQ ID NO:8.

In one embodiment, the Δ4-desaturase is derived from *Thraustochytrium* sp (ATCC21685). In one embodiment, the Δ4-desaturase is encoded by a polynucleotide sequence that has at least 50, 60, 70, 80, 85, 90, 95, 97, 99% or 100% identity to SEQ ID NO:17. In another embodiment, the Δ4-desaturase comprises an amino acid sequence that has at least 50, 60, 70, 80, 85, 90, 95, 97, 99% or 100% identity to SEQ ID NO: 18.

In another embodiment the Δ4-desaturase is EhD4 derived from *Emiliana huxleyi* (WO 20091 331 45-A1; HC086723; et al. Phytochemistry. 201 1 May; 72 (7).594-600). In one embodiment, the A4-desaturase is encoded by a polynucleotide sequence that has at least 50, 60, 70, 80, 85, 90, 95, 97, 99% or 100% identity to SEQ ID 15. In another embodiment, the A4-desaturase comprises an amino acid sequence that has at least 50, 60, 70, 80, 85, 90, 95, 97, 99% or 100% identity to SEQ ID NO: 16.

In another embodiment the Δ4-desaturase is TpDesk, a Δ4-desaturase from *Thalassiosira pseudonana* (Tonon et al, 2005 FEBS J. 2005 July; 272 (13): 3401-12). In one embodiment, the Δ4-desaturase is encoded by a polynucleotide sequence that has at least 50, 60, 70, 80, 85, 90, 95, 97, 99% or 100% identity to SEQ ID 25. In another embodiment, the Δ4-desaturase comprises an amino acid sequence that has at least 50, 60, 70, 80, 85, 90, 95, 97, 99% or 100% identity to SEQ ID NO:26.

In one embodiment, the A12-desaturase used in the present invention is derived from *Phytophthora*, and is preferably PsA12 from *Phytophthora sojae* (WO 2006100241 A2; CS423998). In one embodiment, the A12-desaturase is encoded by a polynucleotide sequence that has at least 70, 80, 85, 90, 95, 97, 99% or 100% identity to SEQ ID NO:1 1. In another embodiment, the A12-desaturase comprises an amino acid sequence that has at least 70, 80, 85, 90, 95, 97, 99% or 100% identity to SEQ ID NO:12.

In a one embodiment, the ω3-desaturase used in the present invention is derived from *phytophthora*, preferably *Phytophthora infestans*. Preferably the ω3-desaturase is ρi(ω3) derived from *Phytophthora infestans* (JP 2007527716; DJ418322). In one embodiment, the ω3-desaturase is encoded by a polynucleotide sequence that has at least 50, 60, 70, 80, 85, 90, 95, 97, 99% or 100% identity to SEQ ID NO:13. In another embodiment, the ω3-desaturase comprises an amino acid sequence that has at least 50, 60, 70, 80, 85, 90, 95, 97, 99% or 100% identity to SEQ ID NO: 14.

In another embodiment, the ω3-desaturase used in the present invention is Hpw-3, a ω3 desaturase gene from *Hyaloperonospora parasitica*. In one embodiment, the ω3-desaturase is encoded by a polynucleotide sequence that has at least 50, 60, 70, 80, 85, 90, 95, 97, 99% or 100% identity to SEQ ID NO:27. In another embodiment, the ω3-desaturase comprises an amino acid sequence that has at least 50, 60, 70, 80, 85, 90, 95, 97, 99% or 100% identity to SEQ ID NO:28.

Preferably the camelina referred to herein is *Camelina* satrva.

In one embodiment, the plant seed oil described herein comprises triglycerides wherein the number of carbon atoms: double bonds of said triglycerides is 58:8, 58:9 and 58:10.

DETAILED DESCRIPTION

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; *D. M. J. Lilley and J. E. Dahlberg,* 1992, *Methods of Enzymology: DNA Structure Part A: Synthesis and Physical Analysis of DNA* Methods in Enzymology, Academic Press; and E. M. Shevach and W. Strober, 1992 and periodic supplements, *Current Protocols in Immunology*, John Wiley & Sons, New York, NY. Each of these general texts is herein incorporated by reference.

Camelina

Camelina is a genus within the flowering plant family Brassicaceae. Camelina is an emerging biofuel crop, in particular *Camelina sativa*. It is also known by other names such as German sesame, false-flax, gold-of-pleasure, and Siberian oilseed. Renewed interest in *C. sativa* as a biofuel feedstock is due in part to its drought tolerance and minimal requirements for supplemental nitrogen and other agricultural inputs (Gehringer et al. (2006) Genome 49 (12): 1555-63; Gugel and Falk (2006) Canadian Journal of Plant Science 86 (4): 1047-1058).

Similar to other non-traditional, renewable oilseed feedstocks such as *Jatropha curcas* L. ("*jatropha*"), *C. sativa* grows on marginal land. Unlike *jatropha*, which is a tropical and subtropical shrub, *C. sativa* is native to Europe and is naturalized in North America, where it grows well in the northern United States and southern Canada.

In addition to its drought tolerance and broad distribution, several other aspects of *C. sativa* biology make it well suited for development as an oilseed crop. First, *C. sativa* is a member of the family Brassicaceae, and thus is a relative of both the genetic model organism *Arabidopsis thaliana* and the common oilseed crop *Brassica napus* (also known as canola). Second, the oil content of *C. sativa* seeds is comparable to that of *B. napus*, ranging from 30 to 40% (w/w) (Budin et al. (1995). Journal of the American Oil Chemists' Society 72 (3): 309-315; Gugel and Falk (2006) Canadian journal of plant science 86 (4): 1047-1058). Finally, the properties of *C. sativa* biodiesel are already well described and both seed oil and biodiesel from *C. sativa* were used as fuel in engine trials with promising results (Bernardo et al. (2003) Industrial Crops and Products 17 (3): 191-197; Frohlich and Rice (2005). Industrial Crops and Products 21 (1): 25-31).

Oils, Lipids and Fatty Acids

Polyunsaturated fatty acids can be classified into two major families (depending on the position (n) of the first double bond nearest the methyl end of the fatty acid carbon chain. Thus, the omega-6 fatty acids have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the omega-3 fatty acids have the first unsaturated double bond three carbon atoms away from the omega end of the molecule and additionally have a total of three or more double bonds, with each subsequent unsaturation occurring 3 additional carbon atoms toward the carboxyl end of the molecule.

Table 1 summarizes the common names of omega-3 fatty acids and the abbreviations that will be used throughout the specification:

TABLE 1

| Common Name | Abbreviation | Shorthand notation |
|---|---|---|
| oleic acid | OA | $18{:}1^{\Delta 9}$ |
| Linoleic acid | LA | $18{:}2^{\Delta 9,12}$ |
| γ-Linolenic | GLA | $18{:}3^{\Delta 6,9,12}$ |
| di-homo γ-linolenic acid | DGLA | $20{:}3^{\Delta 8,11,14}$ |

TABLE 1-continued

| Common Name | Abbreviation | Shorthand notation |
|---|---|---|
| Arachidonic acid | ARA | $20{:}4^{\Delta 5,8,11,14}$ |
| α-linolenic acid | ALA | $18{:}3^{\Delta 9,12,15}$ |
| stearidonic acid | SDA | $18{:}4^{\Delta 6,9,12,15}$ |
| eicosatetraenoic acid | ETA | $20{:}4^{\Delta 8,11,14,17}$ |
| eicosapentaenoic acid | EPA | $20{:}5^{\Delta 5,8,11,14,17}$ |
| docosapentaenoic acid | DPA | $22{:}5^{\Delta 7,10,\ 13,\ 16,\ 19}$ |
| docosahexaenoic acid | DHA | $22.6^{\Delta 4,7,10,\ 13,\ 16,\ 19}$ |

The fatty acids produced by the processes of the present invention can be isolated from the camelina in the form of an oil, a lipid or a free fatty acid. One embodiment of the invention is therefore oils, lipids or fatty acids or fractions thereof which have been produced by the methods of the invention, especially preferably oil, lipid or a fatty acid composition comprising EPA or DHA and being derived from the transgenic camelina.

The term "oil", or "lipid" is understood as meaning a fatty acid mixture comprising unsaturated, preferably esterified, fatty acid(s). The oil or lipid is preferably high in omega-3 polyunstaurated or, advantageously, esterified fatty acid(s). In a particularly preferred embodiment the oil or lipid has a high ALA, ETA, EPA, DPA and/or DHA content, preferably a high EPA and/or DHA content.

For the analysis, the fatty acid content of the seed can, for example, be determined by gas chromatography after converting the fatty acids into the methyl esters by transesterification of lipids such as triacylglycerides and/or phospholipids.

The omega-3 polyunstaurated acids produced in the method of the present invention, for example EPA and DHA, may be in the form of fatty acid derivatives, for example sphingolipids, phosphoglycerides, lipids, glycolipids, phospholipids, monoacylglycerol, diacylglycerol, triacylglycerol or other fatty acid esters.

The omega-3 and other polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the above-described processing step.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination, use of butylated hydroxytoluene (BHT)). Methods used include methylation of the fatty acids to produce methyl esters. Similarly, protecting groups may be removed at any step. Desirably, purification of fractions containing, for example, ALA, STA, ETA, EPA, DPA and DHA may be accomplished by treatment with urea and/or fractional distillation.

The present invention encompasses the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. Thus, the invention also provides feedstuffs, foodstuffs, cosmetics or pharmacologicals which comprise the oils, lipids, fatty acids or fatty acid mixtures of the present invention.

Total Fatty Acid Content

The term "total fatty acids content" herein refers to the sum of all cellular fatty acids that can be derivitized to fatty acid methyl esters by the base transesterification method in a given sample (as known in the art, for example as described in Sayanova et al., (1997) Proc Natl Acad Sci USA. 1997 Apr. 15; 94 (8): 421 1-6; Sayanova et al., (2003) FEBS Lett. 2003 May 8; 542 (1-3): 100-4).

Polyunsaturated Fatty Acid Biosynthetic Genes

Microorganisms, including algae, bacteria, moulds and yeasts, can synthesize polyunsaturated fatty acids and omega fatty acids in the ordinary course of cellular metabolism. Particularly well-studied are fungi including *Schizochytrium aggregatm*, species of the genus *Thraustochytrium* and *Morteriella aipina*. Additionally, many dinoflagellates (Dinophyceaae) naturally produce high concentrations of polyunsaturated fatty acids. As such, a variety of genes involved in oil production have been identified through genetic means and the DNA sequences of some of these genes are publicly available. Non-limiting examples are shown below:

| Accession No. | Description |
|---|---|
| AY1 31238 | *Argania spinosa* Δ6 desaturase |
| Y0551 18 | *Echium pitardii* var. pitardii Δ6 desaturase |
| AY0551 17 | *Echium gentianoides* Δ6 desaturase |
| AF296076 | *Mucor rouxii*, v6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, | *Mortierella aipina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF1 26798 | *Mus musculus* Δ6 fatty acid desaturase |
| AF1 99596, | *Homo sapiens* Δ5 desaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AY332747 | *Pavlova lutheri* Δ4 fatty acid desaturase (desl) mRNA |
| AAG36933 | *Emericella nidulans* oleate Δ 12 desaturase |
| AF1 10509, | *Mortierella alpina* Δ12 fatty acid desaturase mRNA |
| AAL13300 | *Mortierella alpina* Δ12 fatty acid desaturase |
| AF417244 | *Mortierella alpina* ATCC 16266 Δ12 fatty acid desaturase |
| AF161219 | *Mucor rouxii* Δ12 desaturase mRNA |
| X86736 S | *piruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| NP_441622, | *Synechocystis* sp. PCC 6803 Δ15 desaturase |
| AAL36934 | *Perilla frutescens* Δ15 desaturase |

Additionally, the patent literature provides many additional DNA sequences of genes (and/or details concerning several of the genes above and their methods of isolation) involved in polyunsaturated fatty acid production. See, for example: U.S. Pat. No. 5,968,809 (Δ6 desaturases); U.S. Pat. Nos. 5,972,664 and 6,075,183 (Δ5 desaturases); WO 91/13972 and U.S. Pat. No. 5,057,419 (Δ9 desaturases); WO 93/1 1245 (Δ15 desaturases); WO 94/1 1516, U.S. Pat. No. 5,443,974 and WO 03/099216 (Δ12 desaturases); U.S. 2003/0196217 A1 (Δ17 desaturase); WO 02/090493 (Δ4 desaturases); and WO 00/12720 and U.S. 2002/01 39974A1 (elongases).

The term "desaturase" refers to a polypeptide component of a multi-enzyme complex that can desaturate, i.e., introduce a double bond in one or more fatty acids to produce a mono- or polyunsaturated fatty acid or precursor of interest. Some desaturases have activity on two or more substrates. It may be desirable to empirically determine the specificity of a fatty acid desaturase by transforming a suitable host with the gene for the fatty acid desaturase and determining its effect on the fatty acid profile of the host.

In the context of the present invention a ω3 desaturase catalyzes the conversion of LA to ALA (WO 2008022963-A 30 28 Feb. 2008; FB753570)

In the context of the present invention a 46 desaturases catalyzes the conversion of ALA to SDA and also LA to GLA. A6-Desaturases are described in WO 93/06712, U.S. Pat. Nos. 5,614,393, 5,614,393, WO 96/21022, WO0021557 and WO 99/271 11 and their application to production in transgenic organisms is also described, e. g. in WO 9846763, WO 9846764 and WO 9846765. In one embodiment, the A6-desaturase used in the present invention is derived from *Ostreococcus*, preferably OtD6 from *Ostreococcus tauri* (Domergue et al. Biochem. J. 389 (PT 2), 483-490 (2005); AY746357). In one embodiment, the A6-desaturase is encoded by a polynucleotide sequence that has at least 50, 60, 70, 80, 85, 90, 95, 97, 99% or 100% identity to SEQ ID NO:1. In another embodiment, the Δ6-desaturase comprises an amino acid sequence that has at least 50, 60, 70, 80, 85, 90, 95, 97, 99% or 100% identity to SEQ ID NO:2.

In the context of the present invention a 45 desaturase catalyzes the conversion of ETA to EPA. In one embodiment, the Δ5-desaturase used in the present invention is derived from *Thraustochytrium* sp. Preferably the Δ5-desaturase is ToΔ5 derived from *Thraustochytrium* sp. (Qiu et al. J Biol Chem. 2001 Aug. 24; 276 (34): 31561-6; AF489588). In one embodiment, the Δ5-desaturase is encoded by a polynucleotide sequence that has at least 50, 60, 70, 80, 85, 90, 95, 97, 99% or 100% identity to SEQ ID NO:5. In another embodiment, the Δ5-desaturase comprises an amino acid sequence that has at least 50, 60, 70, 80, 85, 90, 95, 97, 99% or 100% identity to SEQ ID NO:6.

In the context of the present invention a Δ12 desaturases catalyzes the conversion OA to LA. In one embodiment, the A12-desaturase used in the present invention is PEA 12 derived from *Phytophthora*, preferably *Phytophthora sojae* (WO 2006100241 A2; CS423998). In one embodiment, the A12-desaturase is encoded by a polynucleotide sequence that has at least 50, 60, 70, 80, 85, 90, 95, 97, 99% or 100% identity to SEQ ID NO:11. In another embodiment, the Δ 12-desaturase comprises an amino acid sequence that has at least 50, 60, 70, 80, 85, 90, 95, 97, 99% or 100% identity to SEQ ID NO: 12.

In the context of the present invention a Δ4 desaturase catalyzes the conversion of DPA to DHA. In one embodiment embodiment, the A4-desaturase is derived from *Thraustochytrium* sp (ATCC21685). In one embodiment, the A4-desaturase is encoded by a polynucleotide sequence that has at least 50, 60, 70, 80, 85, 90, 95, 97, 99% or 100% identity to SEQ ID NO: 17. In another embodiment, the Δ4-desaturase comprises an amino acid sequence that has at least 50, 60, 70, 80, 85, 90, 95, 97, 99% or 100% identity to SEQ ID NO: 18.

In another embodiment the Δ4-desaturase is EhD4 derived from *Emiliana huxleyi* (Sayanova et al. Phytochemistry. 201 1 May; 72 (7): 594-600). In one embodiment, the A4-desaturase is encoded by a polynucleotide sequence that has at least 50, 60, 70, 80, 85, 90, 95, 97, 99% or 100% identity to SEQ ID 15. In another embodiment, the A4-desaturase comprises an amino acid sequence that has at least 50, 60, 70, 80, 85, 90, 95, 97, 99% or 100% identity to SEQ ID NO: 16.

The term "eiongase" refers to a polypeptide that can elongate a fatty acid carbon chain to produce an acid two carbons longer than the fatty acid substrate that the eiongase acts upon.

Examples of reactions catalyzed by eiongase systems are the conversion of GLA to DGLA, SDA to ETA, ARA to DTA and EPA to DPA. In general, the substrate selectivity of eiongases is somewhat broad but segregated by both chain length and the degree and type of unsaturation.

For example, a C14/16 eiongase will utilize a C14 substrate (e.g., myristic acid), a C16/18 eiongase will utilize a C16 substrate (e.g., palmitate), a C18/20 eiongase will utilize a C18 substrate (e.g., GLA, SDA, LA, ALA) and a C20/22 eiongase (also referred to as a 45 eiongase) will utilize a C20 substrate (e.g., ARA, EPA).

Since some eiongases have broad specificity, a single enzyme may be capable of catalyzing several eiongase reactions (e.g., thereby acting as both a C16/18 eiongase and a C18/20 eiongase). It may be desirable to empirically determine the specificity of a fatty acid eiongase by transforming a suitable host with the gene for the fatty acid eiongase and determining its effect on the fatty acid profile of the host.

In the context of the present invention a 46 elongase catalyzes the conversion of SDA to ETA. In one embodiment, the Δδ-elongase used in the present invention is derived from *Physcomitrella*, and is preferably from *Physcomitrella patens*. Preferably the Δδ-elongase is PSE1 derived from *Physcomitrella patens* (Zank, et al., *Plant J.* 31 (3), 255-268 (2002); AB238914). In one embodiment, the Δδ-elongase is encoded by a polynucleotide sequence that has at least 50, 60, 70, 80, 85, 90, 95, 97, 99% or 100% identity to SEQ ID NO:3. In another embodiment, the Δδ-elongase comprises an amino acid sequence that has at least 50, 60, 70, 80, 85, 90, 95, 97, 99% or 100% identity to SEQ ID NO:4.

In the context of the present invention a Δ5 elongase catalyzes the conversion of EPA to DPA. In one embodiment, the Δ5-elongase used in the present invention is derived from *Ostreococcus*, preferably *Ostreococcus tauri*. Preferably the Δ5-elongase is OtElo5 derived from *Ostreococcus tauri* (WO 200501 231 6-A2; CS020123). In one embodiment, the Δ5-elongase is encoded by a polynucleotide sequence that has at least 50, 60, 70, 80, 85, 90, 95, 97, 99% or 100% identity to SEQ ID NO:7. In another embodiment, the Δ5-elongase comprises an amino acid sequence that has at least 50, 60, 70, 80, 85, 90, 95, 97, 99% or 100% identity to SEQ ID NO:8.

Although the particular source of a polyunsaturated fatty acid desaturase or elongase is not critical in the invention herein, it will be obvious to one of skill in the art that heterologous genes will be expressed with variable efficiencies in an alternate host. Furthermore, it may be desirable to modify the expression of particular polyunsaturated fatty acid biosynthetic pathway enzymes to achieve optimal conversion efficiency of each, according to the specific polyunsaturated fatty acid product composition of interest. A variety of genetic engineering techniques are available to optimize expression of a particular enzyme. Two such techniques include codon optimization and gene mutation, as described below. Genes produced by e.g., either of these two methods, having desaturase and/or elongase activity(s) would be useful in the invention herein for synthesis of omega-3 polyunsaturated fatty acids.

Sequence Homology or Sequence Identity

"Sequence Homology or Sequence identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, WI 5371 1). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Preferably, reference to a sequence which has a percent identity to any one of the SEQ ID NOs as detailed herein refers to a sequence which has the stated percent identity over the entire length of the SEQ ID NO referred to.

Another indication that two nucleic acid sequences are substantially identical is that the two molecules hybridize to each other under stringent conditions.

Hybridization

Hybridization is the binding of complementary strands of DNA, DNA/RNA, or RNA.

Polynucleotides that hybridize to the polynucleotide sequences provided herein may also be used in the invention. Particularly preferred are polynucleotides that hybridize under stringent conditions to the polynucleotides described herein. As herein used, the terms "stringent conditions" and "stringent hybridization conditions" mean hybridization occurring only if there is at least 90%, 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C.

The polynucleotides of the invention, may be used as a hybridization probe for RNA, cDNA and genomic DNA to isolate other genes that have a high identity, particularly high sequence identity.

Codon-Optimization

Codon degeneracy refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In the present invention, it may be desirable to modify a portion of the codons encoding the polypeptide having the relevant activity e.g., desaturase or elongase activity, to enhance the expression of the gene in camelina.

Gene Mutation

Methods for synthesizing sequences and bringing sequences together are well established in the literature. For example, in vitro mutagenesis and selection, site-directed mutagenesis, error prone PGR (Melnikov et al., Nucleic Acids Research, 27(4): 1056-1 062 (Feb. 15, 1999)), "gene shuffling" or other means can be employed to obtain mutations of naturally occurring desaturase or elongase genes. This would permit production of a polypeptide having desaturase or elongase activity, respectively, in vivo with more desirable physical and kinetic parameters for function in the host cell such as a longer half-life or a higher rate of production of a desired PUFA.

If desired, the regions of a polypeptide of interest (i.e., a desaturase or an elongase) important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR, while point mutations are made through techniques such as site-directed mutagenesis or mutagenic PCR.

Transformation

The term "transgenic" or "recombinant" is preferably understood as meaning the expression of the nucleic acids encoding the enzymes involved in omega-3 fatty acid synthesis referred to herein at an unnatural locus in the genome, i.e. preferably, heterologous expression of the nucleic acids takes place. Thus, the genes introduced in to the camelina according to the present invention are preferably derived from a different organism.

The polynucleotides encoding the enzymes (e.g., desaturase and elongase enzymes) may be introduced into expression cassettes and/or vectors. In principal, the expression cassettes can be used directly for introduction into the camelina. However, preferably the nucleic acids are cloned into expression cassettes, which are then used for transforming camelina with the aid of vectors such as *Agrobacterium.*

After their introduction into the camelina plant cell or plant, the polynucleotides used in the present invention can either be present on a separate plasmid or, advantageously, integrated into the genome of the host cell.

As used in the present context, the term "vector" refers to a nucleic acid molecule which is capable of transporting another nucleic acid to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced. Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids.

The recombinant expression vectors used in the present invention are suitable for expressing nucleic acids in a camelina host cell. The recombinant expression vectors/polynucleotides preferably comprise one or more regulatory sequences, which regulatory sequence(s) is/are operably linked with the nucleic acid sequence to be expressed.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "regulatory sequence" is intended to comprise promoters, enhancers and other expression control elements such as polyadenylation signals. These regulatory sequences are described, for example, in Goeddel: Gene Expression Technology: Methods in Enzymology 185, Academic Press, San Diego, CA (1990), or see: Gruber and Crosby, in: Methods in Plant Molecular Biology and Biotechnolgy, CRC Press, Boca Raton, Florida, Ed.: Glick and Thompson, Chapter 7, 89-108, including the references cited therein.

Examples of plant expression vectors comprise those which are described in detail in: Becker, D., Kemper, E., Schell, J., and Masterson, R. (1992) "New plant binary vectors with selectable markers located proximal to the left border", Plant Mol. Biol. 20:1 195-1 197; Bevan, M. W. (1984) "Binary *Agrobacterium* vectors for plant transformation", Nucl. Acids Res. 12:8711-8721; and Vectors for Gene Transfer in Higher Plants; in: Transgenic Plants, Vol. 1, Engineering and Utilization, Ed.: Kung and R. Wu, Academic Press, 1993, p. 15-38.

The polynucleotide/vector preferably comprises regulatory sequences which are capable of governing the expression of genes in plant cells and which are linked operably so that each sequence can fulfill its function, such as transcriptional termination, for example polyadenylation signals. Examples of polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but other terminator sequences which are functionally active in plants are also suitable.

Since plant gene expression is very often not limited to the transcriptional level, a plant expression cassette or vector preferably comprises other sequences which are linked operably, such as translation enhancers.

Plant gene expression is preferably linked operably with a suitable promoter which triggers gene expression with the correct timing or in a cell- or tissue-specific manner. Examples of promoters are constitutive promoters (Benfey et al., EMBO J. 8 (1989) 2195-2202), such as those which are derived from plant viruses, such as 35S CaMV (Franck et al., Cell 21 (1980) 285-294), 19S CaMV (see also U.S. Pat. No. 5,352,605 and WO 84/02913), or plant promoters, such as the promoter of the Rubisco subunit, which is described in U.S. Pat. No. 4,962,028. Other sequences for use in operable linkage in plant gene expression cassettes are targeting sequences, which are required for steering the gene product into its corresponding cell compartment (see a review in Kermode, Grit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmid reticulum, elaioplasts, peroxisomes and other compartments of plant cells.

Plant gene expression can also be achieved via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic acid-inducible promoter (WO 95/19443), a tetracyclin-inducible promoter (Gatz et al. (1992) Plant J. 2, 397-404) and an ethanol-inducible promoter.

Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814), the wound-inducible pinII promoter (EP-A-0 375 091) and the cis-jasmone-responsive promoter (Matthes M C, Bruce T J, Ton J, Verrier P J, Pickett J A, Napier J A. The transcriptome of cis-jasmone-induced resistance in *Arabidopsis thaliana* and its role in indirect defence. Planta. 2010 October; 232 (5): 1163-80).

Especially preferred are those promoters which bring about the gene expression in tissues and organs in which the biosynthesis of fatty acids, lipids and oils takes place, in seed cells, such as cells of the endosperm and of the developing embryo. Examples of such promoters are the oilseed rape napin promoter (U.S. Pat. No. 5,608,152), the *Vicia faba* USP promoter (Baeumlein et al., Mol Gen Genet, 1991, 225 (3): 459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2): 233-9). It is also envisaged that a mesocarp-specific promoter could direct the synthesis of the omega-3 trait in oil palm and similar crops.

Other promoters are those which bring about a plastid-specific expression, since plastids constitute the compartment in which the precursors and some end products of lipid biosynthesis are synthesized. Examples of promoters, such as the viral RNA polymerase promoter, are described in WO 95/16783 and WO 97/06250, and the clpP promoter from *Arabidopsis*, described in WO 99/46394.

To ensure the stable integration of the biosynthesis genes into the transgenic plant over a plurality of generations, it is usually necessary for each of the nucleic acids which encodes a protein of interest to be expressed under the control of a separate promoter, preferably a promoter which differs from the other promoters, since repeating sequence motifs can lead to instability of the T-DNA, or to recombination events. However, it is also possible to insert a plurality of nucleic acid sequences behind a promoter and, if appropriate, before a terminator sequence. Here, the insertion site, or the sequence, of the inserted nucleic acids in the expression cassette is not of critical importance, that is to say a nucleic acid sequence can be inserted at the first or last position in the cassette without its expression being substantially influenced thereby.

Preferably, each gene introduced into the camelina plant or cell is under the control of a specific promoter.

Vector DNA can be introduced into cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, NY, 1989) and other laboratory textbooks such as Methods in Molecular Biology, 1995, Vol. 44, *Agrobacterium* protocols, Ed.: Gartland and Davey, Humana Press, Totowa, New Jersey.

Transformation systems for camelina are known in the art. For example, US 2009/0151023 describe a method which involves:

(a) Providing sterilized *Camelina sativa* seeds collected from a plants grown in controlled conditions;
(b) Germinating the seeds on agar in sterilized conditions and growing in vitro seedlings;
(c) Obtaining explants from the in vitro grown seedlings;
(d) Inoculating the explants with *Agrobacterium tumefaciens* strain containing at least one recombinant DNA construct;
(e) Cocultivating the explant with the *Agrobacterium* strain;
(f) Transferring the explants to a callus forming medium, said medium being supplemented with hormones and containing 2% sucrose;
(g) Transferring the explants to a shoot regeneration medium, said medium being supplemented with hormones and containing 2-6% sucrose;
(h) Transferring the shoots to a root elongation medium, said medium being supplemented with hormones and containing 1-4%; and
(i) Transferring the regenerated shoots into soil and growing them to transgenic *Camelina sativa* plants.

The methods for transforming *Camelina* disclosed in US 2009/0151028 and US 2009/0151023 are incorporated herein by reference.

Transgenic plants which comprise the polyunsaturated fatty acids synthesized in the process according to the invention can advantageously be marketed directly without there being any need for the oils, lipids or fatty acids synthesized to be isolated.

Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant. In this context, the seed comprises all parts of the seed such as the seed coats, epidermal cells, seed cells, endosperm or embryonic tissue.

The compounds produced in the process according to the invention can also be isolated from the organisms, advantageously plants, in the form of their oils, fats, lipids and/or free fatty acids. This can be done via pressing or extraction of the *Camelina* plant parts, preferably the plant seeds. In this context, the oils, fats, lipids and/or free fatty acids can be obtained by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvents such as warm hexane. Thereafter, the resulting products are processed further, i.e. refined. In this process, substances such as the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigment remaining in the product, the products are subjected to bleaching, for example using filler's earth or active charcoal. At the end, the product is deodorized, for example using steam.

Growing

In the case of plant (including plant tissue or plant organs) or plant cells, "growing" is understood as meaning, for example, the cultivation on or in a nutrient medium, or of the intact plant on or in a substrate, for example in a hydroponic culture, potting compost or on arable land.

Further preferred features and embodiments of the present invention will now be described by way of non-limiting example and with reference to the accompanying drawings in which:

FIG. 2 shows a schematic of the vector constructs used for *Camelina* transformation.

FIG. 6 shows the distribution of acyl chains within phosphatidylcholinie of wild type and *Camelina* lines transformed with the five gene construct BC.

FIG. 7 shows the distribution of acyl chains within phosphatidylethanolamine of wild type and *Camelina* lines transformed with the five gene construct BC.

FIG. 8 shows the distribution of acyl chains within phosphatidic acid and phosphoinositol of wild type and *Camelina* lines transformed with the five gene construct BC.

FIG. 9 shows the distribution of acyl chains within phosphatdylserine acid and phosphatidylglycerol of wild type and *Camelina* lines transformed with the five gene construct BC.

FIGS. 10 and 11 show the acyl-CoA pool of *Arabidopsis* and transgenic *Camelina* seeds harvested at mid-stage of seed development.

EXAMPLE 1—MATERIALS AND METHODS

Fatty-Acid Analysis

Figure 1:
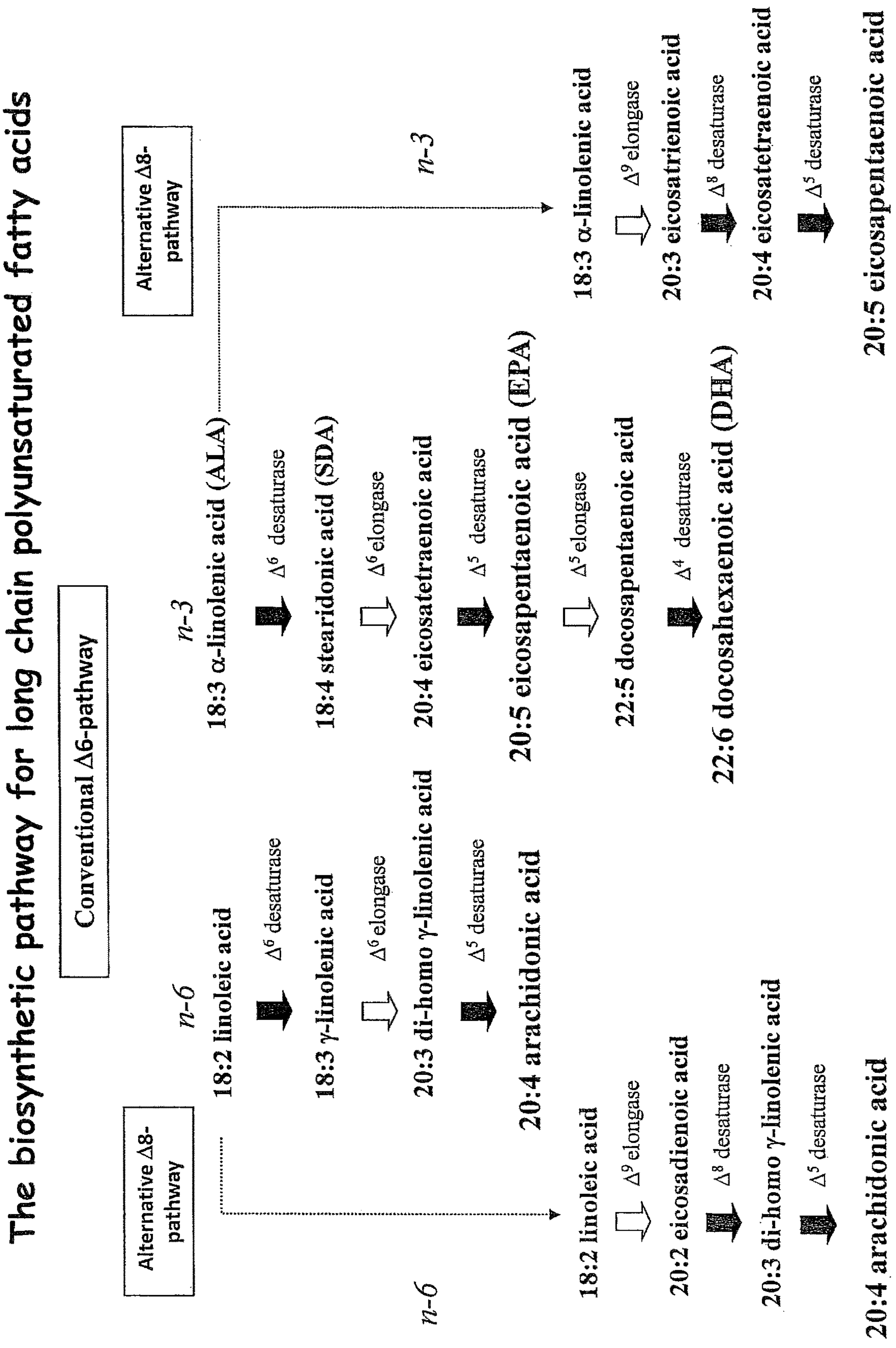
FIG. 1 is a schematic showing the biosynthesis pathway for long chain polyunsaturated fatty acids.

Fatty acids were extracted and methylated as described Sayanova et al., (1997) Proc Natl Acad Sci USA. 1997 Apr. 15; 94 (8): 421 1-6 and Sayanova et al., (2003) FEBS Lett. 2003 May 8; 542 (1-3): 100-4. Methyl ester derivatives of total fatty acids extracted were analysed by GC and GC-MS. Data presented as representative numbers derived from replicated analysis.

Acyl-CoA Profiling

Twenty-milligrams of developing (15 days after flowering) seed material were collected, frozen in liquid nitrogen and extracted after Larson and Graham 2001 (Larson T R, Graham I A. (2001), Plant J. 2001 January; 25 (1): 1 15-25), for reverse-phase LC with either quantitative analysis of fluorescent acyl-etheno-CoA derivatives or with electrospray ionization tandem mass spectrometry (multi reaction monitoring) in positive ion mode For the analysis of etheno-CoA derivatives HPLC (Agilent 1200 LC system; Phenomenex LUNA 150-2 mm C18 (2) column) was performed using the methodology and gradient conditions described previously (Larson and Graham 2001); whilst LC-MS/MS+ MRM analysis followed the methods described by Haynes et al. 2008 (Agilent 1200 LC system; Gemini C18 column, 2 mm inner diameter, 150 mm with 5 mm particles). For the purpose of identification and calibration, standard acyl-CoA esters with acyl chain lengths from C14 to C20 were purchased from Sigma as free acids or lithium salts.

Lipid Profiling

The molecular species of TAGs and PLs were analysed by electrospray ionisation triple quadrupole mass spectrometry (API 4000 QTRAP; Applied Biosystems). The molecular species of polar lipid were defined by the presence of a head-group fragment and the mass/charge of the intact lipid ion formed by ESI (Welti et al., 2002, J Biol Chem. 2002 Aug. 30; 277 (35): 31 994-2002. Devaiah et al., 2006, Phytochemistry. 2006 September; 67 (1 7): 1907-24. with modifications described by Xiao et al. 2010; Plant Cell. 2010 May; 22 (5): 1463-82.). Such tandem ESI-MS/MS precursor and product ion scanning, based on head group fragment, do not determine the individual fatty acyl species. Instead, polar lipids are identified at the level of class, total acyl carbons, and total number of acyl carbon-carbon double bonds. Polar lipids were quantified in comparison with a series of polar lipid internal standards. Triacylglycerols (TAGs) measured after Krank et al. (2007, Methods Enzymol. 2007; 432:1-20) were defined by the presence of one acyl fragment and the mass/charge of the ion formed from the intact lipid (neutral loss profiling). This allows identification of one TAG acyl species and the total acyl carbons and total number of acyl double bonds in the other two chains. The procedure does not allow identification of the other two fatty acids individually nor the positions (sn-1, sn-2, or sn-3) that individual acyl chains occupy on the glycerol. TAGs were quantified in a manner similar to the polar lipids, including background subtraction, smoothing, integration, isotope deconvolution and comparison of sample peaks with those of the internal standard (using LipidView, Applied Biosystems). However, whereas polar lipids within a class exhibit similar mass spectral response factors, the mass spectral responses of various TAG species are variable, owing to differential ionization of individual molecular TAG species. In the data shown herein, no response corrections were applied to the data. The data were normalized to the internal standards tri15:0 and tri19:0.

EXAMPLE 2—PRODUCTION OF EPA IN TRANSGENIC CAMELINA

We were interested in engineering the accumulation of bona fide omega-3 LC-PUFAs normally associated with fish oils such as eicosapentaenoic acid (EPA; $20{:}5^{\Delta5,8,11,14,17}$) and docosahexaenoic acid (DHA; $22{:}6^{\Delta4,7,10,13,16,19}$). To that end, a modular reconstruction of their biosynthetic pathway (FIG. 1) was undertaken in transgenic *Camelina*. The heterolologous biosynthetic activities were all placed under the regulatory control of common seed-specific promoters. In addition, given the variation in codon-usage observed between angiosperms and marine algae, a number of genes were resynthesised with codon-optimisation for expression in Cruciferae.

Constructs Design

Four constructs containing from 3- to 7-gene cassettes were built using the Gateway® recombination system (Invitrogen). Respective genes were inserted. as NcoI/PacI fragments into the promoter/terminator cassettes and then moved into pENTRY vectors (FIG. 2). As shown, the simplest (MC) construct contained a three expression cassettes, comprising 1) a seed specific promoter (the sucrose binding protein SBP1800 promoter), OiΔ6, *Ostreococcus*

*tauri* Δ6-desaturase gene (Domergue et al. Biochem. J. 389 (PT 2), 483-490 (2005); AY746357) and CatpA, terminator; 2) a seed specific promoter (USP1 promoter (Baumlein et al. 1991 Mol Gen Genet. 1991 March; 225 (3): 459-67), PSE1, a Δ6 fatty acid elongase from *Physcomitrella patens* (Zank. et al., Plant J. 31 (3), 255-268 (2002); AB238914) and CaMV35S terminator; 3) a seed specific promoter (CnI, a conlininl promoter (Truksa 2003; Plant Physiol Biochem 41:141-147), TcA5, a A5-desaturase from *Thraustochytrium* sp. (Qiu et al. J Biol Chem. 2001 Aug. 24; 276 (34): 31561-6) and OCS, a terminator region of OCS, octopin synthase gene of *A. tumefaciens*.

The BC construct contained five-gene cassettes including the same 3 gene cassettes as in the MC described above plus two additional gene cassettes consisting of PsA12, a Δ12-desaturase gene from *Phytophtora sojae* (see above) and Piω3, a 03 desaturase gene from *Phytophtora infestans* (Wu et al., 2005 Nat Biotechnol. 2005 August; 23 (8): 1013-7) flanked by Np, a BnNapin promoter and E9 terminator regions.

To build DHA-1 construct we combined BC construct with additional two-gene cassettes, containing OtElo5, an *Ostreococcus tauri* Δ5 fatty acid elongase (Meyer et al., J Lipid Res. 2004 October; 45 (10): 1899-909) and EhA4, a Δ4-desaturase from *Emiliania huxleyi* (Sayanova et al. 201 1 Phytochemistry. 201 1 May; 72 (7): 594-600) flanked by napin promoters and OCS terminators.

Synthesis of EPA in Transgenic Camelina

In a first iteration, the simplest 3-gene construct (MC) was introduced into transgenic *Camelina* using standard floral infiltration technique to infect inflorescences with *Agrobacterium tumefaciens* strains carrying binary transformation vectors. Table 2 exemplifies the accumulation of non-native omega-3 long chain polyunsaturated fatty acids such as eicosapentaenoic acid (EPA). Total fatty acid composition of seeds from wild-type and transgenic plants of *C. sativa* lines expressing MC construct are shown below, confirming the presence of EPA in transgenics in the range 12.9-17.3% of total seed fatty acids. Note the complete absence of this fatty acid from the wildtype non-transgenic control.

TABLE 2

| | 16:0 | 18:0 | 18:1 | LA | GLA | ALA | SDA | 20:1 | DHGLA | ARA | ETA | EPA | Others |
|---|---|---|---|---|---|---|---|---|---|---|---|---|---|
| Wt | 7.0 | 3.1 | 15.1 | 21.2 | 0.0 | 29.6 | 0.0 | 14.1 | 0.0 | 0.0 | 0.0 | 0.0 | 9.9 |
| Line2 | 9.3 | 5.0 | 4.7 | 24.7 | 1.8 | 12.2 | 1.8 | 7.8 | 0.6 | 2.4 | 2.0 | 16.8 | 10.9 |
| Line3 | 9.3 | 4.9 | 6.4 | 25.6 | 2.1 | 13.4 | 2.0 | 8.3 | 0.7 | 2.0 | 1.8 | 12.9 | 10.6 |
| Line4 | 9.2 | 5.6 | 4.1 | 21.3 | 1.4 | 13.5 | 1.3 | 6.2 | 1.5 | 2.2 | 5.1 | 17.3 | 11.3 |

In a second iteration of engineering *Camelina* with the capacity to accumulate high levels of EPA, we transformed C. *Sativa* with the 5-gene construct BC, again by floral infiltration. As shown in Table 3 below, the total fatty acid composition of T2 seeds from transgenic plants of *C. sativa* expressing BC construct contains very high levels of EPA (in the range 20.0-30.7%). Moreover, as shown in Table 4 below, it was also possible to obtain EPA at a level of 30.7% EPA. This fatty acid is totally absent from WT controls.

TABLE 3

| | | | | | | | | | | | | | | EPA (MOL %) | | |
|---|---|---|---|---|---|---|---|---|---|---|---|---|---|---|---|---|
| | 16:0 | 18:0 | 18:1 | 18:2 | GLA | ALA | SDA | 20:1 | DHGLA | ARA | 20:3n3 | ETA | EPA | Others | Sum | Average | SD |
| 162a | 9.8 | 7.6 | 4.6 | 18.3 | 2.4 | 10.8 | 1.5 | 6.5 | 0.5 | 2.0 | 1.6 | 2.4 | 25.0 | 7.0 | 100.0 | | |
| 162b | 8.6 | 7.1 | 5.0 | 18.7 | 3.6 | 11.4 | 2.3 | 7.4 | 0.5 | 1.8 | 1.4 | 2.2 | 22.8 | 7.1 | 100.0 | | |
| 162c | 11.3 | 7.0 | 4.9 | 20.4 | 4.0 | 9.4 | 2.1 | 5.3 | 0.6 | 1.9 | 1.3 | 2.0 | 24.0 | 5.8 | 100.0 | 23.9 | 1.1 |
| 26a | 9.9 | 6.2 | 4.0 | 19.1 | 1.9 | 10.3 | 1.1 | 6.4 | 0.8 | 2.1 | 1.6 | 3.5 | 26.0 | 7.0 | 100.0 | | |
| 26b | 8.9 | 5.6 | 4.5 | 18.6 | 1.2 | 14.9 | 0.8 | 7.7 | 1.4 | 2.0 | 1.5 | 4.7 | 21.6 | 6.6 | 100.0 | | |
| 26c | 9.2 | 5.8 | 4.8 | 18.6 | 1.6 | 14.9 | 1.1 | 7.3 | 1.2 | 1.9 | 1.5 | 4.2 | 21.6 | 6.3 | 100.0 | 23.1 | 2.6 |
| 169a | 10.3 | 5.4 | 4.8 | 19.8 | 1.0 | 15.0 | 0.7 | 6.4 | 1.3 | 1.8 | 1.6 | 4.6 | 21.3 | 6.0 | 100.0 | | |
| 169b | 11.3 | 6.7 | 4.0 | 18.0 | 1.2 | 14.4 | 0.8 | 5.8 | 1.1 | 16 | 1.6 | 4.5 | 22.4 | 6.5 | 100.0 | | |
| 169c | 11.3 | 6.5 | 4.7 | 19.9 | 2.2 | 13.5 | 1.3 | 6.5 | 1.3 | 1.9 | 1.4 | 4.1 | 18.9 | 6.5 | 100.0 | 20.9 | 1.8 |
| 158a | 8.5 | 8.0 | 5.3 | 20.2 | 3.5 | 10.7 | 2.0 | 7.2 | 0.6 | 1.9 | 1.3 | 2.5 | 21.3 | 7.0 | 100.0 | | |
| 158b | 10.4 | 9.0 | 5.0 | 19.5 | 5.9 | 8.1 | 3.1 | 6.4 | 0.6 | 1.8 | 1.2 | 1.8 | 19.0 | 8.2 | 100.0 | | |
| 158c | 8.9 | 8.5 | 5.2 | 19.8 | 3.6 | 9.8 | 1.9 | 6.6 | 0.5 | 2.1 | 1.3 | 2.3 | 21.6 | 7.8 | 100.0 | 20.6 | 1.4 |
| 216a | 7.6 | 8.1 | 5.3 | 21.5 | 2.1 | 11.2 | 1.1 | 8.1 | 0.6 | 19 | 1.5 | 2.5 | 19.8 | 8.5 | 100.0 | | |
| 216b | 7.8 | 7.7 | 5.3 | 21.2 | 2.4 | 10.9 | 1.2 | 7.9 | 0.6 | 2.0 | 1.6 | 2.4 | 20.7 | 8.5 | 100.0 | | |
| 216c | 7.4 | 7.8 | 5.2 | 21.3 | 1.8 | 11.2 | 1.0 | 8.1 | 0.6 | 2.0 | 1.6 | 2.6 | 20.8 | 8.7 | 100.0 | 20.4 | 0.5 |
| 29a | 9.2 | 6.3 | 4.9 | 21.2 | 1.5 | 13.3 | 0.7 | 7.0 | 0.9 | 2.1 | 1.7 | 3.3 | 21.2 | 6.6 | 100.0 | | |
| 29b | 8.8 | 6.8 | 5.7 | 20.8 | 1.7 | 15.5 | 1.0 | 7.7 | 1.1 | 2.0 | 1.3 | 3.5 | 17.9 | 6.3 | 100.0 | | |
| 29c | 8.6 | 6.2 | 5.1 | 20.1 | 1.5 | 14.5 | 0.8 | 8.0 | 0.8 | 2.0 | 1.5 | 3.2 | 21.1 | 6.5 | 100.0 | 20.1 | 1.9 |
| 105a | 8.6 | 8.9 | 5.3 | 20.3 | 2.3 | 10.1 | 1.2 | 7.4 | 0.5 | 2.1 | 1.6 | 2.0 | 21.0 | 8.5 | 100.0 | | |
| 105b | 8.9 | 9.8 | 5.4 | 20.3 | 3.2 | 9.8 | 1.7 | 7.2 | 0.5 | 1.9 | 1.4 | 1.8 | 19.2 | 8.9 | 100.0 | | |
| 105c | 9.2 | 10.1 | 5.5 | 20.8 | 2.2 | 8.8 | 1.0 | 7.0 | 0.6 | 2.3 | 1.5 | 1.9 | 19.8 | 9.3 | 100.0 | 20.0 | 1.0 |

TABLE 4

| | | MOL % | | 16:0 | 18:0 | 18:1 | 18:2 | GLA | ALA | SDA |
|---|---|---|---|---|---|---|---|---|---|---|
| T3 seeds | LineBBC_3_26 | 1 seed/vial | 26_10 | 10.4 | 6.3 | 4.0 | 14.2 | 2.1 | 8.2 | 1.6 |
| T3 seeds | LineBBC_3_162 | 1 seed/vial | 162_13 | 11.3 | 7.3 | 4.1 | 19.4 | 2.6 | 7.6 | 1.2 |
| T3 seeds | LineBBC_3_26 | 1 seed/vial | 26_15 | 9.9 | 7.7 | 4.2 | 17.1 | 3.0 | 9.3 | 1.4 |
| T3 seeds | LineBBC_3_26 | 1 seed/vial | 26_19 | 9.3 | 6.1 | 4.2 | 15.8 | 1.3 | 13.8 | 1.0 |
| T3 seeds | LineBBC_3_169 | 1 seed/vial | 169_16 | 10.3 | 7.2 | 4.2 | 20.7 | 1.9 | 7.8 | 0.9 |
| T3 seeds | LineBBC_3_162 | 1 seed/vial | 162_20 | 8.9 | 7.0 | 5.0 | 16.6 | 2.1 | 12.2 | 1.3 |

| | 20:1 | DHGLA | ARA | 20:3n3 | ETA | EPA | Others | Sum | | |
|---|---|---|---|---|---|---|---|---|---|---|
| T3 seeds | 6.5 | 0.3 | 1.4 | 2.1 | 2.9 | 30.7 | 9.2 | 100.0 | NVR1 | 36 |
| T3 seeds | 6.2 | 0.3 | 1.6 | 1.5 | 2.1 | 26.1 | 8.6 | 100.0 | NVR1 | 16 |
| T3 seeds | 6.8 | 0.3 | 1.6 | 1.6 | 2.8 | 25.8 | 8.4 | 100.0 | NVR2 | 6 |
| T3 seeds | 7.7 | 0.5 | 1.4 | 1.9 | 3.9 | 24.9 | 8.0 | 100.0 | NVR2 | 11 |
| T3 seeds | 6.0 | 0.5 | 1.7 | 1.8 | 2.9 | 24.9 | 9.3 | 100.0 | NVR2 | 32 |
| T3 seeds | 8.1 | 0.4 | 17 | 1.6 | 2.7 | 24.6 | 7.9 | 100.0 | NVR1 | 24 |

Targeted Lipidomic Analysis of Transgenic *Camelina* Accumulating EPA.

Figure 3:
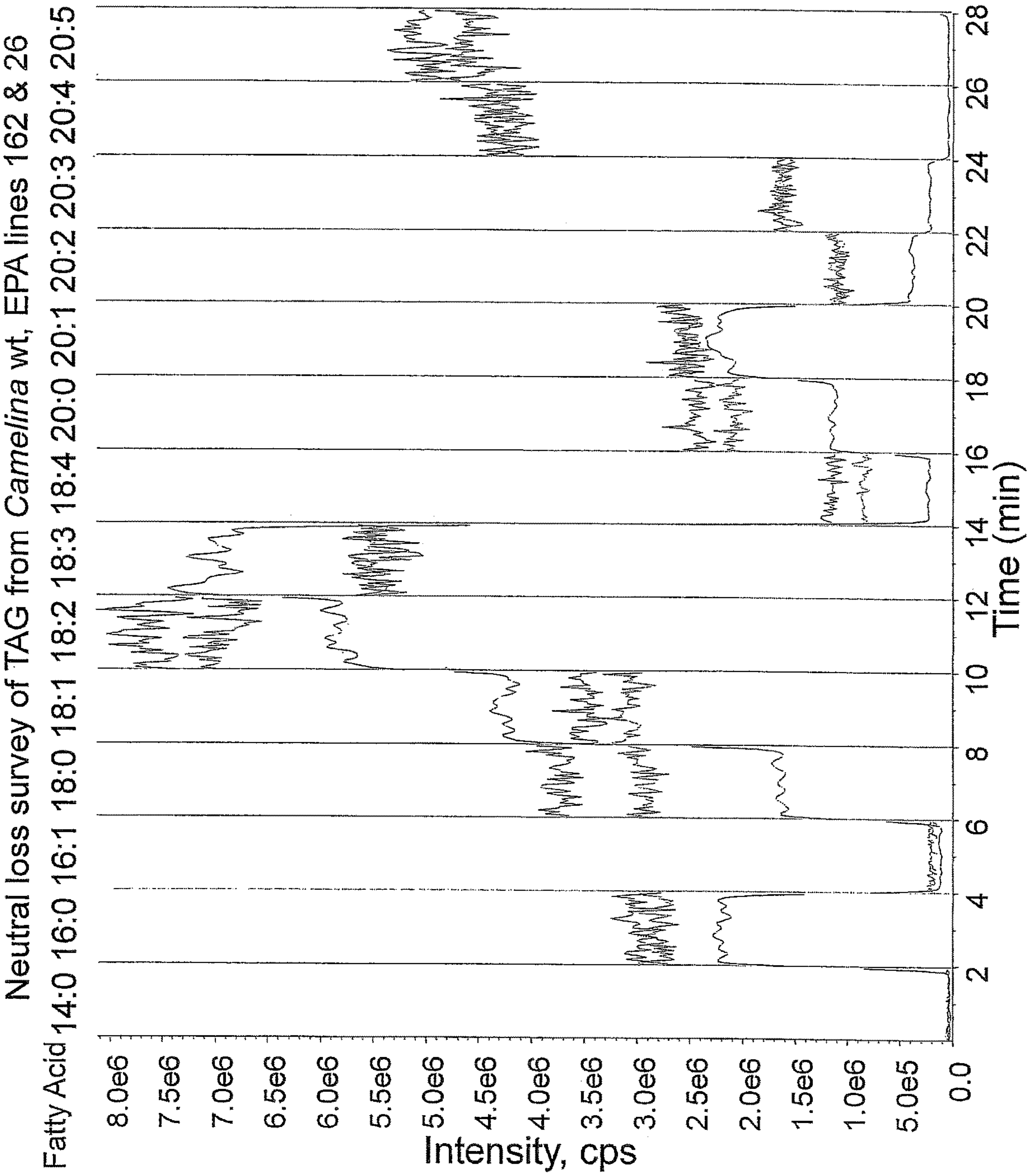
FIG. 3 shows neutral loss survey of total seed triglycerols (TAG) from wild type and *Camelina* lines transformed with the five gene construct BC.
Figure 4:
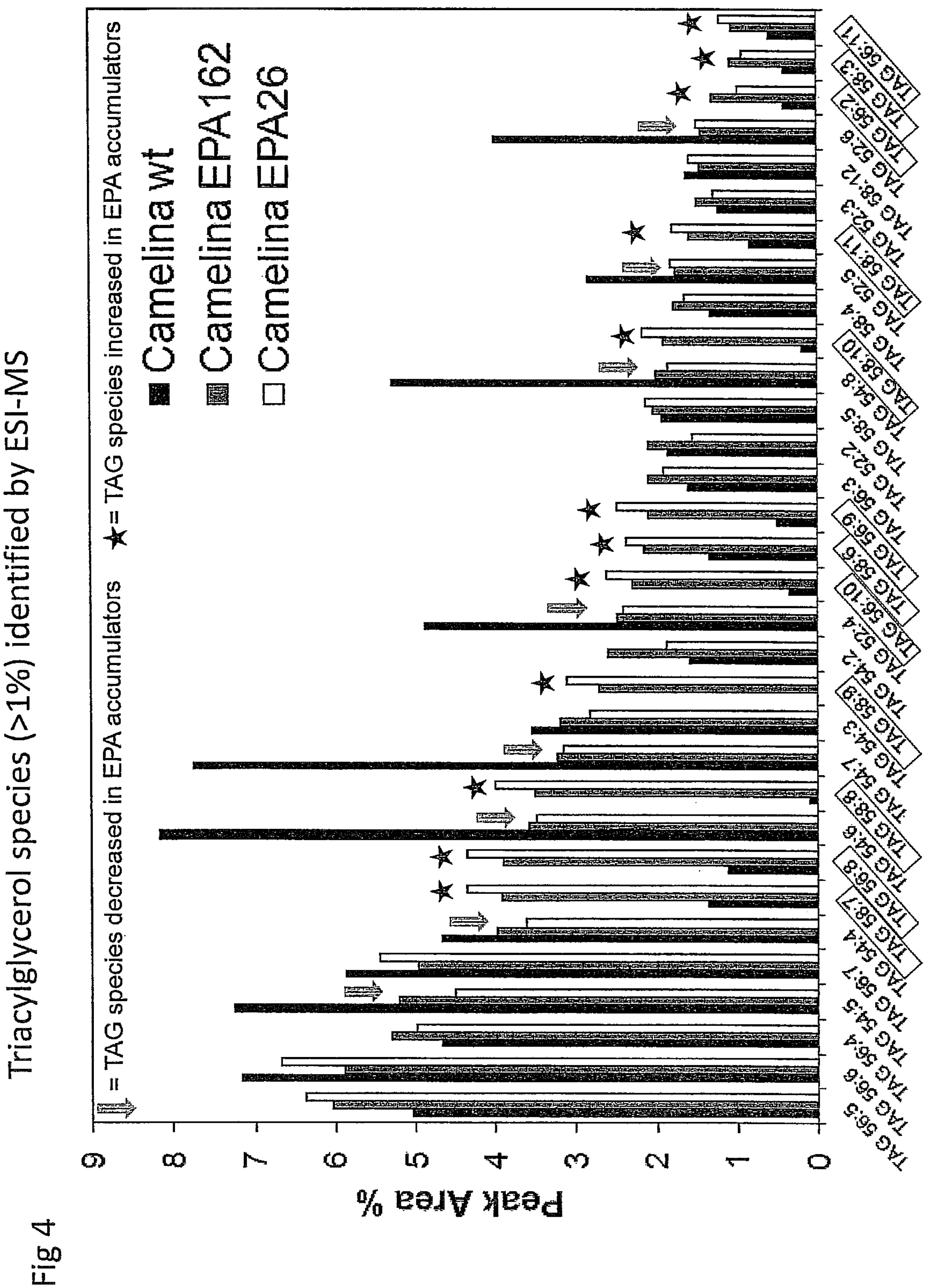
FIG. 4 shows the ESI-MS analysis of wild type and *Camelina* lines transformed with the five gene construct BC.

To provide further and more detailed characterisation of the *Camelina* plants accumulating high levels of EPA in the seed oil, detailed analysis was carried out using tandem mass spectrometry as detailed below. As shown in FIG. 3, neutral loss surveys of the total seed triacylglycerols (TAG) from either WT or two high EPA lines (162, 26-cf Table 3) confirmed the presence of EPA in TAGs from lines 162 and 26 and confirmed the complete absence of this fatty acid in WT seed oil. To further define the composition of the TAGs present in the high EPA lines, ESI-MS was used identify their molecular composition, compared with WT. As shown in FIG. 4, several novel TAG species are clearly present in lines 162 and 26 which are not present in WT, notably 58:8, 58:9 and 58:10. Given that the predominant TAG species in WT are 54:5-8, this upward shift represents the accumulation of longer chain fatty acids containing additional double bonds—i.e. EPA is accumulating at 1 (or possibly 2) positions on the glycerol backbone of TAG.

Figure 5:
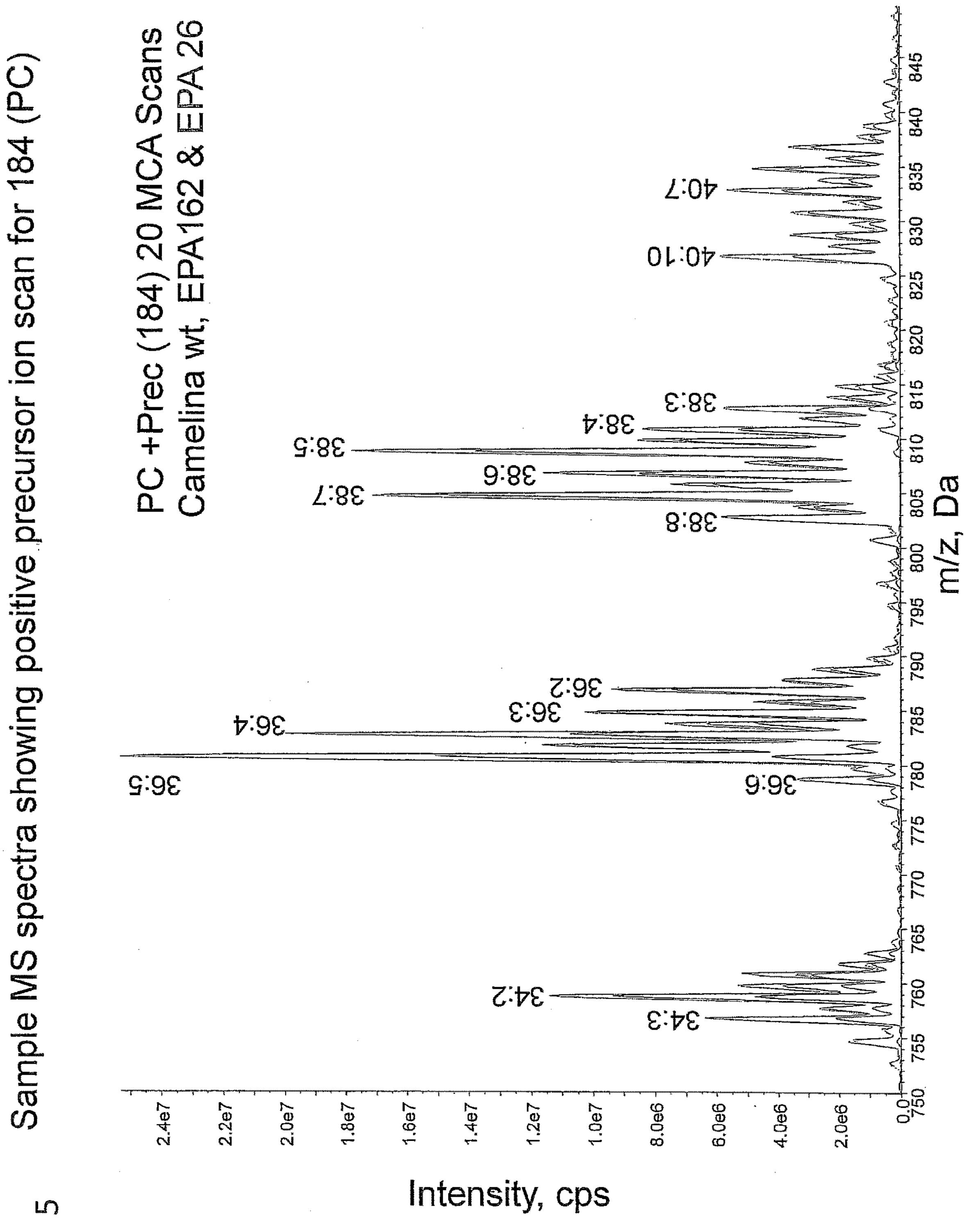
FIG. 5 shows acyl composition as determined by precursor ion scanning of phosphatidyl choline for the wild type and *Camelina* lines transformed with the five gene construct BC

As a corollary to the analysis of neutral lipids in these *Camelina* lines, we also analysed the acyi composition of phospholipids. Using precursor ion scanning, the acyl composition of phosphatidylcholine (PC, the major phospholipid present in plant seeds) was determined for WT and lines 162 and 26 (FIG. 5). Again major differences were identified between the WT and the high EPA transgenics, including the identification of a series of C38 and C40 lipids were essentially absent from WT.

This alteration to the composition of phospholipids resulting from the transgenic synthesis and accumulation of EPA was further investigated by more detailed profiling of individual phospholipid classes (FIGS. 6-9). As seen in FIG. 6, this analysis confirmed the presence of a suite of novel PC species, arising from the incorporation of EPA into this phospholipid. It is also clear that a number of endogenous PC species are reduced as a consequence of this accumulation, most notably the reduction in C36 PC species containing 1-4 double bonds. A very similar profile was observed for phosphatidylethanolamine (PE) (FIG. 8), which also showed the accumulation of novel C38 and C40 polyunsaturated species, with a concomitant reduction in the levels of C36 PE species. We profiled the other, more minor, phospholipid species (phosphatidic acid [PA], phosphoinositol [PI], phosphatidyserine [PS] and phosphatidyl lycerol [PG]) and observed some more prenounced perturbations. For example, overall levels of all PA species were increased in the transgenic lines, albeit from a very low baseline (FIG. 8). Conversely many C34 and C36 PI species were decreased in the high EPA transgenics, though these lines did also contain some novel C38 PUFA-containing species (FIG. 8). Interestingly, PS, which normally accumulates di+monounsaturated C20+ fatty acids was reduced in the transgenic lines, as were C34/36 PG species (FIG. 9). No novel C38/40 PS species could be detected in our transgenic lines, whereas novel C38 PG PUFA-containing species were observed (FIG. 9).

Acyl-CoA profiling was also used to define the composition of this key metabolic hub. As can be seen in FIGS. 10 & 11, the acyl-CoA pool of transgenic *Camelina* seeds harvested at mid-stage of seed development revealed the presence of significant levels of EPA-CoA.

EXAMPLE 3—PRODUCTION OF DHA IN TRANSGENIC CAMELINA

Having successfully engineered the significant accumulation of EPA in transgenic *Camelina* seeds, we next attempted to direct the synthesis of DHA. Since DHA is a metabolite of EPA (FIG. 1), having sufficient levels of EPA are a prerequisite for such manipulations. Using the construct detailed in FIG. 2, we generated transgenic *Camelina* plants engineered to accumulate both EPA and DHA.

Since genotyping of the T2 generation indicated that this material was not homozygous for the transgene, we decided to carry out half-seed analysis, in which a portion of the seed is subject to destructive FAMes analysis, but the residual portion containing the embryo is retained and can be used to regenerate a plant. As shown below in Table 5, the single (half) seed analysis indeed confirmed the presence of transgene nulls (samples 9-1 1) as would be expected from a non-homozygous population. However, FAMEs analysis of total seed lipids did indeed confirm the presence of EPA and DHA, the later up to levels greater than 13% of total fatty acids. The best line showing combined levels of EPA and DHA (C20+ omega-3 LC-PUFAs) was at 26.3% of total seed fatty acids. Importantly, this line contained only very low levels of the omega-6 fatty acids ARA, GLA and DHGLA and the omega-3 biosynthetic intermediates SDA, ETA and DPA. Thus this novel *Camelina* oil represents a new and valuable terrestrial source of C20+ omega-3 LC-PUFAs normally found in aquatic environments.

Table 5. Total fatty acid composition of T2 seeds from transgenic plants of *C. sativa* best lines expressing DHA-1 construct. (Half seed analysis)

Half seed analysis on T2 seeds

| MOL % | | 16:0 | 18:0 | 18:1 | 18:2 | GLA | ALA | SDA | 20:0 | 20:1 | 20:2 | DHGLA |
|---|---|---|---|---|---|---|---|---|---|---|---|---|
| BBC_OE3 | 1 | 15.0 | 7.5 | 7.2 | 23.4 | 1.6 | 6.4 | 0.9 | 3.5 | 6.7 | 1.4 | 1.3 |
| | 2 | 12.1 | 8.0 | 6.4 | 20.7 | 3.2 | 11.2 | 2.4 | 3.6 | 6.0 | 1.1 | 1.0 |
| | 3 | 15.7 | 7.5 | 5.4 | 18.5 | 2.5 | 10.4 | 2.0 | 4.0 | 6.7 | 1.3 | 1.0 |
| | 4 | 14.8 | 4.9 | 7.5 | 18.8 | 1.6 | 13.2 | 1.4 | 1.8 | 7.4 | 1.5 | 1.0 |
| | 5 | 11.1 | 4.8 | 6.5 | 23.3 | 1.9 | 14.6 | 1.3 | 2.5 | 8.5 | 1.5 | 1.5 |
| | 6 | 11.5 | 4.4 | 8.6 | 23.1 | 2.3 | 13.4 | 1.7 | 2.1 | 8.5 | 1.4 | 1.7 |
| | 7 | 11.3 | 5.0 | 6.8 | 23.4 | 2.1 | 13.7 | 1.5 | 2.5 | 8.2 | 1.3 | 1.3 |
| | 8 | 13.3 | 4.8 | 5.7 | 19.4 | 2.1 | 12.3 | 1.9 | 1.9 | 7.6 | 1.5 | 0.9 |
| | 9 | 9.8 | 3.8 | 9.3 | 23.5 | 0.2 | 27.6 | 0.2 | 2.7 | 11.6 | 24 | 0.1 |
| | 10 | 12.6 | 4.9 | 9.7 | 28.0 | 0.0 | 21.4 | 0.0 | 2.9 | 9.2 | 2.3 | 0.0 |
| | 11 | 11.9 | 3.9 | 8.6 | 23.4 | 0.0 | 26.9 | 0.0 | 2.8 | 10.6 | 2.4 | 0.0 |
| | 12 | 15.1 | 4.8 | 6.7 | 21.6 | 1.7 | 13.4 | 1.3 | 2.0 | 7.7 | 1.3 | 1.3 |
| | 13 | 13.1 | 5.4 | 6.9 | 24.8 | 2.1 | 11.0 | 1.2 | 2.7 | 8.1 | 1.2 | 1.4 |
| | 14 | 12.0 | 4.9 | 5.5 | 17.2 | 3.2 | 13.8 | 3.2 | 2.2 | 7.4 | 1.0 | 0.7 |
| | 15 | 10.7 | 8.0 | 6.1 | 21.5 | 1.9 | 15.3 | 1.9 | 4.0 | 7.6 | 1.1 | 0.8 |
| | 16 | 12.1 | 5.7 | 6.4 | 18.1 | 2.3 | 15.3 | 2.2 | 2.7 | 6.9 | 1.0 | 0.7 |
| | 17 | 10.8 | 5.4 | 7.5 | 22.5 | 1.7 | 16.4 | 1.4 | 3.2 | 7.8 | 1.3 | 1.2 |
| | 18 | 14.0 | 5.0 | 6.5 | 23.2 | 1.8 | 9.4 | 1.2 | 2.5 | 7.3 | 1.3 | 1.2 |
| | 19 | 12.6 | 4.7 | 6.5 | 21.6 | 1.8 | 14.4 | 1.5 | 2.0 | 7.5 | 1.3 | 1.0 |
| | 20 | 15.2 | 6.0 | 6.8 | 23.8 | 1.5 | 7.8 | 0.8 | 3.2 | 7.3 | 1.3 | 1.1 |

Half seed analysis on T2 seeds

| MOL % | | ARA | 20:3n3 | ETA | EPA | 22:0 | 22:1 | DPA | DHA | Others | | |
|---|---|---|---|---|---|---|---|---|---|---|---|---|
| BBC_OE3 | 1 | 1.5 | 0.9 | 1.9 | 5.3 | 0.5 | 1.0 | 1.3 | 4.4 | 8.4 | NVX1 | 7 |
| | 2 | 1.5 | 0.8 | 2.6 | 5.6 | 0.6 | 0.7 | 1.7 | 4.2 | 6.8 | NVX1 | 56 |
| | 3 | 1.3 | 0.9 | 2.6 | 5.2 | 0.6 | 0.8 | 1.4 | 4.1 | 8.1 | NVX1 | 9 |
| | 4 | 1.2 | 1.0 | 2.7 | 4.9 | 0.4 | 0.9 | 1.5 | 4.7 | 8.6 | NVX1 | 10 |
| | 5 | 1.4 | 1.1 | 3.3 | 5.2 | 0.4 | 0.9 | 1.3 | 4.3 | 4.6 | NVX1 | 57 |
| | 6 | 1.5 | 0.8 | 3.0 | 4.8 | 0.3 | 0.8 | 1.1 | 3.8 | 5.3 | NVX1 | 13 |
| | 7 | 1.5 | 1.0 | 2.8 | 5.8 | 0.4 | 1.0 | 1.3 | 5.0 | 4.2 | NVX1 | 14 |
| | 8 | 1.5 | 1.2 | 2.3 | 7.2 | 0.4 | 1.0 | 1.5 | 7.3 | 6.5 | NVX1 | 15 |
| | 9 | 0.0 | 1.1 | 0.3 | 0.4 | 0.5 | 3.4 | 0.0 | 0.3 | 3.1 | NVX1 | 58 |
| | 10 | 0.0 | 0.6 | 0.0 | 0.0 | 0.5 | 2.5 | 0.0 | 0.0 | 5.5 | NVX1 | 17 |
| | 11 | 0.0 | 1.0 | 0.0 | 0.0 | 0.5 | 3.5 | 0.0 | 0.0 | 4.4 | NVX1 | 19 |
| | 12 | 1.4 | 1.0 | 2.7 | 5.1 | 0.4 | 0.9 | 1.3 | 4.5 | 5.7 | NVX1 | 20 |
| | 13 | 1.4 | 0.9 | 2.5 | 5.6 | 0.4 | 1.0 | 1.1 | 4.4 | 4.8 | NVX1 | 21 |
| | 14 | 1.4 | 1.2 | 2.3 | 8.8 | 0.4 | 0.7 | 2.2 | 7.5 | 4.6 | NVX1 | 22 |
| | 15 | 1.2 | 1.0 | 2.5 | 4.8 | 0.6 | 1.0 | 1.8 | 5.2 | 3.0 | NVX1 | 59 |
| | 16 | 1.5 | 1.2 | 2.6 | 6.9 | 0.5 | 0.7 | 2.2 | 7.2 | 3.9 | NVX1 | 25 |
| | 17 | 1.4 | 1.1 | 3.0 | 5.2 | 0.4 | 0.7 | 1.6 | 4.4 | 2.8 | NVX1 | 26 |
| | 18 | 1.7 | 1.1 | 2.2 | 7.0 | 0.5 | 1.1 | 1.4 | 6.1 | 5.4 | NVX1 | 27 |
| | 19 | 1.4 | 1.1 | 2.6 | 5.5 | 0.4 | 1.0 | 1.6 | 5.7 | 5.6 | NVX1 | 28 |
| | 20 | 1.5 | 1.0 | 2.4 | 5.8 | 0.5 | 1.2 | 1.6 | 5.3 | 5.9 | NVX1 | 29 |

| Line | 16:0 | 18:0 | 18:1 | 18:2 | GLA | ALA | SDA | 20:0 | 20:1 | 20:2 |
|---|---|---|---|---|---|---|---|---|---|---|
| OE_33_2 | 15.9 | 5.2 | 5.8 | 16.6 | 1.6 | 7.4 | 1.4 | 0.8 | 2.7 | 1.0 |
| OE_33_24 | 13.2 | 4.2 | 5.3 | 15.7 | 2.6 | 9.2 | 2.0 | 1.1 | 4.1 | 1.0 |
| OE_33_66 | 14.0 | 4.1 | 6.0 | 15.3 | 3.5 | 9.4 | 2.9 | 0.9 | 3.5 | 0.9 |
| OE_33_11 | 15.4 | 5.2 | 6.2 | 13.2 | 4.4 | 7.5 | 3.0 | 1.2 | 4.2 | 0.7 |
| OE_33_5 | 14.5 | 5.0 | 5.8 | 15.4 | 3.1 | 10.1 | 2.3 | 1.1 | 3.7 | 0.9 |
| OE_33_89 | 13.3 | 4.2 | 6.0 | 17.6 | 3.4 | 10.4 | 2.7 | 1.1 | 4.0 | 1.1 |
| OE_33_91 | 11.8 | 3.9 | 5.3 | 16.6 | 2.4 | 12.9 | 2.3 | 1.0 | 4.1 | 1.3 |
| OE_33_27 | 12.6 | 4.5 | 5.9 | 17.1 | 2.5 | 12.0 | 2.2 | 1.2 | 4.3 | 0.0 |
| OE_33_97 | 11.9 | 4.0 | 6.4 | 17.6 | 3.1 | 10.7 | 2.4 | 1.1 | 4.2 | 1.1 |
| OE_33_13 | 13.3 | 4.9 | 5.7 | 16.9 | 2.3 | 11.2 | 1.9 | 1.2 | 4.1 | 1.2 |
| OE_33_3 | 13.8 | 4.5 | 6.0 | 18.0 | 2.2 | 11.9 | 2.0 | 1.0 | 4.0 | 1.3 |
| OE_33_90 | 11.4 | 4.0 | 5.4 | 16.9 | 2.5 | 13.2 | 2.6 | 1.2 | 4.5 | 1.3 |
| OE_33_31 | 10.6 | 4.2 | 5.6 | 16.3 | 2.7 | 13.3 | 2.3 | 1.2 | 4.4 | 1.2 |
| OE_33_4 | 15.7 | 4.4 | 5.0 | 16.7 | 1.9 | 10.5 | 1.9 | 1.1 | 3.9 | 1.5 |
| OE_33_92 | 10.8 | 4.2 | 5.3 | 16.4 | 3.1 | 14.0 | 2.6 | 1.1 | 4.0 | 1.0 |
| OE_33_15 | 12.1 | 4.8 | 5.8 | 16.3 | 2.4 | 13.1 | 2.1 | 1.3 | 4.9 | 1.0 |
| OE_33_34 | 10.9 | 4.1 | 5.9 | 18.2 | 2.8 | 12.5 | 2.5 | 1.1 | 4.2 | 1.2 |
| OE_33_19 | 10.2 | 4.5 | 6.3 | 13.4 | 4.0 | 12.8 | 3.3 | 1.4 | 5.5 | 0.8 |
| OE_33_74 | 11.8 | 4.0 | 6.0 | 19.9 | 3.2 | 11.1 | 2.3 | 1.1 | 4.2 | 1.2 |
| OE_33_44 | 11.7 | 4.5 | 6.0 | 17.1 | 2.3 | 12.4 | 2.1 | 1.3 | 4.5 | 1.4 |
| OE_33_63 | 10.7 | 4.4 | 5.9 | 17.1 | 3.2 | 12.0 | 2.4 | 1.2 | 4.4 | 1.2 |
| OE_33_23 | 12.2 | 4.3 | 6.2 | 19.0 | 2.5 | 12.6 | 1.9 | 1.1 | 4.4 | 0.0 |
| OE_33_64 | 11.1 | 4.4 | 6.2 | 18.5 | 2.8 | 10.9 | 2.0 | 1.2 | 4.4 | 1.3 |
| OE_33_77 | 10.9 | 4.2 | 6.5 | 16.5 | 4.3 | 11.6 | 3.3 | 1.1 | 4.6 | 0.9 |
| OE_33_7 | 15.1 | 5.0 | 5.8 | 16.4 | 2.3 | 11.7 | 1.9 | 1.2 | 4.5 | 1.2 |

-continued

| | | | | | | | | | | |
|---|---|---|---|---|---|---|---|---|---|---|
| OE 33_55 | 10.3 | 4.8 | 5.9 | 16.6 | 2.8 | 12.7 | 2.4 | 1.5 | 5.4 | 1.1 |
| OE_33_59 | 11.1 | 3.9 | 5.7 | 17.2 | 2.9 | 14.5 | 2.6 | 1.2 | 5.1 | 1.1 |
| OE_33_93 | 10.9 | 4.6 | 6.2 | 18.2 | 2.8 | 11.9 | 2.1 | 1.3 | 4.4 | 1.2 |

| Line | DHGLA | ARA | 20:3n3 | ETA | EPA | 22:0 | 22:1 | DPA | DHA | Others |
|---|---|---|---|---|---|---|---|---|---|---|
| OE_33_2 | 0.4 | 1.2 | 1.5 | 2.7 | 12.6 | 0.0 | 0.0 | 5.0 | 13.7 | 4.6 |
| OE_33_24 | 0.6 | 2.1 | 1.7 | 3.2 | 13.0 | 0.2 | 0.6 | 3.8 | 12.7 | 3.7 |
| OE_33_66 | 0.5 | 1.7 | 1.4 | 2.3 | 12.9 | 0.0 | 0.7 | 3.5 | 12.5 | 3.8 |
| OE_33_11 | 0.2 | 1.6 | 1.0 | 1.7 | 13.7 | 0.3 | 0.5 | 3.9 | 11.7 | 4.3 |
| OE_33_5 | 0.5 | 1.8 | 1.1 | 2.8 | 12.5 | 0.3 | 0.4 | 3.6 | 11.5 | 3.8 |
| OE_33_89 | 0.5 | 1.9 | 1.4 | 2.2 | 12.5 | 0.0 | 0.6 | 3.0 | 10.7 | 3.5 |
| OE_33_91 | 0.6 | 2.4 | 1.4 | 3.1 | 13.0 | 0.0 | 0.5 | 3.6 | 10.6 | 3.3 |
| OE_33_27 | 0.8 | 2.3 | 1.3 | 3.1 | 12.1 | 0.2 | 0.4 | 3.5 | 10.3 | 3.7 |
| OE_33_97 | 0.6 | 2.4 | 1,3 | 2.9 | 12.9 | 0.0 | 0.5 | 3.0 | 10.3 | 3.5 |
| OE_33_13 | 0.8 | 2.1 | 1.2 | 3.2 | 11.5 | 0.3 | 0.4 | 4.0 | 10.2 | 3.8 |
| OE_33_3 | 0.8 | 2.2 | 1.3 | 3.0 | 11.9 | 0.3 | 0.4 | 3.5 | 10.0 | 2.8 |
| OE_33_90 | 0.7 | 2.2 | 1.3 | 3.2 | 12.8 | 0.0 | 0.4 | 3.5 | 10.0 | 3.2 |
| OE_33_31 | 0.7 | 2.3 | 1.4 | 3.3 | 13.0 | 0.2 | 0.4 | 3.3 | 9.8 | 3.7 |
| OE_33_4 | 1.0 | 2.8 | 1.4 | 3.0 | 11.4 | 0.0 | 0.4 | 5.1 | 9.8 | 2.7 |
| OE_33_92 | 0.7 | 2.3 | 1.1 | 3.2 | 13.5 | 0.0 | 0.3 | 2.9 | 9.7 | 3.8 |
| OE_33_15 | 0.7 | 2.0 | 1.2 | 3.0 | 1.20 | 0.3 | 0.5 | 3.3 | 9.7 | 3.6 |
| OE_33_34 | 0.8 | 2.6 | 1.3 | 3.2 | 12.5 | 0.2 | 0.4 | 3.1 | 9.6 | 3.0 |
| OE_33_19 | 0.2 | 1.8 | 1,3 | 1.9 | 14.3 | 0.3 | 0.6 | 2.7 | 9.6 | 5.1 |
| OE_33_74 | 0.6 | 2.4 | 1.3 | 2.7 | 12.2 | 0.0 | 0.5 | 2.7 | 9.3 | 3.4 |
| OE_33_44 | 0.7 | 2.2 | 1.5 | 3.2 | 12.0 | 0.3 | 0.5 | 3.1 | 9.3 | 4.0 |
| OE_33_63 | 0.8 | 2.6 | 1.2 | 3.1 | 13.0 | 0.2 | 0.4 | 2.9 | 9.2 | 4.0 |
| OE_33_23 | 0.9 | 2.5 | 1.3 | 3.2 | 11.2 | 0.2 | 0.4 | 3.0 | 9.2 | 3.9 |
| OE_33_64 | 0.8 | 2.5 | 1.3 | 3.2 | 12.5 | 0.3 | 0.5 | 3.1 | 9.2 | 3.9 |
| OE_33_77 | 0.4 | 2.4 | 1.1 | 2.0 | 13.9 | 0.2 | 0.5 | 2.7 | 9.2 | 4.4 |
| OE_33_7 | 0.6 | 1.8 | 1.3 | 2.9 | 11.5 | 0.3 | 0.4 | 3.5 | 9.1 | 3.5 |
| OE 33_55 | 0.6 | 2.3 | 1.3 | 2.9 | 12.7 | 0.3 | 0.6 | 3.0 | 9.0 | 4.0 |
| OE_33_59 | 0.6 | 1.9 | 1.5 | 3.1 | 11.2 | 0.2 | 0.7 | 3.2 | 9.0 | 3.4 |
| OE_33_93 | 0.7 | 2.6 | 1.2 | 2.9 | 12.5 | 0.3 | 0.5 | 2.7 | 9.0 | 4.0 |

To further examine the feasibility of producing EPA and DHA in transgenic *Camelina* seeds, we evaluated additional activities for this capacity-4 examples are shown below.

EXAMPLE 4—EPA-B4.3

To the original MC construct (FIG. 2; comprising 1) a seed specific promoter (the sucrose binding protein SBP1800 promoter), OtA6, *Ostreococcus tauri* Δ6-desaturase gene (Domergue et al. Biochem. J. 389 (PT 2), 483-490 (2005); AY746357) and CatpA, terminator; 2) a seed specific promoter (USP1 promoter (Baumlein et al. 1991 Mol Gen Genet. 1991 March; 225 (3): 459-67), PSE1, a 46 fatty acid elongase from *Physcomitrella patens* (Zank. et al., *Plant J.* 31 (3), 255-268 (2002); AB238914) and CaMV35S terminator; 3) a seed specific promoter (Cnl, a conlininl promoter (Truksa 2003; Plant Physiol Biochem 41:141-147), TcA5, a Δ5-desaturase from *Thraustochytrium* sp. (Qiu et al. J Biol Chem. 2001 Aug. 24; 276 (34): 31561-6) and OCS, a terminator region of OCS, octopin synthase gene of *A. tumefaciens*) we added Hpw-3, a ω3 desaturase gene from *Hyaloperonospora parasitica* behind the Cnl promoter and in front of OCS, a terminator region of OCS, octopin synthase gene of *A. tumefaciens*

EXAMPLE S—EPA-B5.1

We varied the genes present in the original BC construct (FIG. 2), such that the PsA12, a A12-desaturase gene from *Phytophtora sojae* and Piw3, a 03 desaturase gene from *Phytophtora infestans* flanked by Np, a BnNapin promoter and E9 terminator regions were retained, but the activities were replaced with: 1) O809d6, a D6-desaturase from *Ostreococcus* RCC809, flanked by the Cnl conlininl seed-specific promoter and OCS, a terminator region of OCS, octopin synthase gene of *A. tumefaciens* 2) FcElo6, a Δ6 fatty acid elongase from *Fragilariopsis cylindrus* CCMP 1102, flanked by the Cnl conlininl seed-specific promoter and OCS, a terminator region of OCS, octopin synthase gene of *A. tumefaciens* and 3) EmiD5, a Δ5-desaturase from *Emiliana huxleyi* (Sayanova et al., 201 1, Phytochemistry 72:594-600) flanked by the Cnl conlininl seed-specific promoter and OCS, a terminator region of OCS, octopin synthase gene of *A. tumefaciens*

EXAMPLE 6—EPA-B5.2

We varied the genes present in the original BC construct (FIG. 2), such that the PSA12, a A12-desaturase gene from *Phytophtora sojae* and Pio3, a ω3 desaturase gene from *Phytophtora infestans* flanked by Np, a BnNapin promoter and E9 terminator regions were retained, but the activities were replaced with: 1) O809d6, a D6-desaturase from *Ostreococcus* RCC809, flanked by the Cnl conlininl seed-specific promoter and OCS, a terminator region of OCS, octopin synthase gene of *A. tumefaciens* 2) CeElo6, a Δ6 fatty acid elongase from *Caenorhabditis elegans* (Beaudoin et at., 2000*, Proc Natl Acad Sci USA.* 2000 June 6; 97 (12):6421-6) flanked by the Cnl conlininl seed-specific promoter and OCS, a terminator region of OCS, octopin synthase gene of *A. tumefaciens* 3) EmiD5, a A5-desaturase from *Emiliana huxleyi* (Sayanova et al., 201 1, Phytochemistry 72:594-600) flanked by the Cnl conlininl seed-specific promoter and OCS, a terminator region of OCS, octopin synthase gene of *A. tumefaciens.*

EXAMPLE 4—DHA-B7.2

To the original DHA-1 construct (FIG. 2), the EhD4 D4-desaturase from *Emiliana huxleyi* (Sayanova et al, 201 1) was replaced by TpDesk, a D4-desaturase from *Thalassiosira pseudonana* (Tonon et al, 2005 FEBS J. 2005 July; 272 (13): 3401-12), under the same regulatory elements (Cni1, OCS).

Half-seeds of primary T1 transgenic lines were analysed by GC-FID as described earlier (Example 1—Fatty acid analysis) and examples of the fatty acid profiles observed are shown in Table 6 below. These data indicate that the capacity of *Camelina* to produce EPA and DHA is not limited to the gene sets initially described.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

TABLE 6

| | line 16 | 16.1b | 16.1d | 16.2 | 16.3 | 18.0 | 18:1a | 18:1b | b18:2 | 18.2 | GLA | bALA | ALA | SDA | 20.0 |
|---|---|---|---|---|---|---|---|---|---|---|---|---|---|---|---|
| DHA-B7.2_1 | 5 | 2 | 1 | 0 | 0 | 4 | 6 | 1 | 1 | 15 | 5 | 0 | 19 | 5 | 3 |
| DHA-B7.2_2 | 5 | 2 | 4 | 1 | 2 | 7 | 3 | 0 | 0 | 15 | 3 | 0 | 13 | 4 | 5 |
| DHA-B7.2_3 | 5 | 2 | 3 | 0 | 1 | 5 | 3 | 0 | 1 | 12 | 6 | 0 | 17 | 9 | 4 |
| DHA-B7.2_4 | 5 | 2 | 1 | 0 | 0 | 6 | 5 | 0 | 1 | 15 | 2 | 0 | 19 | 2 | 4: |
| WILDTYPE | 5 | 4 | 2 | 0 | 1 | 4 | 5 | 0 | 0 | 14 | 1 | 0 | 27 | 0 | 4 |
| EPA-B4.3_1 | 5 | 2 | 1 | 0 | 0 | 4 | 15 | 0 | 1 | 8 | 0 | 0 | 21 | 1 | 3 |
| EPA-B4.3_2 | 4 | 0 | 0 | 0 | 0 | 3 | 14 | 0 | 0 | 14 | 0 | 0 | 35 | 0 | 2 |
| EPA-B4.3_3 | 5 | 1 | 1 | 0 | 0 | 2 | 10 | 0 | 0 | 14 | 0 | 0 | 38 | 0 | 2 |
| EPA-B5.1_1 | 6 | 1 | 0 | 0 | 0 | 4 | 9 | 0 | 0 | 20 | 2 | 0 | 30 | 5 | 3 |
| EPA-B5.1 2 | 7 | 1 | 0 | 0 | 0 | 5 | 8 | 1 | 0 | 25 | 3 | 0 | 22 | 5 | 4 |
| EPA-B5.1_3 | 6 | 1 | 0 | 0 | 0 | 5 | 10 | 1 | 0 | 24 | 2 | 0 | 27 | 4 | 3 |
| EPA-B5.1_4 | 6 | 1 | 0 | 0 | 0 | 4 | 12 | 1 | 0 | 27 | 3 | 0 | 18 | 5 | 3 |
| EPA-B5.1_5 | 5 | 1 | 0 | 0 | 0 | 3 | 12 | 1 | 0 | 23 | 2 | 0 | 25 | 5 | 3 |
| EPA-B5.1_6 | 6 | 1 | 0 | 1 | 0 | 3 | 11 | 2 | 1 | 26 | 4 | 0 | 18 | 5 | 2 |
| EPA-B5.1_7 | 7 | 1 | 0 | 1 | 0 | 4 | 7 | 1 | 0 | 24 | 0 | 0 | 29 | 1 | 4 |
| EPA-B5.1_8 | 7 | 1 | 0 | 1 | 0 | 6 | 8 | 2 | 0 | 32 | 4 | 0 | 17 | 4 | 3 |
| EPA-B5.2_1 | 7 | 2 | 0 | 0 | 0 | 5 | 7 | 1 | 0 | 27 | 2 | 0 | 16 | 6 | 0 |
| EPA-B5.2_2 | 6 | 1 | 0 | 0 | 0 | 4 | 13 | 0 | 0 | 22 | 1 | 0 | 27 | 4 | 0 |
| EPA-B5.2_3 | 7 | 2 | 0 | 0 | 0 | 4 | 6 | 0 | 0 | 22 | 2 | 0 | 22 | 6 | 0 |
| EPA-B5.2_4 | 7 | 2 | 0 | 0 | 0 | 5 | 8 | 0 | 0 | 24 | 1 | 0 | 27 | 4 | 0 |
| EPA-B5.2_5 | 5 | 1 | 0 | 0 | 0 | 3 | 15 | 0 | 0 | 24 | 1 | 0 | 24 | 4 | 0 |
| EPA-B5.2_6 | 6 | 1 | 0 | 0 | 0 | 3 | 12 | 0 | 0 | 24 | 0 | 0 | 29 | 3 | 0 |
| EPA-B5.2_7 | 7 | 2 | 0 | 0 | 0 | 5 | 6 | 0 | 0 | 19 | 2 | 0 | 22 | 4 | 0 |
| EPA-B5.2_8 | 7 | 2 | 0 | 0 | 0 | 4 | 7 | 0 | 0 | 23 | 1 | 0 | 28 | 4 | 0 |

| | 20.1 | 20.1a | 20:1c | 20.2 | DHGLA | ARA | 20.3n3 | 20.4n3 | EPA | 22.0 | 22.1 | 22.2 | DPA | DHA | 24.0 |
|---|---|---|---|---|---|---|---|---|---|---|---|---|---|---|---|
| DHA-B7.2_1 | 11 | 0 | 2 | 1 | 2 | 0 | 2 | 5 | 1 | 1 | 3 | 4 | 1 | 0 | 1 |
| DHA-B7.2_2 | 12 | 0 | 3 | 1 | 2 | 0 | 1 | 3 | 3 | 0 | 4 | 5 | 2 | 2 | 1 |
| DHA-B7.2_3 | 15 | 0 | 2 | 1 | 1 | 0 | 2 | 2 | 0 | 0 | 5 | 4 | 0 | 0 | 2 |
| DHA-B7.2_4 | 10 | 0 | 2 | 2 | 1 | 1 | 2 | 3 | 6 | 0 | 3 | 3 | 9 | 6 | 0 |
| WILDTYPE | 17 | 0 | 0 | 5 | 0 | 0 | 2 | 0 | 0 | 0 | 7 | 3 | 0 | 0 | 2 |
| EPA-B4.3_1 | 13 | 0 | 1 | 2 | 1 | 2 | 2 | 2 | 11 | 0 | 3 | 2 | 1 | 0 | 1 |
| EPA-B4.3_2 | 19 | 0 | 0 | 2 | 0 | 0 | 2 | 0 | 0 | 0 | 4 | 0 | 0 | 0 | 1 |
| EPA-B4.3_3 | 17 | 0 | 0 | 2 | 0 | 0 | 2 | 0 | 0 | 0 | 5 | 0 | 0 | 0 | 2 |
| EPA-B5.1_1 | 14 | 0 | 0 | 1 | 0 | 0 | 1 | 0 | 1 | 0 | 3 | 0 | 0 | 0 | 0 |
| EPA-B5.1 2 | 12 | 0 | 0 | 1 | 0 | 0 | 1 | 0 | 2 | 1 | 2 | 0 | 0 | 0 | 0 |
| EPA-B5.1_3 | 12 | 0 | 0 | 1 | 0 | 0 | 1 | 0 | 1 | 1 | 1 | 0 | 0 | 0 | 0 |
| EPA-B5.1_4 | 14 | 0 | 0 | 1 | 0 | 0 | 1 | 1 | 2 | 0 | 2 | 0 | 0 | 0 | 0 |
| EPA-B5.1_5 | 14 | 0 | 0 | 1 | 0 | 0 | 1 | 0 | 1 | 0 | 2 | 0 | 0 | 0 | 0 |
| EPA-B5.1_6 | 11 | 0 | 0 | 1 | 0 | 1 | 1 | 1 | 4 | 0 | 2 | 0 | 0 | 0 | 0 |
| EPA-B5.1_7 | 15 | 0 | 0 | 2 | 0 | 0 | 2 | 0 | 0 | 1 | 3 | 0 | 0 | 0 | 0 |
| EPA-B5.1_8 | 10 | 0 | 0 | 0 | 0 | 0 | 1 | 0 | 3 | 0 | 1 | 0 | 0 | 0 | 0 |
| EPA-B5.2_1 | 4 | 11 | 0 | 1 | 1 | 1 | 1 | 1 | 7 | 0 | 2 | 0 | 0 | 0 | 1 |
| EPA-B5.2_2 | 3 | 14 | 0 | 1 | 0 | 0 | 1 | 0 | 1 | 0 | 2 | 0 | 0 | 0 | 1 |
| EPA-B5.2_3 | 5 | 15 | 0 | 1 | 0 | 0 | 1 | 0 | 4 | 1 | 3 | 0 | 0 | 0 | 1 |
| EPA-B5.2_4 | 3 | 11 | 0 | 1 | 0 | 0 | 1 | 1 | 3 | 0 | 1 | 0 | 0 | 0 | 1 |
| EPA-B5.2_5 | 2 | 14 | 0 | 1 | 0 | 0 | 1 | 1 | 3 | 0 | 2 | 0 | 0 | 0 | 0 |
| EPA-B5.2_6 | 2 | 13 | 0 | 1 | 0 | 0 | 1 | 1 | 1 | 0 | 1 | 0 | 0 | 0 | 1 |
| EPA-B5.2_7 | 6 | 16 | 0 | 2 | 0 | 1 | 1 | 1 | 2 | 2 | 4 | 0 | 0 | 0 | 1 |
| EPA-B5.2_8 | 4 | 12 | 0 | 1 | 0 | 0 | 1 | 1 | 2 | 1 | 3 | 0 | 0 | 0 | 1 |

Sequences

```
   1 ATGTGTGTTGAGACCGAGAACAACGATGGAATCCCTACTGTGGAGATCGCTTTCGATGGA
  61 GAGAGAGAAAGAGCTGAGGCTAACGTGAAGTTGTCTGCTGAGAAGATGGAACCTGCTGCT
 121 TTGGCTAAGACCTTCGCTAGAAGATACGTGGTTATCGAGGGAGTTGAGTACGATGTGACC
 181 GATTTCAAACATCCTGGAGGAACCGTGATTTTCTACGCTCTCTCTAACACTGGAGCTGAT
 241 GCTACTGAGGCTTTCAAGGAGTTCCACCACAGATCTAGAAAGGCTAGGAAGGCTTTGGCT
 301 GCTTTGCCTTCTAGACCTGCTAAGACCGCTAAAGTGGATGATGCTGAGATGCTCCAGGAT
 361 TTCGCTAAGTGGAGAAAGGAGTTGGAGAGGGACGGATTCTTCAAGCCTTCTCCTGCTCAT
 421 GTTGCTTACAGATTCGCTGAGTTGGCTGCTATGTACGCTTTGGGAACCTACTTGATGTAC
 481 GCTAGATACGTTGTGTCCTCTGTGTTGGTTTACGCTTGCTTCTTCGGAGCTAGATGTGGA
 541 TGGGTTCAACATGAGGGAGGACATTCTTCTTTGACCGGAAACATCTGGTGGGATAAGAGA
 601 ATCCAAGCTTTCACTGCTGGATTCGGATTGGCTGGATCTGGAGATATGTGGAACTCCATG
 661 CACAACAAGCACCATGCTACTCCTCAAAAAGTGAGGCACGATATGGATTTGGATACCACT
 721 CCTGCTGTTGCTTTCTTCAACACCGCTGTGGAGGATAATAGACCTAGGGGATTCTCTAAG
 781 TACTGGCTCAGATTGCAAGCTTGGACCTTCATTCCTGTGACTTCTGGATTGGTGTTGCTC
 841 TTCTGGATGTTCTTCCTCCATCCTTCTAAGGCTTTGAAGGGAGGAAAGTACGAGGAGCTT
 901 GTGTGGATGTTGGCTGCTCATGTGATTAGAACCTGGACCATTAAGGCTGTTACTGGATTC
 961 ACCGCTATGCAATCCTACGGACTCTTCTTGGCTACTTCTTGGGTTTCCGGATGCTACTTG
1021 TTCGCTCACTTCTCTACTTCTCACACCCATTTGGATGTTGTTCCTGCTGATGAGCATTTG
1081 TCTTGGGTTAGGTACGCTGTGGATCACACCATTGATATCGATCCTTCTCAGGGATGGGTT
1141 AACTGGTTGATGGGATACTTGAACTGCCAAGTGATTCATCACCTCTTCCCTTCTATGCCT
1201 CAATTCAGACAACCTGAGGTGTCCAGAAGATTCGTTGCTTTCGCTAAGAAGTGGAACCTC
1261 AACTACAAGGTGATGACTTATGCTGGAGCTTGGAAGGCTACTTTGGGAAACCTCGATAAT
1321 GTGGGAAAGCACTACTACGTGCACGGACAACATTCTGGAAAGACCGCTTGA
```

SEQ ID NO: 2

(OtD6 Δ6-desaturase from *Ostreococcus tauri*)

```
MCVETENNDGIPTVEIAFDGERERAEANVKLSAEKMEPAALAKTFARRY
VVIEGVEYDVTDFKHPGGTVIFYALSNTGADATEAFKEFHHRSRKARKA
LAALPSRPAKTAKVDDAEMLQDFAKWRKELERDGFFKPSPAHVAYRFAE
LAAMYALGTYLMYARYVVSSVLVYACFFGARCGWVQHEGGHSSLTGNIW
WDKRIQAFTAGFGLAGSGDMWNSMHNKHHATPQKVRHDMDLDTTPAVAF
```

-continued

```
FNTAVEDNRPRGFSKYWLRLQAWTFIPVTSGLVLLFWMFFLHPSKALKG
GKYEELVWMLAAHVIRTWTIKAVTGFTAMQSYGLFLATSWVSGCYLFAH
FSTSHTHLDVVPADEHLSWVRYAVDHTIDIDPSQGWVNWLMGYLNCQVI
HHLFPSMPQFRQPEVSRRFVAFAKKWNLNYKVMTYAGAWKATLGNLDNV
GKHYYVHGQHSGKTA*
```

```
   1 ATGGAAGTTGTTGAGAGGTTCTACGGAGAGTTGGATGGAAAGGTTTCCCAAGGAGTGAAC
  61 GCTTTGTTGGGATCTTTCGGAGTTGAGTTGACTGATACCCCAACTACTAAGGGATTGCCA
 121 CTCGTTGATTCTCCAACTCCAATTGTGTTGGGAGTGTCTGTTTACTTGACCATCGTGATC
 181 GGAGGATTGCTTTGGATCAAGGCTAGAGATCTCAAGCCAAGAGCTTCTGAGCCATTCTTG
 241 TTGCAAGCTTTGGTGTTGGTGCACAACTTGTTCTGCTTCGCTTTGTCTCTTTACATGTGC
 301 GTGGGTATCGCTTACCAAGCTATCACCTGGAGATATTCCTTGTGGGGAAACGCTTATAAC
 361 CCAAAGCACAAGGAGATGGCTATCCTCGTTTACCTCTTCTACATGTCCAAGTACGTGGAG
 421 TTCATGGATACCGTGATCATGATCCTCAAGAGATCCACCAGACAGATTTCTTTCCTCCAC
```

-continued

481 GTGTACCACCATTCTTCTATCTCCCTTATCTGGTGGGCTATTGCTCATCATGCTCCAGGA

541 GGAGAGGCTTATTGGAGTGCTGCTCTCAACTCTGGAGTGCATGTGTTGATGTACGCTTAC

601 TACTTCTTGGCTGCTTGCTTGAGATCTTCCCCAAAGCTCAAGAACAAGTACCTCTTCTGG

661 GGAAGATACCTCACCCAATTCCAGATGTTCCAGTTCATGCTCAACTTGGTGCAAGCTTAC

721 TACGATATGAAAACCAACGCTCCATATCCACAATGGCTCATCAAGATCCTCTTCTACTAC

781 ATGATCTCCCTCTTGTTCCTCTTCGGAAACTTCTACGTGCAAAAGTACATCAAGCCATCC

841 GATGGAAAGCAAAAGGGAGCTAAGACCGAGTGA

SEQ ID NO: 4

(PSE1 Δ6-elongase from *Physcomitrella patens*)

MEVVERFYGELDGKVSQGVNALLGSFGVELTDTPTTKGLPLVDSPTPIV

LGVSVYLTIVIGGLLWIKARDLKPRASEPFLLQALVLVHNLECFALSLY

MCVGIAYQATTWRYSLWGNAYNPKHKEMAILVYLFYMSKYVEFMDTVIM

ILKRSTRQISFLHVYHHSSISLIWWAIAHHAPGGEAYWSAALNSGVHVL

MYAYYFLAACLRSSPKLKNKYLFWGRYLTQFQMFQFMLNLVQAYYDMKT

NAPYPQWLIKILFYYMISLLFLFGNFYVQKYIKPSDGKQKGAKTE*

1 ATGGGAAAAGGATCTGAGGGAAGATCTGCTGCTAGAGAGATGACTGCTGAGGCTAACGGA

61 GATAAGAGAAAGACCATCCTCATTGAGGGAGTGTTGTACGATGCTACCAACTTCAAACAC

121 CCAGGAGGTTCCATTATTAACTTCCTCACCGAGGGAGAAGCTGGAGTTGATGCTACCCAA

181 GCTTACAGAGAGTTCCATCAGAGATCCGGAAAGGCTGATAAGTACCTCAAGTCCCTCCCA

241 AAGTTGGATGCTTCTAAGGTGGAGTCTAGGTTCTCTGCTAAGGAGCAGGCTAGAAGGGAC

301 GCTATGACCAGGGATTACGCTGCTTTCAGAGAGGAGTTGGTTGCTGAGGGATACTTCGAT

361 CCATCTATCCCACACATGATCTACAGAGTGGTGGAGATTGTGGCTTTGTTCGCTTTGTCT

421 TTCTGGTTGATGTCTAAGGCTTCTCCAACCTCTTTGGTTTTGGGAGTGGTGATGAACGGA

481 ATCGCTCAAGGAAGATGCGGATGGGTTATGCATGAGATGGGACACGGATCTTTCACTGGA

541 GTTATCTGGCTCGATGATAGGATGTGCGAGTTCTTCTACGGAGTTGGATGTGGAATGTCT

601 GGACACTACTGGAAGAACCAGCATTCTAAGCACCATGCTGCTCCAAACAGATTGGAGCAC

661 GATGTGGATTTGAACACCTTGCCACTCGTTGCTTTCAACGAGAGAGTTGTGAGGAAGGTT

721 AAGCCAGGATCTTTGTTGGCTTTGTGGCTCAGAGTTCAGGCTTATTTGTTCGCTCCAGTG

781 TCTTGCTTGTTGATCGGATTGGGATGGACCTTGTACTTGCACCCAAGATATATGCTCAGG

841 ACCAAGAGACATATGGAGTTTGTGTGGATCTTCGCTAGATATATCGGATGGTTCTCCTTG

901 ATGGGAGCTTTGGGATATTCTCCTGGAACTTCTGTGGGAATGTACCTCTGCTCTTTCGGA

961 CTTGGATGCATCTACATCTTCCTCCAATTCGCTGTGTCTCATACCCATTTGCCAGTTACC

1021 AACCCAGAGGATCAATTGCATTGGCTTGAGTACGCTGCTGATCATACCGTGAACATCTCT

1081 ACCAAGTCTTGGTTGGTTACCTGGTGGATGTCTAACCTCAACTTCCAAATCGAGCATCAT

1141 TTGTTCCCAACCGCTCCACAATTCAGGTTCAAGGAGATCTCTCCAAGAGTTGAGGCTCTC

1201 TTCAAGAGACATAACCTCCCTTACTACGATTTGCCATACACCTCTGCTGTTTCTACTACC

1261 TTCGCTAACCTCTACTCTGTTGGACATTCTGTTGGAGCTGATACCAAGAAGCAGGATTGA

SEQ ID NO: 6
(TcΔ5-desaturase from *Thraustochytrium* sp.)
MGKGSEGRSAAREMTAEANGDKRKTILIEGVLYDATNFKHPGGSIINFL

TEGEAGVDATQAYREFHQRSGKADKYLKSLPKLDASKVESRFSAKEQAR

RDAMTRDYAAFREELVAEGYFDPSIPHMIYRVVEIVALFALSFWLMSKA

SPTSLVLGVVMNGIAQGRCGWVMHEMGHGSFTGVIWLDDRMCEFFYGVG

-continued

CGMSGHYWKNQHSKHHAAPNRLEHDVDLNTLPLVAFNERVVRKVKPGSL

LALWLRVQAYLFAPVSCLLIGLGWTLYLHPRYMLRTKRHMEFVWIFARY

IGWFSLMGALGYSPGTSVGMYLCSFGLGCIYIFLQFAVSHTHLPVTNPE

DQLHWLEYAADHTVNISTKSWLVTWWMSNLNFQIEHHLFPTAPQFRFKE

ISPRVEALFKRHNLPYYDLPYTSAVSTTFANLYSVGHSVGADTKKQD*

1 ATGTCTGCTTCTGGAGCTTTGTTGCCTGCTATTGCTTTCGCTGCTTACGCTTACGCTACC

61 TACGCTTATGCTTTCGAGTGGTCTCATGCTAACGGAATCGATAACGTGGATGCTAGAGAG

121 TGGATTGGAGCTTTGTCTTTGAGACTCCCTGCAATTGCTACCACCATGTACCTCTTGTTC

181 TGCCTTGTGGGACCTAGATTGATGGCTAAGAGGGAGGCTTTTGATCCTAAGGGATTCATG

241 CTCGCTTACAACGCTTACCAAACCGCTTTCAACGTTGTGGTGCTCGGAATGTTCGCTAGA

301 GAGATCTCTGGATTGGGACAACCTGTTTGGGGATCTACTATGCCTTGGAGCGATAGGAAG

361 TCCTTCAAGATTTTGTTGGGAGTGTGGCTCCATTACAACAATAAGTACCTCGAGTTGTTG

421 GATACTGTGTTCATGGTGGCTAGGAAAAAGACCAAGCAGCTCTCTTTCTTGCATGTGTAC

481 CATCATGCTTTGTTGATTTGGGCTTGGTGGCTTGTTTGTCATCTCATGGCTACCAACGAT

541 TGCATCGATGCTTATTTCGGAGCTGCTTGCAACTCTTTCATCCACATCGTGATGTACTCC

601 TACTACCTCATGTCTGCTTTGGGAATTAGATGCCCTTGGAAGAGATATATCACCCAGGCT

661 CAGATGTTGCAATTCGTGATCGTGTTCGCTCATGCTGTTTTCGTGCTCAGACAAAAGCAC

721 TGCCCTGTTACTTTGCCTTGGGCACAAATGTTCGTGATGACAAATATGTTGGTGCTCTTC

781 GGAAACTTCTACCTCAAGGCTTACTCTAACAAGTCTAGGGGAGATGGAGCTTCTTCTGTT

841 AAGCCTGCTGAGACTACTAGAGCACCTTCTGTGAGAAGAACCAGGTCCAGGAAGATCGAT

901 TGA

SEQ ID NO: 8
(OtELo5 Δ5-elongase from *Ostreococcus tauri*)
MSASGALLPAIAFAAYAYATYAYAFEWSHANGIDNVDAREWIGALSLRL

PAIATTMYLLFCLVGPRLMAKREAFDPKGFMLAYNAYQTAFNVVVLGMF

AREISGLGQPVWGSTMPWSDRKSFKILLGVWLHYNNKYLELLDTVFMVA

RKKTKQLSFLHVYHHALLIWAWWLVCHLMATNDCIDAYFGAACNSFIHI

VMYSYYLMSALGIRCPWKRYITQAQMLQEVIVFAHAVEVLRQKHCPVTL

PWAQMFVMTNMLVLFGNFYLKAYSNKSRGDGASSVKPAETTRAPSVRRT

RSRKID*

1 ATGTCATTGGCTGCTAAAGATGCAGCCTCGGCCCACTCATCCGTCTTGGACCCTAAGTAT

61 CACGGAGCTACAAATAAGTCAAGAACTGATGCAGCAGACCTTACAGTTAGTTCTATCGAC

121 ACTTCTAAGGAGATGATCATAAGGGGTCGTGTGTATGATGTCTCTGATTTTATTAAAAGG

181 CACCCGGGAGGAAGCATTATTAAACTCTCCTTAGGTTCTGATGCAACAGACGCTTATAAC

241 AACTTCCATATTAGGTCTAAAAAAGCGGATAAAATGTTGAGAGCTTTGCCAAGTAGGCCA

301 GTAGCGGATGGATTCGCTAGAGACGCTTTGTCTGCAGACTTCGAGGCCCTGAGAGCCCAA

361 CTCGAGGCCGAAGGTTACTTCGAACCGAATCTGTGGCATGTAGCTTATCGAGTTGCGGAA

421 GTCGTTGCTATGTACTGGGCGGGTATTAGACTTATCTGGGCGGGTTATTGGTTTTTAGGA

-continued

481 GCCATTGTAGCAGGAATAGCTCAGGGGAGATGCGGTTGGCTTCAGCATGAGGGTGGTCAT

541 TATTCGCTCACAGGTAATATTAAACTTGATCGACACATGCAAATGATTATCTATGGATTA

601 GGTTGCGGAATGTCCGGTTGTTATTGGAGAAACCAACATAACAAGCACCATGCGACACCG

661 CAAAAGTTGGGTGCAGATCCAGACCTTCAAACAATGCCTCTGGTTGCGTTCCATGGACTC

721 ATCGGTGCTAAGGCTAGGGGAGCAGGAAAGTCGTGGCTAGCATGGCAAGCTCCACTTTTC

781 TTTGGAGGCGTTATCACAACCCTGGTATCTTTTGGTTGGCAGTTCGTCCAACATCCAAAG

841 CACGCATTGAGAGTAGGAAACCAACTCGAATTAGGCTATATGGCTTTACGATATGCTTTA

901 TGGTATGCAGCATTCGGTCATCTTGGGCTTGGTGGTGCTTTCAGATTGTACGCTTTTTAT

961 GTGGCAGTCGGAGGTACATATATCTTCACGAACTTTGCGGTGTCTCACACACATAAGGAT

1021 GTTGTTCCACACGATAAGCATATTTCTTGGACCTTGTATTCTGCAAACCATACCACTAAT

1081 CAATCTAACACACCTCTAGTCAATTGGTGGATGGCCTATCTGAATTTTCAAATTGAACAT

1141 CACCTTTTCCCTAGCATGCCACAATATAACCATCCTAAAATCTGCGGAAGAGTGAAACAA

1201 TTGTTTGAAAAACATGGCGTAGAGTACGATGTCAGAACTTACGCGAAGTCAATGCGTGAT

1261 ACATACGTGAATCTCTTGGCTGTGGGAAATGCATCTCATTCCCTTCATCAGAGAAACGAG

1321 GGATTAACGACTAGGGAGTCTGCGGCTGTTAGAGTTACAGGTCATTGA

SEQ ID NO: 10

(EMoD5 Δ5-desaturase from *Emiliana huxleyi*)

1 MSLAAKDAASAHSSVLDPKYHGATNKSRTDAADLTVSSIDTSKEMIIRGRVYDVSDFIKR

61 HPGGSIIKLSLGSDATDAYNNFHIRSKKADKMLRALPSRPVADGFARDALSADFEALRAQ

121 LEAEGYFEPNLWHVAYRVAEVVAMYWAGIRLIWAGYWFLGAIVAGIAQGRCGWLQHEGGH

181 YSLTGNIKLDRHMQMIIYGLGCGMSGCYWRNQHNKHHATPQKLGADPDLQTMPLVAFHGL

241 IGAKARGAGKSWLAWQAPLFFGGVITTLVSFGWQFVQHPKHALRVGNQLELGYMALRYAL

301 WYAAFGHLGLGGAFRLYAFYVAVGGTYIFTNFAVSHTHKDVVPHDKHISWTLYSANHTTN

361 QSNTPLVNWWMAYLNFQIEHRLFPSMPQYNHPKICGRVKQLFEKHGVEYDVRTYAKSMRD

421 TYVNLLAVGNASHSLHQRNEGLTTRESAAVRVTGH*

SEQ ID NO: 11

(Codon-optimised PsΔ12-desaturase from *Phytophthora sojae*)

1 ATGGCTATTTTGAACCCTGAGGCTGATTCTGCTGCTAACCTCGCTACTGATTCTGAGGCT

61 AAGCAAAGACAATTGGCTGAGGCTGGATACACTCATGTTGAGGGTGCTCCTGCTCCTTTG

121 CCTTTGGAGTTGCCTCATTTCTCTCTCAGAGATCTCAGAGCTGCTATTCCTAAGCACTGC

181 TTCGAGAGATCTTTCGTGACCTCCACCTACTACATGATCAAGAACGTGTTGACTTGCGCT

241 GCTTTGTTCTACGCTGCTACCTTCATTGATAGAGCTGGAGCTGCTGCTTATGTTTTGTGG

301 CCTGTGTACTGGTTCTTCCAGGGATCTTACTTGACTGGAGTGTGGGTTATCGCTCATGAG

361 TGTGGACATCAGGCTTATTGCTCTTCTGAGGTGGTGAACAACTTGATTGGACTCGTGTTG

421 CATTCTGCTTTGTTGGTGCCTTACCACTCTTGGAGAATCTCTCACAGAAAGCACCATTCC

481 AACACTGGATCTTGCGAGAACGATGAGGTTTTCGTTCCTGTGACCAGATCTGTGTTGGCT

541 TCTTCTTGGAACGAGACCTTGGAGGATTCTCCTCTCTACCAACTCTACCGTATCGTGTAC

601 ATGTTGGTTGTTGGATGGATGCCTGGATACCTCTTCTTCAACGCTACTGGACCTACTAAG

661 TACTGGGGAAAGTCTAGGTCTCACTTCAACCCTTACTCCGCTATCTATGCTGATAGGGAG

721 AGATGGATGATCGTGCTCTCCGATATTTTCTTGGTGGCTATGTTGGCTGTTTTGGCTGCT

-continued

781 TTGGTGCACACTTTCTCCTTCAACACCATGGTGAAGTTCTACGTGGTGCCTTACTTCATT

841 GTGAACGCTTACTTGGTGTTGATTACCTACCTCCAACACACCGATACCTACATCCCTCAT

901 TTCAGAGAGGGAGAGTGGAATTGGTTGAGAGGAGCTTTGTGCACTGTGGATAGATCATTT

961 GGTCCATTCCTCGATTCTGTGGTGCATAGAATCGTGGATACCCATGTTTGCCACCACATC

1021 TTCTCCAAGATGCCTTTCTATCATTGCGAGGAGGCTACCAACGCTATTAAGCCTCTCCTC

1081 GGAAAGTTCTACTTGAAGGATACCACTCCTGTTCCTGTTGCTCTCTGGAGATCTTACACC

1141 CATTGCAAGTTCGTTGAGGATGATGGAAAGGTGGTGTTCTACAAGAACAAGCTCTAG

SEQ ID NO: 12

(PsΔ12-desaturase from *Phytophthora sojae*)
MAILNPEADSAANLATDSEAKQRQLAEAGYTHVEGAPAPLPLELPHFSL

RDLRAAIPKHCFERSFVTSTYYMIKNVLTCAALFYAATFIDRAGAAAYV

LWPVYWFFQGSYLTGVWVIAHECGHQAYCSSEVVNNLIGLVLHSALLVP

YHSWRISHRKHHSNTGSCENDEVFVPVTRSVLASSWNETLEDSPLYQLY

-continued

RIVYMLVVGWMPGYLFFNATGPTKYWGKSRSHFNPYSAIYADRERWMIV

LSDIFLVAMLAVLAALVHTFSFNTMVKFYVVPYFIVNAYLVLITYLQHT

DTYIPHFREGEWNWLRGALCTVDRSFGPFLDSVVHRIVDTHVCHHIFSK

MPFYHCEEATNAIKPLLGKFYLKDTTPVPVALWRSYTHCKFVEDDGKVV

FYKNKL*

1 ATGGCTACAAAGGAGGCTTACGTTTTCCCAACTCTCACCGAGATCAAGAGATCTCTCCCA

61 AAGGATTGCTTCGAGGCTTCTGTGCCTTTGTCTCTCTACTACACTGTGAGATGCTTGGTT

121 ATTGCTGTGGCTTTGACCTTCGGATTGAACTACGCTAGAGCTTTGCCAGAGGTTGAGTCT

181 TTCTGGGCTTTGGATGCTGCTTTGTGCACTGGATATATCCTCCTCCAGGGAATTGTGTTC

241 TGGGGATTCTTCACTGTTGGACACGATGCTGGACACGGAGCTTTCTCTAGATACCACCTC

301 TTGAACTTCGTTGTGGGAACCTTCATGCACTCTCTCATCTTGACCCCATTCGAGTCTTGG

361 AAGTTGACCCACAGACACCACCACAAGAACACCGGAAACATCGATAGAGATGAGGTGTTC

421 TACCCACAGAGAAAGGCTGATGATCACCCATTGTCCAGGAACTTGATCTTGGCTTTGGGA

481 GCTGCTTGGCTTGCTTATTTGGTGGAGGGATTCCCACCAAGAAAGGTGAACCACTTCAAC

541 CCATTCGAGCCACTTTTTGTGAGACAAGTGTCCGCTGTGGTTATCTCTTTGCTCGCTCAC

601 TTCTTCGTTGCTGGACTCTCTATCTACTTGTCTCTCCAGTTGGGACTTAAGACCATGGCT

661 ATCTACTACTACGGACCAGTTTTCGTGTTCGGATCTATGTTGGTGATTACCACCTTCTTG

721 CACCACAACGATGAGGAGACTCCATGGTATGCTGATTCTGAGTGGACTTACGTGAAGGGA

781 AACTTGTCCTCTGTGGATAGATCTTACGGTGCTCTCATCGATAACCTCTCCCACAACATC

841 GGAACTCACCAGATCCACCACCTCTTCCCAATTATCCCACACTACAAGCTCAAGAAGGCT

901 ACTGCTGCTTTCCACCAAGCTTTCCCAGAGCTTGTGAGAAAGTCCGATGAGCCAATCATC

961 AAGGCTTTCTTCAGAGTGGGAAGGTTGTATGCTAACTACGGAGTGGTTGATCAAGAGGCT

1021 AAGCTCTTCACTTTGAAGGAGGCTAAGGCTGCTACTGAAGCTGCTGCTAAGACCAAGTCT

1081 ACCTGA

SEQ ID NO: 14

(pi(w3)-desaturase from *Phytophthora infestans*)
1 MATKEAYVFPTLTEIKRSLPKDCFEASVPLSLYYTVRCLVIAVALTFGLNYARALPEVES

61 FWALDAALCTGYILLQGIVFWGFFTVGHDAGHGAFSRYHLLNFVVGTFMHSLILTPFESW

121 KLTHRHHHKNTGNIDRDEVFYPQRKADDHPLSRNLILALGAAWLAYLVEGFPPRKVNHFN

181 PFEPLFVRQVSAVVISLLABFFVAGLSTYLSLQLGLKTMAIYYYGPVFVFGSMLVITTFL

-continued

241 HHNDEETPWYADSEWTYVKGNLSSVDRSYGALIDNLSHNIGTHQIHHLFPIIPHYKLKKA

301 TAAFHQAFPELVRKSDEPIIKAFFRVGRLYANYGVVDQEAKLFTLKEAKAATEAAAKTKS

361 T*

SEQ ID NO: 15

(Codon-optimized EhD4 Δ4-desaturase from *Emiliana huxleyi*)

1 ATGGGGGGTGCAGGCGCTTCGGAAGCAGAGAGGCCAAAGTGGACAACTATCCACGGAAGA

61 CACGTTGATGTGTCAAAGTTTAGACACCCTGGAGGTAATATCATTGAATTGTTCTATGGC

121 ATGGATAGTACATCCGCTTTCGAGCAATTTCACGGACATCATAAGGGGGCATGGAAGATG

181 CTCAAGGCTCTTCCTACCAAGGAGGTTGACCCAGCTGACGTCCCACAGCAACCTCAAGAA

241 CATGTCGCGGAGATGACCAGACTTATGACATCCTGGAGAGAAAGGGGTTTATTCAAGCCT

301 CGTCCGGTTGCATCTGGCATATATGGACTTGCAGTAGTTGCTGCTATAGTTGCATGCATT

361 GCATGTGCTCCGCACGCACCGGTTCTGTCGGGGATTGGTTTAGGGTCTTGTTGGGCCCAA

421 TGCGGTTTCTTGCAGCATATGGGGGGACATAGGGAGTGGGGGGTCAGGTATTCTTTCTTG

481 CTCCAACACTTCTTTGAGGGTTTACTAAAGGGAGGATCAGCTAGCTGGTGGAGGAACAGA

541 CATAATAAGCATCATGCGAAAACCAATGTTCTTGGAGAGGATGGTGACCTTCGAACTACT

601 CCATTCTTTGCGTGGGACCCGACTCTCGCTAAAAAGGTGCCGGATTGGTCTCTGAAGACA

661 CAAGCTTTCACTTTCCTCCCAGCACTAGGAGCCTATGTTTTCGTTTTCGCTTTCACAATT

721 AGAAAATACGCTGTGGTGAAAAAACTCTGGCACGAACTTGCTCTAATGATTGCTCATTAC

781 GCAATGTTCTACTATGCCCTGCAGTTGGCTGGAGCCAGTTTGGGTTCTGGACTTGCATTT

841 TACTGCACAGGTTACGCATGGCAGGGAATCTACCTCGGATTCTTCTTCGGTTTGAGCCAC

901 TTTGCAGTCGAGAGAGTACCAAGCACAGCGACATGGCTCGAAAGCTCAATGATAGGTTCA

961 TGGCAGGGAATCTACCTCGGATTCTTCTTCGGTTTGAGCCACTTTGCAGTCGAGAGAGTA

1021 CCAAGCACAGCGACATGGCTCGAAAGCTCAATGATAGGTACGGTAGACTGGGGAGGTTCA

1081 TCTGCTTTTTGTGGTTATGTTTCTGGTTTCTTGAATATCCAAATTGAACATCACATGGCC

1141 CCTCAAATGCCTATGGAAAATCTGAGACAGATCAGGGCAGATTGTAAGGCTAGTGCTGAG

1201 AAACTCGGCTTGCCATATAGAGAGTTGTCATTCGCAGGTGCTGTCAAACTCATGATGGTA

1261 GGTCTCTGGAGGACTGGAAGAGACGAATTACAGCTCCGAAGTGATCGAAGAAAGTACTCA

1321 AGAACCCAGGCTTACATGGCGGCTGCTTCAGCTGTTGTTGAAAATCTGAAGGCAGATTAA

SEQ ID NO: 16

(EhD4 Δ4-desaturase from *Emiliana huxleyi*)

1 MGGAGASEAERPKWTTIHGRHVDVSKFRHPGGNIIELFYGMDSTSAFEQFHGHHKGAWKM

61 LKALPTKEVDPADVPQQPQEHVAEMTRLMTSWRERGLFKPRPVASGIYGLAVVAAIVACI

121 ACAPHAPVLSGIGLGSCWAQCGFLQHMGGHREWGVRYSFLLQHFFEGLLKGGSASWWRNR

181 HNKHHAKTNVLGEDGDLRTTPFFAWDPTLAKKVPDWSLKTQAFTFLPALGAYVFVFAFTI

241 RKYAVVKKLWHELALMIAHYAMFYYALQLAGASLGSGLAFYCTGYAWQGIYLGFFFGLSH

301 FAVERVPSTATWLESSMIGSWQGIYLGFFFGLSHFAVERVPSTATWLESSMIGTVDWGGS

361 SAFCGYVSGFLNIQIEHHMAPQMPMENLRQIRADCKASAEKLGLPYRELSFAGAVKLMMV

421 GLWRTGRDELQLRSDRRKYSRTQAYMAAASAVVENLKAD*

SEQ ID NO: 17
(Codon-optimized Δ4-desaturase from *Thraustochytrium* sp., ATCC21685)

1 ATGACTGTTGGATACGATGAGGAGATCCCATTCGAGCAAGTTAGGGCTCATAACAAGCCA

61 GATGATGCTTGGTGTGCTATTCATGGACACGTGTACGATGTTACCAAGTTCGCTTCTGTT

121 CATCCAGGAGGAGATATTATCTTGCTCGCTGCTGGAAAGGAAGCTACTGTGCTCTACGAG

181 ACCTACCATGTTAGAGGAGTGTCTGATGCTGTGCTCAGAAAGTACAGAATCGGAAAGTTG

241 CCAGATGGACAAGGAGGAGCTAACGAGAAGGAGAAGAGAACCTTGTCTGGATTGTCCTCT

301 GCTTCTTACTACACCTGGAACTCCGATTTCTACAGAGTGATGAGGGAGAGAGTTGTGGCT

361 AGATTGAAGGAGAGAGGAAAGGCTAGAAGAGGAGGATACGAGTTGTGGATCAAGGCTTTC

421 TTGCTCCTTGTTGGATTCTGGTCCTCTCTTTACTGGATGTGCACCCTCGATCCATCTTTC

481 GGAGCTATCTTGGCTGCTATGTCTTTGGGAGTGTTCGCTGCTTTTGTTGGAACCTGCATC

541 CAACATGATGGAAACCATGGAGCTTTCGCTCAATCTAGATGGGTTAACAAGGTGGCAGGA

601 TGGACTTTGGATATGATCGGAGCTTCTGGAATGACTTGGGAGTTCCAACATGTGTTGGGA

661 CATCACCCATACACTAACTTGATCGAGGAGGAGAACGGATTGCAAAAGGTGTCCGGAAAG

721 AAGATGGATACCAAGTTGGCTGATCAAGAGTCTGATCCAGATGTGTTCTCCACCTACCCA

781 ATGATGAGATTGCATCCATGGCATCAGAAGAGATGGTATCACAGGTTCCAGCATATCTAC

841 GGACCATTCATCTTCGGATTCATGACCATCAACAAGGTGGTGACTCAAGATGTTGGAGTG

901 GTGTTGAGAAAGAGGCTCTTCCAAATCGATGCTGAGTGCAGATATGCTTCCCCAATGTAC

961 GTTGCTAGGTTCTGGATCATGAAGGCTTTGACCGTGTTGTACATGGTTGCTCTCCCATGT

1021 TATATGCAAGGACCATGGCATGGATTGAAGCTCTTCGCTATCGCTCATTTCACTTGCGGA

1081 GAGGTTTTGGCTACCATGTTCATCGTGAACCACATTATCGAGGGAGTGTCTTACGCTTCT

1141 AAGGATGCTGTTAAGGGAACTATGGCTCCACCAAAGACTATGCATGGAGTGACCCCAATG

1201 AACAACACTAGAAAGGAGGTTGAGGCTGAGGCTTCTAAGTCTGGAGCTGTGGTTAAGTCT

1261 GTGCCATTGGATGATTGGGCTGCTGTTCAATGCCAAACCTCTGTGAACTGGTCTGTTGGA

1321 TCTTGGTTCTGGAACCATTTCTCTGGAGGACTCAACCATCAAATCGAGCATCATCTCTTC

1381 CCAGGATTGTCTCACGAGACCTACTACCACATCCAAGATGTGGTTCAATCTACCTGTGCT

1441 GAGTACGGAGTTCCATACCAACATGAGCCATCTTTGTGGACTGCTTACTGGAAGATGCTC

1501 GAACATTTGAGACAATTGGGAAACGAGGAGACTCACGAGTCTTGGCAAAGAGCTGCTTGA

SEQ ID NO: 18
(Δ4-desaturase from *Thraustochytrium* sp., ATCC21685)

1 MTVGYDEEIPFEQVRAHNKPDDAWCAIHGHVYDVTKFASVHPGGDIILLAAGKEATVLYE

61 TYHVRGVSDAVLRKYRIGKLPDGQGGANEKEKRTLSGLSSASYYTWNSDFYRVMRERVVA

121 RLKERGKARRGGYELWIKAFLLLVGFWSSLYWMCTLDPSFGAILAAMSLGVFAAFVGTCI

-continued

181 QHDGNHGAFAQSRWVNKVAGWTLDMIGASGMTWEFQHVLGHHPYTNLIEEENGLQKVSGK

241 KMDTKLADQESDPDVFSTYPMMRLHPWHQKRWYHRFQHIYGPFIFGFMTINKVVTQDVGV

301 VLRKRLFQIDAECRYASPMYVARFWIMKALTVLYMVALPCYMQGPWHGLKLFAIAHFTCG

361 EVLATMFIVNHIIEGVSYASKDAVKGTMAPPKTMHGVTPMNNTRKEVEAEASKSGAVVKS

421 VPLDDWAAVQCQTSVNWSVGSWFWNHFSGGLNHQIEHHLFPGLSHETYYHIQDVVQSTCA

481 EYGVPYQHEPSLWTAYWKMLEHLRQLGNEETHESWQRAA*

SEQ ID NO: 19

(codon optimised O809D6 Δ6-desaturase from *Ostreococcus* RCC809)

ATGGGAAAGGGAGCAAGGAACCCAGGAGCAAGGGCATGGAAGTCAACAT

TGGAGCCTCACGCAGTGGCAAAGTCATTCGATAGGAGATGGGTTAAGGT

GGATGGAGTTGAATACGATGTGACTGATTTCAAGCATCCTGGAGGTAGT

GTTATATACTACATGCTTTCTAACACAGGTGCTGATGCAACCGAAGCTT

TTAAGGAGTTCCATTACAGGAGTAAGAAAGCTAGGAAAGCACTTGCTGC

ATTGCCTCAAAGAGAACCAGAGGATGCTTCACCAGTTGAAGATGCAAAC

ATGCTCAAGGATTTCGCTAAGTGGAGAAAGGATCTCGAAAGGGAGGGAT

TTTTCAAACCTTCTCCAGCTCATGTGGCATATAGATTTGCTGAGCTTGC

TGCAATGTTCGCTCTCGGTACAGCATTAATGTACGCTAGATGGCACGCA

ACTTCTGTTTTCGTGACAGCTTGTTTCTTTGGAGCAAGATGCGGTTGGG

TTCAACATGAGGGAGGTCACTCTTCATTGACTGGATCAATCTGGTGGGA

TAAGAGAATACAGGCTTTTACAGCAGGATTCGGTCTCGCTAGTTCTGGT

GATATGTGGAATTTAATGCATAACAAGCATCACGCAACCCCTCAAAAAG

-continued

TTAGGCACGATATGGATTTGGATACTACACCAGCTGTTGCATTTTTCAA

TACTGCTGTGGAAGAGAACAGACCTAGGAAGTTTTCTAAACTTTGGTTG

AGAGTTCAGGCTTGGACCTTCGTTCCTGTGACTTCAGGACTCGTGCTTT

TGGCTTGGATGTATCTCTTACATCCAAGACACATTGCAAGAAGGAAGAA

TTACGAAGAGGCTGCATGGATCGTTGCTGCACATGTGATAAGGACATCA

GTTATTAAAGCTGTGACAGGATATAGTTGGATAACCTGTTACGGTCTCT

TTTTAAGTACCATGTGGGTTTCTGGATGCTATCTTTTTGCTCATTTCTC

AACCAGTCATACTCACCTTGATGTTGTGCCTTCAGATAAGCATTTGAGT

TGGGTTAGATATGCTGTGGATCACACTATTGATATCGATCCATCTAAAT

CAGTTGTGAATTGGCTTATGGGTTACTTGAACTGTCAGGTTATCCATCA

CTTGTTTCCTGATATGCCACAATTCAGACAGCCAGAAGTTTCTAGAAGG

TTTGTGTCATTCGCTAAGAAATGGAATCTCAACTACAAGGTTATGTCTT

ATTACGGAGCTTGGAAAGCAACATTCGGTAACCTTAACGAAGTTGGAAA

GCACTACTATATTCAGGGTTCTCAAATCACAAAAAAGACCGTGTAA

SEQ ID NO: 20

(O809D6 Δ6-desaturase from Ostreococcus RCC809)

1 MGKGARNPGARAWKSTLEPHAVAKSFDRRWVKVDGVEYDVTDFKHPGGSVIYYMLSNTGA

61 DATEAFKEFHYRSKKARKALAALPQREPEDASPVEDANMLKDFAKWRKDLEREGFFKPSP

121 AHVAYRFAELAAMFALGTALMYARWHATSVFVTACFFGARCGWVQHEGGHSSLTGSIWWD

181 KRIQAFTAGFGLASSGDMWNLMHNKHHATPQKVRHDMDLDTTPAVAFFNTAVEENRPRKF

241 SKLWLRVQAWTFVPVTSGLVLLAWMYLLHPRHIARRKNYEEAAWIVAAHVIRTSVIKAVT

301 GYSWITCYGLFLSTMWVSGCYLFAHFSTSHTHLDVVPSDKHLSWVRYAVDHTIDIDPSKS

361 VVNWLMGYLNCQVIHHLFPDMPQFRQPEVSRRFVSFAKKWNLNYKVMSYYGAWKATFGNL

421 NEVGKHYYIQGSQITKKTV-

SEQ ID NO: 21

(codon-optimised FcELO6 Δ6-Elongase from *Fragilariopsis cylindrus* CCMP 1102)

ATGGATGAATACAAGGCAACTTTAGAGAGTGTGGGAGATGCTATAATAC

AATGGGCAGATCCTGAGAGTCAATTTACTGGTTTTACAAAGGGATGGTT

TCTTACAGATTTCACCTCAGCTTTCAGTATAGCACTTGTTTACGTGTTG

TTCGTTATTATCGGTAGTCAAGTTATGAAGGTGCTTCCTGCTATTGATC

CTTACCCAATAAAGTTTTTCTACAATGTTTCTCAGATCATGTTGTGTGC

ATACATGACTATAGAAGCTTGCCTTTTGGCATATAGAAACGGATACACA

ATCATGCCTTGTGTTGGTTATAATAGGGATGATCCAGCTATAGGAAACC

TCTTATGGCTCTTTTACGTTTCAAAAGTGTGGGATTTCTGGGATACCAT

CTTCATTGTTCTTGGTAAGAAATGGAGACAACTCAGTTTCTTACATGTG

TATCATCACACTACAATCTTTCTCTTCTACTGGTTAAATGCTAACGTTT

TCTATGATGGAGATATATACCTTACAATCGCATTGAATGGTTTCATACA

TACTGTGATGTACACATACTACTTTATCTGTATGCACACCAAGGATAAG

AAAACTGGAAAGTCTTTGCCTATATGGTGGAAGTCTTCACTCACACTTT

TGCAATTATTTCAGTTCATCACCATGATGTCACAGGGACTCTATTTAAT

AATTTTCGGTTGCGAGAGTTTGTCTATAAGGGTTACCGCTACTTACGTT

GTGTACATACTTTCTTTGTTTTTCCTCTTCGCTCAATTTTTCGTGGCAT

CTTACATGCAGCCAAAGAAATCAAAAACTGCTTGA

-continued

GAAACAGGCAACCTTTCCAGTTAACAATCCCACTTAACATATGGAACTT

CATTTTGGCTGCATTCTCAATCGCTGGAGCAGTGAAGATGACCCCTGAG

TTTTTCGGAACTATTGCTAACAAGGGTATTGTGGCATCATACTGTAAGG

TTTTCGATTTCACCAAAGGAGAAAACGGTTACTGGGTTTGGCTTTTCAT

GGCTAGTAAGCTTTTTGAGTTGGTGGATACTATCTTCCTTGTTTTGAGA

AAAAGGCCACTCATGTTCCTCCATTGGTACCATCACATCCTCACAATGA

TATACGCTTGGTACTCTCACCCTCTTACCCCAGGATTCAACAGATACGG

TATTTACTTGAACTTTGTGGTTCACGCATTCATGTACTCTTATTACTTC

CTCAGATCAATGAAGATCAGGGTTCCAGGATTTATTGCTCAAGCAATCA

CAAGTTTACAAATAGTGCAGTTCATTATCTCTTGTGCTGTTCTTGCACA

TTTGGGTTATCTCATGCACTTTACCAATGCTAACTGCGATTTTGAACCT

TCTGTGTTCAAATTGGCTGTTTTTATGGATACTACATACCTCGCACTCT

TCGTGAATTTCTTTCTTCAGTCATATGTTCTCAGGGGTGGTAAGGATAA

GTACAAAGCTGTTCCAAAGAAAAAGAATAACTGA

SEQ ID NO: 22

(FcELO6 Δ6-Elongase from *Fragilariopsis cylindrus* CCMP 1102)

1 MDEYKATLESVGDAIIQWADPESQFTGFTKGWFLTDFTSAFSIALVYVLFVIIGSQVMKV

61 LPATDPYPIKFFYNVSQIMLCAYMTIEACLLAYRNGYTIMPCVGYNRDDPAIGNLLWLFY

121 VSKVWDFWDTIFIVLGKKWRQLSFLHVYHHTTIFLFYWLNANVFYDGDIYLTIALNGFIH

181 TVMYTYYFICMHTKDKKTGKSLPIWWKSSLTLLQLFQFITMMSQGLYLIIFGCESLSIRV

241 TATYVVYILSLFFLFAQFFVASYMQPKKSKTA-

SEQ ID NO: 23

(codon-optimised CeELO6 Δ6-elongase from *Caenorhabditis elegans*)

ATGGCTCAGCACCCACTCGTTCAGAGGTTACTTGATGTTAAATTCGATA

CAAAGAGGTTCGTGGCAATAGCAACTCATGGTCCTAAAAATTTCCCTGA

TGCTGAAGGAAGAAAGTTTTTCGCAGATCATTTCGATGTTACTATTCAA

GCTAGTATACTCTACATGGTTGTGGTTTTTGGTACTAAATGGTTCATGA

SEQ ID NO: 24

(CeELO6 Δ6-elongase from *Caenorhabditis elegans*)

1 MAQHPLVQRLLDVKFDTKRFVAIATHGPKNFPDAEGRKFFADHFDVTIQASILYMVVVFG

61 TKWFMRNRQPFQLTIPLNIWNFILAAFSIAGAVKMTPEFFGTIANKGIVASYCKVFDFTK

121 GENGYWVWLFMASKLFELVDTIFLVLRKRPLMFLHWYHHILTMIYAWYSHPLTPGFNRYG

181 IYLNFVVHAFMYSYYFLRSMKIRVPGFIAQAITSLQIVQFIISCAVLAHLGYLMHFTNAN

241 CDFEPSVFKLAVFMDTTYLALFVNFFLQSYVLRGGKDKYKAVPKKKNN-

SEQ ID NO: 25

(codon-optimised TpDesK Δ4-desaturase from *Thalassiosira pseudonana*)

ATGGGTAATGGTAATCTTCCAGCATCTACAGCACAACTCAAGTCAACAA

GTAAACCTCAACAGCAACACGAGCACAGAACAATCAGTAAATCTGAATT

GGCACAACATAACACTCCTAAGTCTGCTTGGTGTGCAGTTCATTCAACT

CCTGCTACAGATCCAAGTCACTCTAATAACAAACAGCATGCACACCTTG

TTTTGGATATTACAGATTTCGCTTCTAGACATCCAGGAGGAGATTTGAT

TCTTTTGGCTTCAGGAAAAGATGCAAGTGTGCTCTTCGAGACCTACCAC

CCTAGGGGAGTTCCAACTTCATTAATTCAAAAGCTTCAGATCGGTGTTA

TGGAAGAGGAAGCTTTTAGAGATAGTTTCTACTCTTGGACAGATTCTGA

TTTCTACACCGTTCTTAAGAGAAGGGTTGTGGAAAGATTAGAGGAAAGG

GGACTTGATAGAAGGGGTTCAAAAGAGATTTGGATCAAGGCTTTATTTC

TCTTAGTTGGATTCTGGTACTGTCTTTACAAGATGTACACTACATCAGA

TATAGATCAATACGGAATAGCTATTGCATATAGTATCGGAATGGGTACT

TTTGCTGCATTCATCGGTACATGCATACAACATGATGGAAACCACGGTG

CTTTCGCACAGAACAAGCTTTTGAACAAGTTGGCTGGATGGACACTCGA

TATGATCGGTGCTTCTGCATTCACCTGGGAATTGCAGCATATGCTCGGT

CATCACCCTTACACTAATGTTCTTGATGGAGTGGAGGAAGAGAGAAAAG

-continued

AAAGGGGAGAGGATGTGGCTTTGGAAGAGAAGGATCAAGAGTCAGATCC

AGATGTTTTCTCTTCATTCCCTCTCATGAGAATGCATCCACATCACACC

ACTAGTTGGTACCATAAATATCAGCACCTTTATGCTCCTCCACTCTTTG

CATTAATGACCCTTGCTAAGGTGTTTCAACAGGATTTCGAAGTTGCAAC

ATCTGGAAGATTGTACCATATTGATGCTAACGTTAGATATGGTTCAGTT

TGGAATGTGATGAGATTCTGGGCTATGAAAGTTATCACAATGGGATACA

TGATGGGTTTGCCTATTTACTTTCATGGAGTTCTCAGGGGAGTGGGTCT

TTTCGTTATCGGACACCTTGCATGTGGTGAACTCTTAGCTACTATGTTC

ATAGTTAACCATGTGATTGAGGGAGTGAGTTATGGTACAAAAGATCTTG

TTGGAGGTGCATCTCACGGAGATGAAAAGAAAATTGTGAAGCCTACAAC

CGTTTTAGGTGATACCCCAATGGAGAAAACTAGAGAAGAGGCTCTCAAG

TCAAACAGTAACAACAACAAGAAAAAGGGAGAAAAGAACTCAGTTCCTA

GTGTGCCATTTAATGATTGGGCTGCAGTGCAATGCCAGACTTCTGTTAA

CTGGTCTCCTGGTTCATGGTTTTGGAATCATTTCAGTGGAGGTTTGTCT

CACCAAATCGAGCATCACCTCTTCCCAAGTATATGTCATACTAACTACT

GCCACATTCAAGATGTTGTGGAATCTACATGTGCTGAGTACGGTGTGCC

ATATCAGTCTGAATCAAACTTGTTCGTTGCATACGGAAAGATGATCTCA

CATTTGAAGTTCCTCGGTAAGGCTAAGTGCGAGTGA

SEQ ID NO: 26

(TpDesK Δ4-desaturase from *Thalassiosira pseudonana*)

1 MGNGNLPASTAQLKSTSKPQQQHEHRTISKSELAQHNTPKSAWCAVHSTPATDPSHSNNK

61 QHAHLVLDITDFASRHPGGDLILLASGKDASVLFETYHPRGVPTSLIQKLQIGVMEEEAF

121 RDSFYSWTDSDFYTVLKRRVVERLEERGLDRRGSKEIWIKALFLLVGFWYCLYKMYTTSD

181 IDQYGIATAYSIGMGTFAAFIGTCIQHDGNHGAFAQNKLLNKLAGWTLDMIGASAFTWEL

241 QHMLGHHPYTNVLDGVEEERKERGEDVALEEKDQESDPDVFSSFPLMRMHPHHTTSWYHK

301 YQHLYAPPLFALMTLAKVFQQDFEVATSGRLYHIDANVRYGSVWNVMRFWAMKVITMGYM

SEQ ID NO: 27

(codon-optimised Hpw-3, a w3-desaturase from *Hyaloperonospora parasitica*)

1 ATGGCTACTAAACAATCAGTTGCTTTTCCTACTTTGACTGATCTTAAAAGATCTCTTCCT

61 TCTGAGTGTTTTGAATCTTCTTTGCCTCTTTCTCTTTACTATACACTTAGATCTTTGGTT

121 TTTGCTGGTTCTCTTGCTGTTTCTCTTTCTTACGCTCTTGCTCAACCTTTGGTTCAAAAC

181 TTTTACCCTCTTAGAGTTGCTCTTATTGCTGGATACACTGTTTTTCAAGGAGTTATTTTC

241 TGGGGATTTTTCACTATTGGTCATGATGCTGGTCATGGTGCTTTTTCTAGATATCCTGTT

301 CTTAACTTCACTGTTGGAACACTTATGCATTCTCTTATTTTGACTCCTTTTGAATCTTGG

361 AAGTTGACTCATAGACATCATCATAAAAACACTGGAAATATCGATAGAGATGAGATCTTC

421 TACCCTCAAAGAGAATCTGATGATCATCCTGTTTCTAGACATCTTACTTTCACTCTTGGA

481 GCTGCTTGGTTCGCTTACCTTGTTGAGGGTTTTCCACCTAGAAAAATTGAATCATTACAAT

541 CCTTTCGAGCCATTGTTCGAGAGAAGAGTTTCTGCTGTTGTTATCTCTATCTTGGCTCAG

601 TTTTTCGTTGCAGGATTGTCTATTTACTTGTGTTTCCAGGTTGGAGTTCAGGCTGTTGCT

661 CTTTACTATTACGGTCCTATCTTCGTTTTTGGTACTATGCTTGTTATTACTACTTTTCTT

-continued

```
 721 CATCATAACGATGAAGAGACTCCTTGGTACGGTGATGAGGATTGGTCTTACGTTAAGGGT

 781 AACTTGTCTTCTGTTGATAGATCTTACGGTCCTCTTATCGATAACTTGTCTCATAACATC

 841 GGTACTCATCAAGTTCATCATCTTTTCCCAATCATCCCTCATTACAAATTAAAGCCTGCT

 901 ACAGCTGCTTTCAGAAGAGCTTTCCCACATCTTGTTAGAAAGTCTGATGAAAGAATTTTG

 961 CAGGCTTTTTACAGAATTGGTAGATTGTATGCTAAATATGGTGTTGCTGATTCTTCTGCT

1021 AAATTGTTTACATTGAAGGAAGCTCAACTTACTTCTAAAGCTGCTTCTGATGCTAAAGCT

1081 GCTTGA
```

SEQ ID NO: 28

(Hpw-3, a w3-desaturase from *Hyaloperonospora parasitica*)

```
  1 MATKQSVAFPTLTDLKRSLPSECFESSLPLSLYYTLRSLVFAGSLAVSLSYALAQPLVQN

 61 FYPLRVALIAGYTVFQGVIFWGFFTIGHDAGHGAFSRYPVLNFTVGTLMHSLILTPFESW

121 KLTHRHHHKNTGNIDRDEIFYPQRESDDHPVSRHLTFTLGAAWFAYLVEGFPPRKLNHYN

181 PFEPLFERRVSAVVISILAQFFVAGLSIYLCFQVGVQAVALYYYGPIFVFGTMLVITTFL

241 HHNDEETPWYGDEDWSYVKGNLSSVDRSYGPLIDNLSHNIGTHQVHHLFPIIPHYKLKPA

301 TAAFRRAFPHLVRKSDERILQAFYRIGRLYAKYGVADSSAKLFTLKEAQLTSKAASDAKA

361 A-
```

The invention claimed is:

1. An oil extracted from genetically modified Brassicaceae seeds, wherein said oil comprises (a) eicosapentaenoic acid (EPA) wherein EPA constitutes at least 15% (mol %) of the total fatty acid content of said oil and (b) γ-linolenic acid (GLA), wherein GLA constitutes less than 10% (mol %) of the total fatty acid content of said oil, wherein said oil is directly obtained by pressing or extracting it from the seed of said genetically modified Brassicaceae, and wherein said genetically modified Brassicaceae seeds comprise exogenous polynucleotides encoding an acyl-CoA-dependent Δ6-desaturase, a Δ6-elongase, and a Δ5-desaturase, wherein each polynucleotide is operably linked to one or more promoters that direct expression of said polynucleotides during development of the seed, wherein the Δ6-desaturase comprises an amino acid sequence that has at least 95% sequence identity to SEQ ID NO: 2 or 20, and wherein said Brassicaceae is from the *Camelina* genus.

2. The oil extracted from genetically modified Brassicaceae seeds according to claim 1, wherein the EPA constitutes at least 20% (mol %) of the total fatty acid content of said oil.

3. The oil extracted from genetically modified Brassicaceae seeds according to claim 1, wherein the GLA constitutes less than 7% (mol %) of the total fatty acid content of said oil.

4. The oil extracted from genetically modified Brassicaceae seeds according to claim 1, wherein the oil comprises phosphatidylcholine.

5. The oil extracted from genetically modified Brassicaceae seeds according to claim 1, wherein the oil comprises one or more phosphatidylethanolamine species wherein the total number of carbon atoms:double bonds of the fatty acid acyl groups of said phosphatidylethanolamine species is selected from the group consisting of 34:4, 36:7, 38:8, 38:7, 38:6, 38:5, 40:10, 40:9, 40:8, 40:7, 40:6, 40:5.

6. The oil extracted from genetically modified Brassicaceae seeds according to claim 1, wherein the seed oil comprises triglycerides wherein the number of carbon atoms:double bonds of said triglycerides is selected from the group consisting of 58:8, 58:9 and 58:10.

7. A feedstuff, food, cosmetic or pharmaceutical comprising the oil according to claim 1.

8. The oil extracted from genetically modified Brassicaceae seeds of claim 1, wherein the recombinant Brassicaceae plant further comprises one or more polynucleotides encoding at least one of a Δ12-desaturase and/or an ω3-desaturase.

9. The oil extracted from genetically modified Brassicaceae seeds of claim 1, wherein the Δ6-desaturase is derived from *Ostreococcus tauri* or *Ostreococcus* RCC809, the Δ6-elongase is derived from *Physcomitrella patens* and the Δ5-desaturase is derived from *Thraustochytrium* sp.

10. The oil extracted from genetically modified Brassicaceae seeds of claim 1, wherein the Δ6-elongase comprises an amino acid sequence having at least 95% identity to SEQ ID NO: 4, SEQ ID NO: 22 or SEQ ID NO: 24, and the Δ5-desaturase comprises an amino acid sequence having at least 95% identity to SEQ ID NO: 6 or SEQ ID NO: 10.

11. An oil extracted from genetically modified Brassicaceae seeds, wherein said oil comprises (a) eicosapentaenoic acid (EPA) wherein EPA constitutes at least 15% (mol %) of the total fatty acid content of said oil and/or docosahexaenoic acid (DHA) wherein DHA constitutes at least 5% (mol %) of the total fatty acid content of said oil and (b) γ-linolenic acid (GLA), wherein GLA constitutes less than 10% (mol %) of the total fatty acid content of said oil, wherein said oil is directly obtained by pressing or extracting it from the seed of said genetically modified Brassicaceae, and wherein said genetically modified Brassicaceae seeds comprise exogenous polynucleotides encoding an acyl-CoA-dependent Δ6-desaturase, a Δ6-elongase, a Δ5-desaturase, a Δ5-elongase and a Δ4-desaturase, wherein each polynucleotide is operably linked to one or more promoters that direct expression of said polynucleotides during development of the seed, wherein the Δ6-desaturase comprises an amino acid sequence that has at least 95% sequence identity to SEQ ID NO: 2 or 20, and wherein said Brassicaceae is from the *Camelina* genus.

12. The oil extracted from genetically modified Brassicaceae seeds according to claim 11, wherein the EPA constitutes at least 20% (mol %) of the total fatty acid content of said oil.

13. The oil extracted from genetically modified Brassicaceae seeds according to claim 11, wherein the DHA constitutes at least 13% (mol %) of the total fatty acid content of said oil.

14. The oil extracted from genetically modified Brassicaceae seeds according to claim 11, wherein the oil comprises EPA and DHA, wherein the EPA and DHA constitutes at least 20% of the total fatty acid content of said oil.

15. The oil extracted from genetically modified Brassicaceae seeds according to claim 11, wherein the GLA constitutes less than 7% (mol %) of the total fatty acid content of said oil.

16. The oil extracted from genetically modified Brassicaceae seeds of claim 11, wherein the Δ6-desaturase is derived from *Ostreococcus tauri* or *Ostreococcus* RCC809, the Δ6-elongase is derived from *Physcomitrella patens* and the Δ5-desaturase is derived from *Thraustochytrium* sp.

17. The oil extracted from genetically modified Brassicaceae seeds of claim 11, wherein the Δ6-elongase comprises an amino acid sequence having at least 95% identity to SEQ ID NO: 4, SEQ ID NO: 22 or SEQ ID NO: 24, and the Δ5-desaturase comprises an amino acid sequence having at least 95% identity to SEQ ID NO: 6 or SEQ ID NO: 10, the Δ5-elongase comprises an amino acid sequence having at least 95% identity to SEQ ID NO:8, and the Δ4-desaturase comprises an amino acid sequence having at least 95% identity to SEQ ID NO:16, SEQ ID NO: 18 or SEQ ID NO:26.

18. The oil extracted from genetically modified Brassicaceae seeds of claim 11, wherein the recombinant Brassicaceae plant further comprises one or more polynucleotides encoding at least one of a Δ12-desaturase or an ω3-desaturase.

* * * * *